(12) United States Patent
Hogrefe et al.

(10) Patent No.: US 9,783,791 B2
(45) Date of Patent: Oct. 10, 2017

(54) MUTANT REVERSE TRANSCRIPTASE AND METHODS OF USE

(75) Inventors: Holly Hogrefe, San Diego, CA (US); Bahram Arezi, Carlsbad, CA (US); Weimei Xing, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 2029 days.

(21) Appl. No.: 11/502,819

(22) Filed: Aug. 10, 2006

(65) Prior Publication Data

US 2008/0227661 A1 Sep. 18, 2008

Related U.S. Application Data

(60) Provisional application No. 60/707,019, filed on Aug. 10, 2005.

(51) Int. Cl.
| | |
|---|---|
| *C12N 9/12* | (2006.01) |
| *C12N 15/10* | (2006.01) |
| *C12Q 1/68* | (2006.01) |
| *C40B 40/08* | (2006.01) |
| *C40B 50/06* | (2006.01) |

(52) U.S. Cl.
CPC ....... *C12N 9/1276* (2013.01); *C12N 15/1096* (2013.01); *C12Q 1/686* (2013.01); *C12Y 207/07049* (2013.01); *C40B 40/08* (2013.01); *C40B 50/06* (2013.01)

(58) Field of Classification Search
USPC ......................................... 606/72–73, 79–80
See application file for complete search history.

(56) References Cited

U.S. PATENT DOCUMENTS

| | | | |
|---|---|---|---|
| 7,056,716 B2 | 6/2006 | Potter | |
| 2002/0090618 A1 * | 7/2002 | Smith et al. | 435/6 |
| 2003/0003452 A1 * | 1/2003 | Potter et al. | 435/6 |

FOREIGN PATENT DOCUMENTS

| | | |
|---|---|---|
| EP | 1712617 A1 | 10/2006 |
| JP | 2000139457 A2 | 5/2000 |
| WO | 0168895 | 9/2001 |
| WO | 0192500 | 12/2001 |
| WO | 2004/024749 A2 | 3/2004 |

OTHER PUBLICATIONS

Martinelli et al., GenBank Accession No. "AAA66622"; downloaded from ncbi.nlm.nih.gov; downloaded on Jul. 8, 2009.*
Gerard et al., (Molecular Biotechnology. vol. 8: 61-77; 1997.*
Das et al., Protein Science. vol. 10: 1936-1941; 2001.*
Das et al. Structure. vol. 12: 819-829; 2004.*
Lim, D., et al. 2002 Journal of Virology 76(16): 8360-8373.*
Halvas, E.K, et al. 2000 Journal of Virology 74(22): 10349-10358.*
Najmudin, S., et al. 2000 J Mol Biol 296: 613-632.*
International Search Report and Written Opinion in PCT/US06/31567, dated Jun. 4, 2008.
Supplementary European Search Report received in EP1931772, dated Dec. 2, 2009, pp. 1-8.
Arezi,B. et al., "Novel Mutations in Moloney Murine Leukemia Virus Reverse Transcriptase Increase Thermostability Through Tighter Binding to Template-Primer", (Feb. 2009) Nucleic Acids Research, vol. 37, No. 2, pp. 473-481.
De Stefano,J.J., et al., "Characterization of an RNase H Deficient Mutant of Human Immunodeficiency Virus-1 Reverse Transcriptase Having an Aspartate to Asparagine Change at Position 498", (Oct. 18, 1994) Biochimica et Biophysica Acta. Gene Structure and Expression, vol. 1219, No. 2, pp. 380-388.
Gerard,G.F., et al., "The Role of Template-Primer in Protection of Reverse Transcriptase from Thermal Inactivation", (Jul. 15, 2002) Nucleic Acids Research, vol. 30, No. 14, pp. 3118-3129.
Potter,J., et al., "Thermal Stability and cDNA Synthesis Capability of Superscript III Reverse Transcriptase", (Mar. 2003) Focus, vol. 25, No. 1, pp. 19-24.
Office Action dated Mar. 24, 2017 for U.S. Appl. No. 15/089,749.
Office Action dated Jun. 15, 2017 for U.S. Appl. No. 15/089,749.

* cited by examiner

*Primary Examiner* — Marsha Tsay

(57) ABSTRACT

The invention relates to the generation and characterization of stable MMLV reverse transcriptase mutants. The invention also discloses methods of using stable MMLV reverse transcriptase mutants.

41 Claims, 7 Drawing Sheets

Figure 1: MMLV-RT thermostability screen
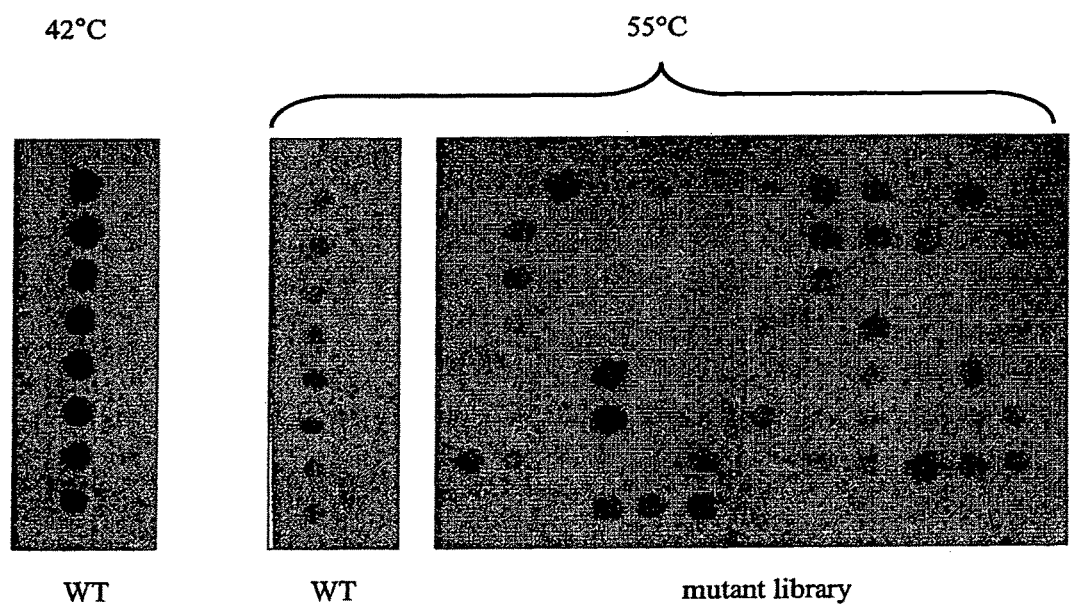

Figure 2: Thermostability of His-tagged purified MMLV-RT point mutants:

| C-Tag (Amino Acid Sequence) | % Activity at 52°C/42°C |
|---|---|
| RNase H minus MMLV-RT (WT) | 20% ± 1% |
| RNase H minus MMLV-RT (M651L) | 27% ± 0.4% |
| RNase H minus MMLV-RT (E69K) | 37% ± 0.2% |
| RNase H minus MMLV-RT (L435M) | 36% ± 0.6% |
| RNase H minus MMLV-RT (N454K) | 32.5% ± 1% |

Figure 3: Thermostability of C-terminally extended mutants:

|  | C-Tag (Amino Acid Sequence) | % Activity at 52°C/42°C |
|---|---|---|
| Exp. 1 | WT (No Tag) | 22.6% ± 0.02% |
|  | HSRRRLKRHIFN | 31% ± 1.7% |
| Exp. 2 | WT (No Tag) | 23% ± 0.2% |
|  | SKRTNPINIHTNK | 43% ± 0.4% |
|  | PS | 29% ± 0.3% |
|  | QEGKNRQGEGQT | 30% ± 0.7% |
| Exp. 4 | WT (No Tag) | 19.4% ± 0.2% |
|  | RDRNKNNDRRKAKENE | 30.3% ± 0.2% |
|  | RDRNKNNDRRKAKRDRNKNNDRRKAK | 44.3% ± 1.4% |
|  | RDRNKNNDRRKAKENEENEENEENEENE | 35.9% ± 1.6% |

Figure 4: Activity assay for RT with multiple mutations
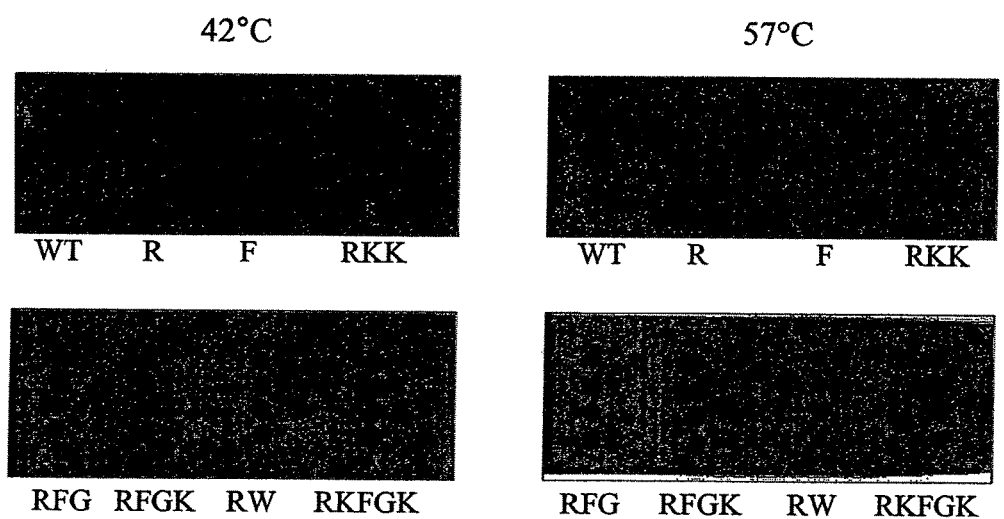

Figure 5: cDNA ladder synthesis by His-tagged StrataScript and RKFGK mutant:
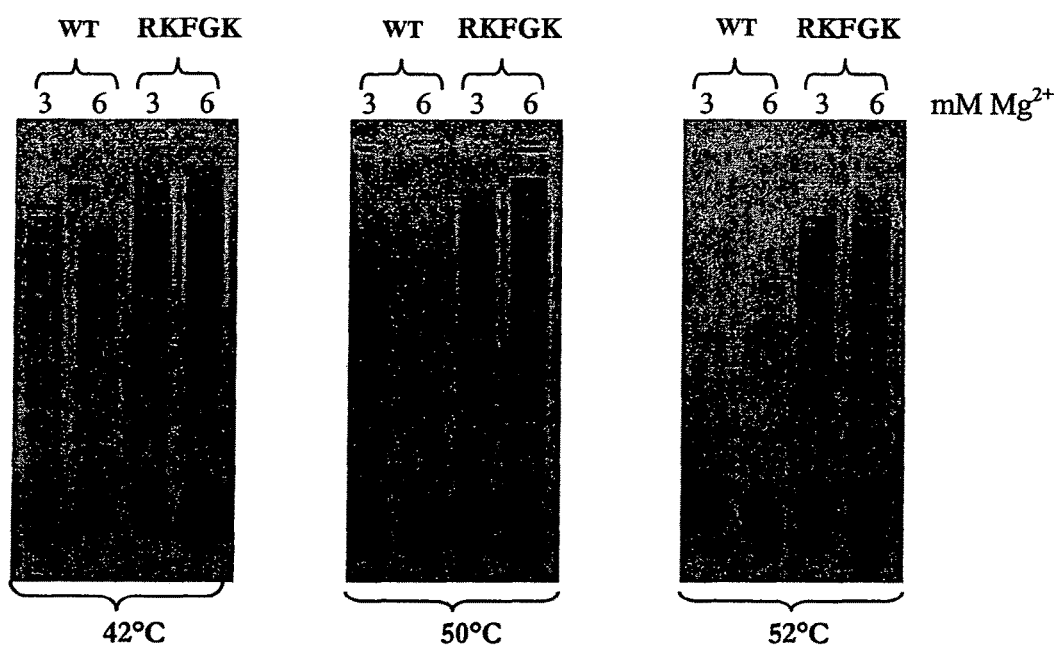

Figure 6: Thermostability comparisons of the final constructs

| RT | % activity at 55°C/42°C | % activity at 60°C/42°C |
|---|---|---|
| RNase H minus MMLV-RT | 13.6 ± 0.3 | 6.1 ± 0.07 |
| RNase H minus MMLV-RT (E302R, E69K,W313F,L435G,N454K) | 89.8 ± 4 | 36 ± 0.6 |
| RNase H minus MMLV-RT (E302R, E69K,W313F,L435G,N454K) plus C-tag (RDRNKNNDRRKAKENE) | 100.2 ± 1.4 | 52.1 ± 0.7 |

MUTANT REVERSE TRANSCRIPTASE AND METHODS OF USE

This application claims the benefit of U.S. Provisional Application No. 60/707,019, filed on Aug. 10, 2005, which is incorporated herein by reference in its entirety.

SEQUENCE LISTING

The instant application contains a Sequence Listing which has been submitted via EFS-Web and is hereby incorporated by reference in its entirety. Said ASCII copy, created on Oct. 27, 2009, is named 10070498.txt, and is 158,184 bytes in size.

FIELD OF THE INVENTION

The invention relates to mutant reverse transcriptases with increased stability.

BACKGROUND

Three prototypical forms of retroviral reverse transcriptase have been studied thoroughly. Moloney Murine Leukemia Virus (M-MLV) reverse transcriptase contains a single subunit of 78 kDa with RNA-dependent DNA polymerase and RNase H activity. This enzyme has been cloned and expressed in a fully active form in E. coli (reviewed in Prasad, V. R., Reverse Transcriptase, Cold Spring Harbor, N.Y.: Cold Spring Harbor Laboratory Press, p. 135 (1993)). Human Immunodeficiency Virus (HIV) reverse transcriptase is a heterodimer of p66 and p51 subunits in which the smaller subunit is derived from the larger by proteolytic cleavage. The p66 subunit has both an RNA-dependent DNA polymerase and an RNase H domain, while the p51 subunit has only a DNA polymerase domain. Active HIV p66/p51 reverse transcriptase has been cloned and expressed successfully in a number of expression hosts, including E. coli (reviewed in Le Grice, S. F. J., Reverse Transcriptase, Cold Spring Harbor, N.Y.: Cold Spring Harbor Laboratory press, p. 163 (1993)). Within the HIV p66/p51 heterodimer, the 51-kD subunit is catalytically inactive, and the 66-kD subunit has both DNA polymerase and RNase H activity (Le Grice, S. F. J., et al., EMBO Journal 10:3905 (1991); Hostomsky, Z., et al., J. Virol. 66:3179 (1992)). Avian Sarcoma-Leukosis Virus (ASLV) reverse transcriptase, which includes but is not limited to Rous Sarcoma Virus (RSV) reverse transcriptase, Avian Myeloblastosis Virus (AMV) reverse transcriptase, Avian Erythroblastosis Virus (AEV) Helper Virus MCAV reverse transcriptase, Avian Myelocytomatosis Virus MC29 Helper Virus MCAV reverse transcriptase, Avian Reticuloendotheliosis Virus (REV-T) Helper Virus REV-A reverse transcriptase, Avian Sarcoma Virus UR2 Helper Virus UR2AV reverse transcriptase, Avian Sarcoma Virus Y73 Helper Virus YAV reverse transcriptase, Rous Associated Virus (RAV) reverse transcriptase, and Myeloblastosis Associated Virus (MAV) reverse transcriptase, is also a heterodimer of two subunits, alpha (approximately 62 kDa) and beta (approximately 94 kDa), in which alpha is derived from beta by proteolytic cleavage (reviewed in Prasad, V. R., Reverse Transcriptase, Cold Spring Harbor, N.Y.: Cold Spring Harbor Laboratory Press (1993), p. 135). ASLV reverse transcriptase can exist in two additional catalytically active structural forms, beta beta and alpha (Hizi, A. and Joklik, W. K., J. Biol. Chem. 252: 2281 (1977)). Sedimentation analysis suggests alpha beta and beta beta are dimers and that the alpha form exists in an equilibrium between monomeric and dimeric forms (Grandgenett, D. P., et al., Proc. Nat. Acad. Sci. USA 70:230 (1973); Hizi, A. and Joklik, W. K., J. Biol. Chem. 252:2281 (1977); and Soltis, D. A. and Skalka, A. M., Proc. Nat. Acad. Sci. USA 85:3372 (1988)). The ASLV alpha beta. and beta beta reverse transcriptases are the only known examples of retroviral reverse transcriptase that include three different activities in the same protein complex: DNA polymerase, RNase H, and DNA endonuclease (integrase) activities (reviewed in Skalka, A. M., Reverse Transcriptase, Cold Spring Harbor, N.Y.: Cold Spring Harbor Laboratory Press (1993), p. 193). The alpha form lacks the integrase domain and activity.

The conversion of mRNA into cDNA by reverse transcriptase-mediated reverse transcription is an essential step in many gene expression studies. However, the use of unmodified reverse transcriptase (RT) to catalyze reverse transcription is inefficient for a number of reasons. First, reverse transcriptase sometimes degrades an RNA template before the first strand reaction is initiated or completed, primarily due to the intrinsic RNase H activity present in reverse transcriptase. In addition, mis-priming of the mRNA template molecule can lead to the introduction of errors in the cDNA first strand. RTs have in fact been shown to incorporate one base error per 3000-6000 nucleotides for HIV RT, and $1/10,000$ nucleotide for AMV RT during cDNA synthesis (Berger, S. L., et al., Biochemistry 22:2365-2372 (1983); Krug, M. S., and Berger, S. L., Meth. Enzymol. 152:316 (1987); Berger et al. Meth. Enzymol. 275: 523 (1996)). Secondary structure of the mRNA molecule itself may make some mRNAs refractory to first strand synthesis. Another factor which influences the efficiency of reverse transcription is the ability of RNA to form secondary structures. Such secondary structures can form, for example, when regions of RNA molecules have sufficient complementarity to hybridize and form double stranded RNA. Generally, the formation of RNA secondary structures can be reduced by raising the temperature of solutions which contain the RNA molecules. Thus, in many instances, it is desirable to reverse transcribe RNA at temperatures above 37° C. However, art known reverse transcriptases generally lose activity when incubated at temperatures much above 37° C. (e.g., 50° C.).

A variety of methods of attempting to engineer a thermostable reverse transcriptase are known in the art. These methods include using thermostable DNA polymerases that contain reverse transcriptase activity (Shandilya et al., *Extremophiles*, 2004 8:243), mutagenizing thermostable DNA polymerases to increase their reverse transcriptase activity (U.S. 2002/0012970), mutagenizing thermolabile reverse transcriptases (US 2004/0209276), using $Mn^{2+}$ instead of $Mg^{2+}$ in the presence of Taq/Tth DNA polymerases (Myers et al., *Biochemistry* 1991 30:7661), and using additives such as trehalose with thermolabile reverse transcriptases (Carninci et al., 1999 Proc Natl Acad Sci USA 95:520).

Scientists in the field have also tried different enzyme compositions and methods for increasing the fidelity of polymerization on DNA or RNA templates. For example, Shevelev et al., Nature Rev. Mol. Cell Biol. 3:364 (2002) provides a review on 3'-5' exonucleases. Perrino et al., PNAS, 86:3085 (1989) reports the use of epsilon subunit of E. coli DNA polymerase III to increase the fidelity of calf thymus DNA polymerase α. Bakhanashvili, Eur. J. Biochem. 268:2047 (2001) describes the proofreading activity of p53 protein and Huang et al., Oncogene, 17:261 (1998) describes the ability of p53 to enhance DNA replication fidelity. Bakhanashvili, Oncogene, 20:7635 (2001) also reports that p53 enhances the fidelity of DNA synthesis by HIV type I reverse transcriptase. Hawkins et al. describes the synthesis of full length cDNA from long mRNA transcripts (2002, Biotechniques, 34:768).

U.S. Patent Application 2003/0198944A1 and U.S. Pat. No. 6,518,019 provide an enzyme mixture containing two or more reverse transcriptases (e.g., each reverse transcriptase having a different transcription pause site) and optionally one or more DNA polymerases. U.S. Patent Application 2002/0119465A1 discloses a composition that includes a mutant thermostable DNA polymerase and a mutant reverse transcriptase (e.g., a mutant Taq DNA polymerase and a mutant MMLV-RT). U.S. Pat. No. 6,485,917B1 and U.S. Patent application 2003/0077762 and EP patent application EP1132470 provide a method for synthesizing cDNA in the presence of an enzyme having a reverse transcriptional activity and an α-type DNA polymerase having a 3'-5' exonuclease activity.

Removal of the RNase H activity of reverse transcriptase can eliminate the problem of RNA degradation of the RNA template and improve the efficiency of reverse transcription (Gerard, G. F., et al., FOCUS 11(4):60 (1989); Gerard, G. F., et al., FOCUS 14(3):91 (1992)). However such reverse transcriptases ("RNase H-" forms) do not address the additional problems of mis-priming and mRNA secondary structure.

There is a need in the art for a reverse transcriptase that exhibits increased stability.

SUMMARY OF THE INVENTION

The invention relates to the construction and characterization of thermostable MMLV reverse transcriptase. The invention also relates to methods of using the thermostable MMLV reverse transcriptase described herein, as well as kits comprising this enzyme.

The invention relates to a mutant MMLV reverse transcriptase, wherein at least one of the following amino acid positions comprises a mutation: E69, E302, W313, L435, N454 and M651.

The invention also relates to a mutant MMLV reverse transcriptase, comprising at least one of a glutamic acid to lysine mutation at position E69, a glutamic acid to lysine mutation at position E302, a glutamic acid to arginine mutation at position E302, a tryptophan to phenylalanine mutation at position W313, a leucine to glycine mutation at position L435, a leucine to methionine mutation at position L435, an asparagine to lysine mutation at position N454, an asparagine to arginine mutation at position N454, and a methionine to leucine mutation at position M651.

The invention also relates to a mutant MMLV reverse transcriptase, selected from the group consisting of: E302R/E69K/W313F/L435G/N454K; E302R/W313F/L435G/N454K; E302R/W313F/L435G; E302R/E69K/N454K; E302R/W313F; and E69K/E302R/W313F/L435G/N454K/D524N.

In one embodiment, the mutant MMLV reverse transcriptase further comprises a C-terminal extension.

In another embodiment, the C-terminal extension is RDRNKNNDRRKAKENE. (SEQ ID NO: 1)

In another embodiment, the mutant MMLV reverse transcriptase lacks RNase H activity.

In another embodiment, the mutant MMLV reverse transcriptase further comprises at least one of increased stability, increased accuracy, increased processivity, and increased specificity.

The invention also relates to an isolated polynucleotide comprising a nucleotide sequence encoding a mutant MMLV reverse transcriptase, wherein at least one of the following amino acid positions comprises a mutation: E69, E302, W313, L435, N454 and M651.

The invention also relates to an isolated polynucleotide comprising a nucleotide sequence encoding a mutant MMLV reverse transcriptase, comprising at least one of a glutamic acid to lysine mutation at position E69, a glutamic acid to lysine mutation at position E302, a glutamic acid to arginine mutation at position E302, a tryptophan to phenylalanine mutation at position W313, a leucine to glycine mutation at position L435, a leucine to methionine mutation at position L435, an asparagine to lysine mutation at position N454, an asparagine to arginine mutation at position N454, and a methionine to leucine mutation at position M651.

The invention also relates to an isolated polynucleotide comprising a nucleotide sequence encoding a mutant MMLV reverse transcriptase, selected from the group consisting of: E302R/E69K/W313F/L435G/N454K; E302R/W313F/L435G/N454K; E302R/W313F/L435G; E302R/E69K/N454K; E302R/W313F; and E69K/E302R/W313F/L435G/N454K/D524N.

In one embodiment, the isolated polynucleotide, further encodes a C-terminal extension.

In one embodiment, the C-terminal extension is RDRNKNNDRRKAKENE. (SEQ ID NO: 1)

The invention also relates to a composition comprising a mutant MMLV reverse transcriptase, wherein at least one of the following amino acid positions comprises a mutation: E69, E302, W313, L435, N454 and M651.

The invention also relates to a composition comprising a mutant MMLV reverse transcriptase, comprising at least one of a glutamic acid to lysine mutation at position E69, a glutamic acid to lysine mutation at position E302, a glutamic acid to arginine mutation at position E302, a tryptophan to phenylalanine mutation at position W313, a leucine to glycine mutation at position L435, a leucine to methionine mutation at position L435, an asparagine to lysine mutation at position N454, an asparagine to arginine mutation at position N454, and a methionine to leucine mutation at position M651.

The invention also relates to a composition comprising a mutant MMLV reverse transcriptase, selected from the group consisting of: E302R/E69K/W313F/L435G/N454K; E302R/W313F/L435G/N454K; E302R/W313F/L435G; E302R/E69K/N454K; E302R/W313F; and E69K/E302R/W313F/L435G/N454K/D524N.

In one embodiment, the mutant reverse transcriptase of the composition further comprises a C-terminal extension.

In another embodiment, the C-terminal extension is RDRNKNNDRRKAKENE. (SEQ ID NO: 1)

In another embodiment, the mutant reverse transcriptase further comprises at least one of increased stability, increased accuracy, increased processivity, and increased specificity.

In another embodiment, the reverse transcriptase lacks RNase H activity.

In another embodiment, the composition further comprises an epsilon subunit from an eubacteria.

In another embodiment, the epsilon subunit is from *Eschericia coli*.

In another embodiment, the epsilon subunit is epsilon 186 from *Eschericia coli*.

In another embodiment, the composition further comprises formamide, betaine or DMSO.

The invention also provides for a kit comprising a mutant MMLV reverse transcriptase, wherein at least one of the following amino acid positions comprises a mutation: E69, E302, W313, L435, N454 and M651, and packaging materials thereof.

The invention also provides for a kit comprising a mutant MMLV reverse transcriptase, comprising at least one of a glutamic acid to lysine mutation at position E69, a glutamic acid to lysine mutation at position E302, a glutamic acid to arginine mutation at position E302, a tryptophan to phenylalanine mutation at position W313, a leucine to glycine mutation at position L435, a leucine to methionine mutation at position L435, an asparagine to lysine mutation at position N454, an asparagine to arginine mutation at position N454, and a methionine to leucine mutation at position M651, and packaging materials thereof.

The invention also provides for a kit comprising a mutant MMLV reverse transcriptase, selected from the group consisting of: E302R/E69K/W313F/L435G/N454K; E302R/W313F/L435G/N454K; E302R/W313F/L435G; E302R/E69K/N454K; E302R/W313F; and E69K/E302R/W313F/L435G/N454K/D524N, and packaging materials thereof.

In one embodiment, the mutant reverse transcriptase of the kit lacks RNase H activity.

In another embodiment, the mutant MMLV-reverse transcriptase of the kit, further comprises a C-terminal extension.

In another embodiment, the C-terminal extension is RDRNKNNDRRKAKENE. (SEQ ID NO: 1)

In another embodiment, the mutant reverse transcriptase of the kit further comprises at least one of increased stability, increased accuracy, increased processivity, and increased specificity.

In another embodiment, the kit further comprises an epsilon subunit from an eubacteria.

In another embodiment, the epsilon subunit is from *Eschericia coli*.

In another embodiment, the epsilon subunit is epsilon 186 from *Eschericia coli*.

In another embodiment, the kit further comprises formamide, betaine or DMSO.

The invention also provides for a method for cDNA synthesis comprising providing a mutant reverse transcriptase of the invention; and contacting the mutant reverse transcriptase with a nucleic acid template to permit cDNA synthesis.

The invention also provides for a method for cloning comprising providing a mutant reverse transcriptase of the invention; contacting the mutant reverse transcriptase with a nucleic acid template to generate a synthesized cDNA product and inserting the synthesized cDNA product into a cloning vector.

The invention also provides for a method for RT-PCR comprising: providing a mutant reverse transcriptase of the invention; and contacting the mutant reverse transcriptase with a nucleic acid template to replicate and amplify the nucleic acid template.

In one embodiment, the RT-PCR comprises end-point RT-PCR.

In another embodiment, the RT-PCR is performed in real-time.

The invention also provides for a method for cDNA library construction comprising providing a mutant reverse transcriptase of the invention; contacting the mutant reverse transcriptase with a nucleic acid template to generate a synthesized cDNA product and inserting the synthesized cDNA product into a vector.

The invention also provides for a method for preparing a microarray comprising providing a mutant reverse transcriptase of the invention; contacting the mutant reverse transcriptase with a nucleic acid template to generate a synthesized cDNA product and attaching the cDNA product to a substrate.

Definitions

As used herein, "reverse transcriptase activity" and "reverse transcription" refer to the ability of an enzyme to synthesize a DNA strand (i.e. complementary DNA or cDNA) utilizing an RNA strand as a template. Reverse transcriptase activity may be measured by incubating an enzyme in the presence of an RNA template and deoxynucleotides, in the presence of an appropriate buffer, under appropriate conditions, for example as described in Example 3.

As used herein, the term "reverse transcriptase (RT)" is used in its broadest sense to refer to any enzyme that exhibits reverse transcription activity as measured by methods disclosed herein or known in the art. A "reverse transcriptase" of the present invention, therefore, includes reverse transcriptases from retroviruses, other viruses, as well as a DNA polymerase exhibiting reverse transcriptase activity, such as Tth DNA polymerase, Taq DNA polymerase, Tne DNA polymerase, Tma DNA polymerase, etc. RT from retroviruses include, but are not limited to, Moloney Murine Leukemia Virus (M-MLV) RT, Human Immunodeficiency Virus (HIV) RT, Avian Sarcoma-Leukosis Virus (ASLV) RT, Rous Sarcoma Virus (RSV) RT, Avian Myeloblastosis Virus (AMV) RT, Avian Erythroblastosis Virus (AEV) Helper Virus MCAV RT, Avian Myelocytomatosis Virus MC29 Helper Virus MCAV RT, Avian Reticuloendotheliosis Virus (REV-T) Helper Virus REV-A RT, Avian Sarcoma Virus UR2Helper Virus UR2AV RT, Avian Sarcoma Virus Y73 Helper Virus YAV RT, Rous Associated Virus (RAV) RT, and Myeloblastosis Associated Virus (MAV) RT, and as described in U.S. Patent Application 2003/0198944 (hereby incorporated by reference in its entirety). For review, see e.g. Levin, 1997, Cell, 88:5-8; Brosius et al., 1995, Virus Genes 11:163-79. Known reverse transcriptases from viruses require a primer to synthesize a DNA transcript from an RNA template. Reverse transcriptase has been used primarily to transcribe RNA into cDNA, which can then be cloned into a vector for further manipulation or used in various amplification methods such as polymerase chain reaction (PCR), nucleic acid sequence-based amplification (NASBA), transcription mediated amplification (TMA), or self-sustained sequence replication (3SR).

As used herein, the terms "reverse transcription activity" and "reverse transcriptase activity" are used interchangeably to refer to the ability of an enzyme (e.g., a reverse transcriptase or a DNA polymerase) to synthesize a DNA strand (i.e., cDNA) utilizing an RNA strand as a template. Methods for measuring RT activity are provided herein below and also are well known in the art. For example, the Quan-T-RT assay system is commercially available from Amersham (Arlington Heights, Ill.) and is described in Bosworth, et al., Nature 1989, 341:167-168.

As used herein, the term "increased" reverse transcriptase activity refers to the level of reverse transcriptase activity of a mutant enzyme (e.g., a mutant reverse transcriptase) as compared to its wild-type form. A mutant enzyme is said to have an "increased" reverse transcriptase activity if the level of its reverse transcriptase activity (as measured by methods described herein or known in the art) is at least 10% or more than its wild-type form, for example, at least 10%, 15%, 20%, 25%, 30%, 40%, 50%, 60%, 70%, 80%, 90%, 100% more or at least 2-fold, 3-fold, 4-fold, 5-fold, or 10-fold or more.

Reverse transcriptases of the invention include any reverse transcriptase having one or a combination of the properties described herein. Such properties include, but are not limited to, enhanced stability, enhanced thermostability, reduced or eliminated RNase H activity, reduced terminal deoxynucleotidyl transferase activity, increased accuracy, increased processivity, increased specificity and/or increased fidelity.

"Complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

As used herein, "mutation" refers to a change introduced into a parental or wild type DNA sequence that changes the amino acid sequence encoded by the DNA, including, but not limited to, substitutions, insertions, deletions, point mutations, mutation of multiple nucleotides or amino acids, transposition, inversion, frame shift, nonsense mutations, truncations or other forms of aberration that differentiate the polynucleotide or protein sequence from that of a wild-type sequence of a gene or gene product. The consequences of a mutation include, but are not limited to, the creation of a new character, property, function, or trait not found in the protein encoded by the parental DNA, including, but not limited to, N terminal truncation, C terminal truncation or chemical modification. A "mutation" also includes an N- or C-terminal extension.

The present invention relates in particular to mutant or modified reverse transcriptases wherein one or more (e.g., one, two, three, four, five, ten, twelve, fifteen, twenty, etc.) amino acid changes have been made which renders the enzyme more stable in nucleic acid synthesis, as compared to the unmutated or unmodified reverse transcriptases. As will be appreciated by those skilled in the art, one or more of the amino acids identified may be deleted and/or replaced with one or a number of amino acid residues. In a preferred aspect, any one or more of the amino acids may be substituted with any one or more amino acid residues such as Ala, Arg, Asn, Asp, Cys, Gln, Glu, Gly, His, Ile, Leu, Lys, Met, Phe, Pro, Ser, Thr, Trp, Tyr, and/or Val.

A reverse transcriptase of the present invention may have one or more of the following properties: (a) increased stability or increased half-life at elevated temperatures; (b) reduced, substantially reduced, or no detectable RNase H activity, (c) reduced or substantially reduced terminal deoxynucleotidyl transferase activity, (d) increased accuracy, (e) increased specificity, (f) increased processivity and/or (d) increased fidelity. In some embodiments, a reverse transcriptase of the invention may have a plurality of the properties listed above (e.g., a reverse transcriptase may have enhanced thermostability, reduced RNase H activity, and enhanced accuracy). Reverse transcriptases of the invention may have one or more of the following properties: (a) increased thermostability or increased half-life at elevated temperatures; (b) reduced, substantially reduced, or no detectable RNase H activity, (c) reduced or substantially reduced terminal deoxynucleotidyl transferase activity, and/ or (d) increased fidelity.

The term "wild-type" refers to a gene or gene product which has the characteristics of that gene or gene product when isolated from a naturally occurring source. In contrast, the term "modified" or "mutant" refers to a gene or gene product which displays altered characteristics when compared to the wild-type gene or gene product. For example, a mutant DNA polymerase in the present invention is a DNA polymerase which exhibits a reduced uracil detection activity.

As used herein, "increased" refers to greater than 10% (e.g., 11%, 12%, 13%, 14% 15%, 20%, 25%, 30%, 35%, 40%, 45%, 50%, 55%, 60%, 65%, 70%, 75%, 80%, 85%, 90%, 95%, 99% or more), as compared to a wild-type enzyme. "Increased" also refers to greater than at least 2-fold or more, (for example, 3, 4, 5, 10, 20, 50, 100, 1000, 10,000-fold or more), as compared to a wild-type enzyme.

As used herein "stable" refers to exhibiting increased activity, as defined herein, under denaturing conditions, including but not limited to higher temperatures (for example greater than 37° C. (for example 38, 39, 40, 50, 55, 60, 65, 70, 75, 80, 85° C. or more), or in the presence of denaturing agents, including but not limited to DMSO or formamide or betaine, as compared to the activity of a wild-type enzyme subjected to identical denaturing conditions.

As used herein, "stable" includes "thermostable" as defined herein.

As used herein, "thermostable refers to an enzyme which is resistant to inactivation by heat. "Thermostable" also refers to an enzyme which is stable and active at temperatures as great as preferably between about 38-100° C., for example 38, 39, 40, 45, 50, 55, 60, 65, 70, 75, 80, 85, 90, 95, 100° C. and more preferably between about 40-80° C. (for example 40, 41, 42, 43, 44, 45, 50, 55, 60, 65, 70, 75, 80° C.) to heat as compared, for example, to a non-thermostable form of an enzyme with a similar activity. Thermostable is further defined hereinbelow.

In one embodiment, the present invention provides a modified or mutated reverse transcriptase having a reverse transcriptase activity that has a half-life of greater than that of the corresponding unmodified or un-mutated reverse transcriptase at an elevated temperature, i.e., greater than 37° C. In some embodiments, the half-life of a reverse transcriptase of the present invention may be 5 minutes or greater and preferably 10 minutes or greater at 50° C. In some embodiments, the reverse transcriptases of the invention may have a half-life (e.g., at 50° C.) equal to or greater than about 25 minutes, preferably equal to or greater than about 50 minutes, more preferably equal to or greater than about 100 minutes, and most preferably, equal to or greater than about 200 minutes.

In some embodiments, the reverse transcriptases of the invention may have a half-life at 50° C. that is from about 10 minutes to about 200 minutes, from about 10 minutes to about 150 minutes, from about 10 minutes to about 100 minutes, from about 10 minutes to about 75 minutes, from about 10 minutes to about 50 minutes, from about 10 minutes to about 40 minutes, from about 10 minutes to about 30 minutes, or from about 10 minutes to about 20 minutes.

Mutated or modified reverse transcriptases of the present invention may have a reverse transcriptase activity (e.g., RNA-dependent DNA polymerase activity) that has a longer half-life at 55° C. than the reverse transcriptase activity of a corresponding un-mutated or unmodified reverse transcriptase. At 55° C., the half-life of reverse transcriptase activity of a mutated or modified reverse transcriptase of the invention may be greater than about 2 minutes, greater than about 3 minutes, greater than about 4 minutes, greater than about 5 minutes, greater than about 6 minutes, greater than about 7 minutes, greater than about 8 minutes, greater than about 10 minutes, greater than about 15 minutes, greater than about 20 minutes, or greater than about 30 minutes. At 55° C., the half-life of reverse transcriptase activity of a reverse transcriptase of the invention may be from about 2 minutes to about 60 minutes, from about 2 minutes to about 45 minutes, from about 2 minutes to about 30 minutes, from about 2 minutes to about 20 minutes, from about 2 minutes to about 15 minutes, from about 2 minutes to about 10 minutes, from about 2 minutes to about 8 minutes, from about 2 minutes to about 7 minutes, from about 2 minutes to about 6 minutes, from about 2 minutes to about 5 minutes, from about 2 minutes to about 4 minutes, or from about 2 minutes to about 3 minutes.

Reverse transcriptases of the present invention may produce more product (e.g., full length product) at elevated temperatures than other reverse transcriptases. In one aspect, comparisons of full length product synthesis is made at different temperatures (e.g., one temperature being lower, such as between 37° C. and 50° C., and one temperature being higher, such as between 50° C. and 78° C.) while keeping all other reaction conditions similar or the same. The amount of full length product produced may be determined using techniques well known in the art, for example, by conducting a reverse transcription reaction at a first temperature (e.g., 37° C., 38° C., 39° C., 40° C., etc.) and determining the amount of full length transcript produced, conducting a second reverse transcription reaction at a temperature higher than the first temperature (e.g., 45° C., 50° C., 52.5° C., 55° C., etc.) and determining the amount of full length product produced, and comparing the amounts produced at the two temperatures. A convenient form of comparison is to determine the percentage of the amount of full length product at the first temperature that is produced at the second (i.e., elevated) temperature. The reaction conditions used for the two reactions (e.g., salt concentration, buffer concentration, pH, divalent metal ion concentration, nucleoside triphosphate concentration, template concentration, reverse transcriptase concentration, primer concentration, length of time the reaction is conducted, etc.) are preferably the same for both reactions. Suitable reaction conditions include, but are not limited to, a template concentration of from about 1 nM to about 1 µM, from about 100 nM to 1 µM, from about 300 nM to about 750 nM, or from about 400 nM to about 600 nM, and a reverse transcriptase concentration of from about 1 nM to about 1 µM, from about 10 nM to 500 nM, from about 50 nM to about 250 nM, or from about 75 nM to about 125 nM. The ratio of the template concentration to the reverse transcriptase concentration may be from about 100:1 to about 1:1, from about 50:1 to about 1:1, from about 25:1 to about 1:1, from about 10:1 to about 1:1, from about 5:1 to about 1:1, or from about 2.5:1 to 1:1. A reaction may be conducted from about 5 minutes to about 5 hours, from about 10 minutes to about 2.5 hours, from about 30 minutes to about 2 hours, from about 45 minutes to about 1.5 hours, or from about 45 minutes to about 1 hour. A suitable reaction time is about one hour. Other suitable reaction conditions may be determined by those skilled in the art using routine techniques and examples of such conditions are provided below.

When the amount of full length product produced by a reverse transcriptase of the invention at an elevated temperature is compared to the amount of full length product produced by the same reverse transcriptase at a lower temperature, at an elevated temperature, the reverse transcriptases of the invention may produce not less than about 25%, 35%, 45%, 55%, 65%, 75%, 85%, 95%, 100% of the amount of full length product produced at the lower temperature. In some cases, the reverse transcriptases of the invention may produce an amount of full length product at a higher temperature that is greater than the amount of full length product produced by the reverse transcriptase at a lower temperature (e.g., 1% to about 100% greater). In one aspect, reverse transcriptases of the invention produce approximately the same amount (e.g., no more than a 25% difference) of full length product at the lower temperature compared to the amount of full length product made at the higher temperature.

A reverse transcriptase of the present invention may be one that synthesizes an amount of full length product, wherein the amount of full length product synthesized at 50° C. is no less than 10% (e.g., from about 10% to about 95%, from about 10% to about 80%, from about 10% to about 70%, from about 10% to about 60%, from about 10% to about 50%, from about 10% to about 40%, from about 10% to about 30%, or from about 10% to about 20%) of the amount of full length product it synthesizes at 40° C. In some embodiments, a reverse transcriptase of the invention is one wherein the amount of full length product synthesized at 50° C. is no less than 50% (e.g., from about 50% to about 95%, from about 50% to about 80%, from about 50% to about 70%, or from about 50% to about 60%) of the amount of full length product it synthesizes at 40° C. In some embodiments, a reverse transcriptase of the invention is one wherein the amount of full length product synthesized at 50° C. is no less than 75% (e.g., from about 75% to about 95%, from about 75%, to about 90%, from about 75% to about 85%, or from about 75% to about 80%) of the amount of full length product it synthesizes at 40° C. In other embodiments, a reverse transcriptase of the invention is one wherein the amount of full length product synthesized at 50° C. is no less than 85% (e.g., from about 85% to about 95%, or from about 85% to about 90%) of the amount of full length product it synthesizes at 40° C.

A reverse transcriptase of the invention may be one that synthesizes an amount of full length product, wherein the amount of full length product synthesized at 52.5° C. is no less than 10% (e.g., from about to about 30%, from about 10% to about to about 25%, from about 10% to about 20%, from about 10% to about 15%, from about 20% to about 60%, from about 20% to about 40%, from about 20% to about 30%, from about 30% to about 80%, from about 30% to about 60%, from about 30% to about 45%, from about 40% to about 90%, from about 40% to about 80%, from about 40% to about 60%, from about 40% to about 50% from about 50% to about 90%, or from about 50% to about 70%), of the amount of full length product it synthesizes at 40° C. In some embodiments, the amount of full length product synthesized at 52.5° C. is no less than 30% (e.g., from about 30% to about 70%, from about 30% to about 60%, from about 30% to about 50%, or from about 30% to about 40%) of the amount of full length product it synthesizes at 40° C. In some embodiments, the amount of full length product synthesized at 52.5° C. is no less than 50% (e.g., from about 50% to about 70%, from about 50% to about 65%, from about 50% to about 60%, or from about 50% to about 55%), of the amount of full length product it synthesizes at 40° C.

A reverse transcriptase of the invention may be one that synthesizes an amount of full length product, wherein the amount of full length product synthesized at 55° C. is no less than 1% (e.g., from about 1% to about 30%, from about 1% to about 25%, from about 1% to about 20%, from about 1% to about 15%, from about 1% to about 10%, or from about 1% to about 5%) of the amount of full length product it synthesizes at 40° C. In some embodiments, the amount of full length product synthesized at 55° C. is no less than 5% (e.g., from about 5% to about 30%, from about 5% to about to about 25%, from about 5% to about 20%, from about 5% to about 15%, or from about 5% to about 10%) of the amount of full length product it synthesizes at 40° C. In some embodiments, the amount of full length product synthesized at 55° C. is no less than 10% (e.g., from about 10% to about 30%, from about 10% to about to about 25%, from about 10% to about 20%, from about 10% to about 15%, from about 20% to about 60%, from about 20% to about 40%, from about 20% to about 30%, from about 30% to about 80%, from about 30% to about 60%, from about 30% to about 45%, from about 40% to about 90%, from about 40% to about 80%, from about 40% to about 60%, from about 40% to about 50% from about 50% to about 90%, or from about 50% to about 70%) of the amount of full length product it synthesizes at 40° C.

In another aspect, the reverse transcriptases of the invention are capable of producing more nucleic acid product (e.g., cDNA) and, preferably, more full length product, at one or a number of elevated temperatures (typically between 40° C. an 78° C.) compared to the corresponding un-mutated or unmodified reverse transcriptase (e.g., the control reverse transcriptase). Such comparisons are typically made under similar or the same reaction conditions and the amount of product synthesized by the control reverse transcriptase is compared to the amount of product synthesized by the reverse transcriptase of the invention. Preferably, the reverse transcriptases of the invention produce at least about 5%, at least 10%, at least 15%, at least 25%, at least 50%, at least 75%, at least 100%, or at least 200% more product or full length product compared to the corresponding control reverse transcriptase under the same reaction conditions and temperature. The reverse transcriptases of the invention preferably produce from about 10% to about 200%, from about 25% to about 200%, from about 50% to about 200%, from about 75% to about 200%, or from about 100% to about 200% more product or full length product compared to a control reverse transcriptase under the same reaction conditions and incubation temperature. The reverse transcriptases of the invention preferably produce at least 2 times, at least 3 times, at least 4 times, at least 5 times, at least 6 times, at least 7 times, at least 8 times, at least 9 times, at least 10 times, at least 25 times, at least 50 times, at least 75 times, at least 100 times, at least 150 times, at least 200 times, at least 300 times, at least 400 times, at least 500 times, at least 1000 times, at least 5,000 times, or at least 10,000 times more product or full length product compared to a control reverse transcriptase (e.g., the corresponding un-mutated or unmodified reverse transcriptase) under the same reaction conditions and temperature. The reverse transcriptases of the invention preferably produce from 2 to 10,000, 5 to 10,000, 10 to 5,000, 50 to 5,000, 50 to 500, 2 to 500, 5 to 500, 5 to 200, 5 to 100, or 5 to 75 times more product or full length product than a control reverse transcriptase under the same reaction conditions and temperature.

In one aspect, the reverse transcriptases of the invention produce, at 50° C., at least 25% more, preferably at least 50% more and more preferably at least 100% more nucleic acid product or full length product than a control reverse transcriptase (which is preferably the corresponding wild-type reverse transcriptase). In another aspect, at 52.5° C., the reverse transcriptases of the invention produce at least 1.5 times, at least 2 times, at least 2.5 times, at least 3 times, at least 4 times, at least 5 times, at least 6 times, at least 7 times, at least 8 times, at least 9 times, at least 10 times the amount of nucleic acid product or full length product compared to a control reverse transcriptase. In another aspect, at 55° C., the reverse transcriptases of the invention produce at least 2 times, at least 5 times, at least 10 times, at least 15 times, at least 20 times, at least 25 times, at least 50 times, at least 75 times, at least 100 times the amount of nucleic acid product or full length product compared to a control reverse transcriptase. Such comparisons are preferably made under the same reaction conditions and temperature.

Modified or mutated reverse transcriptases of the present invention may have an increased thermostability at elevated temperatures as compared to corresponding unmodified or un-mutated reverse transcriptases. They may show increased thermostability in the presence or absence an RNA template. In some instances, reverse transcriptases of the invention may show an increased thermostability in both the presence and absence of an RNA template. Those skilled in the art will appreciate that reverse transcriptase enzymes are typically more thermostable in the presence of an RNA template. The increase in thermostability may be measured by comparing suitable parameters of the modified or mutated reverse transcriptase of the invention to those of a corresponding unmodified or un-mutated reverse transcriptase. Suitable parameters to compare include, but are not limited to, the amount of product and/or full length product synthesized by the modified or mutated reverse transcriptase at an elevated temperature compared to the amount or product and/or full length product synthesized by the corresponding un-modified or un-mutated reverse transcriptase at the same temperature, and/or the half-life of reverse transcriptase activity at an elevated temperature of a modified or mutated reverse transcriptase at an elevated temperature compared to that of a corresponding unmodified or un-mutated reverse transcriptase.

A modified or mutated reverse transcriptase of the invention may have an increase in thermostability at 50° C. of at least about 1.5 fold (e.g., from about 1.5 fold to about 100 fold, from about 1.5 fold to about 50 fold, from about 1.5 fold to about 25 fold, from about 1.5 fold to about 10 fold) compared, for example, to the corresponding un-mutated or unmodified reverse transcriptase. A reverse transcriptase of the invention may have an increase in thermostability at 50° C. of at least about 10 fold (e.g., from about 10 fold to about 100 fold, from about 10 fold to about 50 fold, from about 10 fold to about 25 fold, or from about 10 fold to about 15 fold) compared, for example, to the corresponding un-mutated or unmodified reverse transcriptase. A reverse transcriptase of the invention may have an increase in thermostability at 50° C. of at least about 25 fold (e.g., from about 25 fold to about 100 fold, from about 25 fold to about 75 fold, from about 25 fold to about 50 fold, or from about 25 fold to about 35 fold) compared to a corresponding un-mutated or unmodified reverse transcriptase.

The present invention also contemplates a modified or mutated thermostable reverse transcriptase, wherein the reverse transcriptase has an increase in thermostability of greater than about 1.5 fold at 52.5° C. (e.g., from about 1.5 fold to about 100 fold, from about 1.5 fold to about 50 fold, from about 1.5 fold to about 25 fold, or from about 1.5 fold to about 10 fold) compared, for example, to the corresponding un-mutated or unmodified reverse transcriptase. A reverse transcriptase of the invention may have an increase in thermostability at 52.5° C. of at least about 10 fold (e.g., from about 10 fold to about 100 fold, from about 10 fold to about 50 fold, from about 10 fold to about 25 fold, or from about 10 fold to about 15 fold) compared, for example, to the corresponding un-mutated or unmodified reverse transcriptase. A reverse transcriptase of the invention may have an increase in thermostability at 52.5° C. of at least about 25 fold (e.g., from about 25 fold to about 100 fold, from about 25 fold to about 75 fold, from about 25 fold to about 50 fold, or from about 25 fold to about 35 fold) compared, for example, to the corresponding un-mutated or unmodified reverse transcriptase.

In other embodiments, the present invention provides a reverse transcriptase, wherein the reverse transcriptase has an increase in thermostability of greater than about 1.5 fold at 55° C. (e.g., from about 1.5 fold to about 100 fold, from about 1.5 fold to about 50 fold, from about 1.5 fold to about 25 fold, or from about 1.5 fold to about 10 fold) compared to a corresponding un-mutated or unmodified reverse transcriptase. In some embodiments, a reverse transcriptase of the invention may have an increase in thermostability at 55° C. of at least about 10 fold (e.g., from about 10 fold to about 100 fold, from about 10 fold to about 50 fold, from about 10 fold to about 25 fold, or from about 10 fold to about 15 fold) compared to a corresponding un-mutated or unmodified reverse transcriptase. In some embodiments, a reverse transcriptase of the invention may have an increase in thermostability at 55° C. of at least about 25 fold (e.g., from about 25 fold to about 100 fold, from about 25 fold to about 75 fold, from about 25 fold to about 50 fold, or from about 25 fold to about 35 fold) compared to a corresponding un-mutated or unmodified reverse transcriptase.

Nucleic acid templates suitable for reverse transcription according to this aspect of the invention include any nucleic acid molecule or population of nucleic acid molecules (preferably RNA and most preferably mRNA), particularly those derived from a cell or tissue. In a specific aspect, a population of mRNA molecules (a number of different mRNA molecules, typically obtained from a particular cell or tissue type) is used to make a cDNA library, in accordance with the invention. Examples of cellular sources of nucleic acid templates include bacterial cells, fungal cells, plant cells and animal cells.

As used herein, a "C-terminal extension" refers to a peptide tail of random sequence. A C-terminal extension is preferably from 1 to 500 amino acids, more preferably from 1 to 100, amino acids, and most preferably from 2 to 50 amino acids.

As used herein, "random" means relating to an amino acid sequence, wherein each amino acid of the sequence has an equal probability of occurring.

As used herein, "RNase H activity" refers to endoribonuclease degradation of the RNA of a DNA-RNA hybrid to produce 5' phosphate terminated oligonucleotides that are 2-9 bases in length. RNase H activity does not include degradation of single-stranded nucleic acids, duplex DNA or double-stranded RNA.

As used herein, the phrase "substantially lacks RNase H activity" means having less than 10%, 5%, 1%, 0.5%, or 0.1% of the activity of a wild type enzyme. The phrase "lacking RNase H activity" means having undetectable RNase H activity or having less than about 1%, 0.5%, or 0.1% of the RNase H activity of a wild type enzyme.

An enzyme with "reduced" RNase H activity is meant that the enzyme has less than 50%, e.g., less than 40%, 30%, or less than 25%, 20%, more preferably less than 15%, less than 10%, or less than 7.5%, and most preferably less than 5% or less than 2%, of the RNase H activity of the corresponding wild type enzyme containing RNase H activity. The RNase H activity of an enzyme may be determined by a variety of assays, such as those described, for example, in U.S. Pat. Nos. 5,405,776; 6,063,608; 5,244,797; and 5,668,005 in Kotewicz, M. L., et al., Nucl. Acids Res. 16:265 (1988) and Gerard, G. F., et al., FOCUS 14(5):91 (1992), the disclosures of all of which are fully incorporated herein by reference.

As used herein, "processivity" refers to the ability of a nucleic acid modifying enzyme, for example a reverse transcriptase, to remain attached to the template or substrate and perform multiple modification reactions. "Modification reactions" include but are not limited to synthesis. "Processivity" also refers to the ability of a nucleic acid modifying enzyme, for example a reverse transcriptase, to perform a sequence of steps without intervening dissociation of the enzyme from the growing DNA chains. "Processivity" can depend on the nature of the nucleic-acid modifying enzyme, the sequence of a nucleic acid template, and reaction conditions, for example, salt concentration, temperature or the presence of specific proteins.

As used herein, "increased processivity" refers to an increase of 5-10%, preferably 10-50%, more preferably 50-100% or more, as compared to a wild type reverse transcriptase. Processivity and increased processivity can be measured as described in Malboeuf et al., 2001, Biotechniques 30: 1074.

As used herein, "accuracy" refers to "fidelity", defined hereinbelow. Accuracy or fidelity can be measured as described in U.S. Patent Application Nos. 60/559,810 and 11,100,183, incorporated by reference it their entirety herein.

As used herein, "specificity" refers to a decrease in the amount of mispriming by the reverse transcriptase at the cDNA synthesis level when the reaction is performed at higher temperature, as compared to the amount of mispriming by a wild-type reverse transcriptase performing under identical conditions. Specificity can be measured as described in Mizuno Y, et al., Nucleic Acids Research, 1999, 27: 1345-1349.

As used herein, "decrease" refers to at least 1-fold or more, for example, 1, 2, 3, 4, 5, 10, 20, 30, 40, 50, 60, 70, 80, 90, 100, 1000-fold or more, less than a wild-type enzyme performing under identical conditions. "Decrease" also refers to at least 5% or more (for example 5, 6, 7, 8, 9, 10, 20, 30, 40, 50, 60, 70, 80, 90, 99, 100%) less than a wild-type enzyme performing under identical conditions.

The term "fidelity," as used herein, refers to the accuracy of nucleotide synthesis by reverse transcriptase or template-dependent DNA polymerase, e.g., RNA-dependent or DNA-dependent DNA polymerase. The fidelity of a DNA polymerase, including a reverse transcriptase, is measured by the error rate (the frequency of incorporating an inaccurate nucleotide, i.e., a nucleotide that is not incorporated in a template-dependent manner). The accuracy or fidelity of DNA polymerization is maintained by both the polymerase activity and the 3'-5' exonuclease activity. The term "high fidelity" refers to an error rate equal to or lower than $33 \times 10^{-6}$ per base pair (see Roberts J. D. et al., Science, 1988, 242: 1171-1173, the entirety hereby incorporated by reference). The fidelity or error rate of a DNA polymerase may be measured using assays known to the art (see for example, Lundburg et al., 1991 Gene, 108:1-6).

A reverse transcriptase having an "increased (or enhanced or higher) fidelity" is defined as a mutant or modified reverse transcriptase (including a DNA polymerase exhibiting reverse transcriptase activity) having any increase in fidelity compared to its wild type or unmodified form, i.e., a reduction in the number of misincorporated nucleotides during synthesis of any given nucleic acid molecule of a given length. Preferably there is 1.5 to 1,000 fold (more preferably 2 to 100 fold, more preferably 3 to 10 fold) reduction in the number of misincorporated nucleotides during synthesis of any given nucleic acid molecule of a given length. For example, a mutated reverse transcriptase may misincorporate one nucleotide in the synthesis of a nucleic acid molecule segment of 1000 bases compared to an unmutated reverse transcriptase misincorporating 10 nucleotides in the same size segment. Such a mutant reverse transcriptase would be said to have a 10-fold increase in fidelity.

As used herein, the terms "nucleic acid", "polynucleotide" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases (including abasic sites). There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single-stranded RNA.

As used herein, "nucleotide" refers to a base-sugar-phosphate combination. Nucleotides are monomeric units of a nucleic acid sequence (DNA and RNA) and deoxyribonucleotides are "incorporated" into DNA by DNA polymerases. The term nucleotide includes, but is not limited to, deoxyribonucleoside triphosphates such as dATP, dCTP, dITP, dUTP, dGTP, dTTP, or derivatives thereof. Such derivatives include, for example, [aS]dATP, 7-deaza-dGTP, 7-deaza-dATP, amino-allyl dNTPs, fluorescent labeled dNTPs including Cy3, Cy5 labeled dNTPs. The term nucleotide as used herein also refers to dideoxyribonucleoside triphosphates (ddNTPs and acyclic nucleotides) and their derivatives (e.g., as described in Martinez et al., 1999, Nucl. Acids Res. 27: 1271-1274, hereby incorporated by reference in its entirety).

As used herein, a "primer" refers to a sequence of deoxyribonucleotides or ribonucleotides comprising at least 3 nucleotides. Generally, the primer comprises from about 3 to about 100 nucleotides, preferably from about 5 to about 50 nucleotides and even more preferably from about 5 to about 25 nucleotides. A primer having less than 50 nucleotides may also be referred to herein as an "oligonucleotide primer". The primers of the present invention may be synthetically produced by, for example, the stepwise addition of nucleotides or may be fragments, parts, portions or extension products of other nucleotide acid molecules. The term "primer" is used in its most general sense to include any length of nucleotides which, when used for amplification purposes, can provide a free 3' hydroxyl group for the initiation of DNA synthesis by a DNA polymerase, either using an RNA or a DNA template. DNA synthesis results in the extension of the primer to produce a primer extension product complementary to the nucleic acid strand to which the primer has hybridized.

As used herein, the term "homology" refers to the optimal alignment of sequences (either nucleotides or amino acids), which may be conducted by computerized implementations of algorithms. "Homology", with regard to polynucleotides, for example, may be determined by analysis with BLASTN version 2.0 using the default parameters. "Homology", with respect to polypeptides (i.e., amino acids), may be determined using a program, such as BLASTP version 2.2.2 with the default parameters, which aligns the polypeptides or fragments being compared and determines the extent of amino acid identity or similarity between them. It will be appreciated that amino acid "homology" includes conservative substitutions, i.e. those that substitute a given amino acid in a polypeptide by another amino acid of similar characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp or Glu with another acidic residue; replacement of a residue bearing an amide group, such as Asn or Gln, with another residue bearing an amide group; exchange of a basic residue such as Lys or Arg with another basic residue; and replacement of an aromatic residue such as Phe or Tyr with another aromatic residue. A polypeptide sequence (i.e., amino acid sequence) or a polynucleotide sequence comprising at least 50% homology to another amino acid sequence or another nucleotide sequence respectively has a homology of 50% or greater than 50%, e.g., 60%, 70%, 80%, 90% or 100% (i.e., identical).

The term "E. coli DNA polymerase III holoenzyme" refers to an E. coli polymerase III holoenzyme composed of ten subunits assembled in two catalytic cores, two sliding clamps and a clamp loader, e.g., as described in Kelman, Z. & O'Donnell, M. (1995). Annu. Rev. Biochem. 64, 171200 (the entirety is hereby incorporated by reference).

The term "epsilon (ε) subunit," according to the present invention, refers to a ε subunit having 3'-5' exonuclease activity. An epsilon subunit may be from any eubacteria, such as from E. coli, or from other organisms. The epsilon (ε) subunit of the E. coli DNA polymerase III holoenzyme is the 3'-5' exonuclease of the holoenzyme and interacts with the α (polymerase unit) and θ (unknown function) subunits (see, e.g., Fijalkowska et al., 1996, Proc. Natl. Acad. Sci. USA, 93: 2856-2861, the entirety is hereby incorporated by reference). The epsilon (ε) subunit of E. coli DNA polymerase III holoenzyme (see FIG. 9) is encoded by dnaQ gene (see FIG. 9). The epsilon subunit of the present invention also includes a wild type polypeptide which is at least 50% homologous (e.g., 60%, 70%, 80%, 90%, or identical) to the sequences presented in FIG. 9 and contains 3'-5' exonuclease activity. The epsilon (ε) subunit, according to the present invention, further includes a mutant epsilon (ε) subunit which still contains 3'-5' exonuclease activity. Such mutant epsilon may contain a deletion (e.g., truncation), substitution, point mutation, mutation of multiple amino acids, or insertion to the wild type epsilon subunit. For example, a truncated epsilon useful according to the invention may be, for example, as disclosed in Hamdan S. et al., Biochemistry 2002, 41: 5266-5275, the entirety hereby incorporated by reference.

As used herein, "epsilon 186" refers to the N-terminal domain of the epsilon subunit (codons 2-186 of dnaQ), as disclosed in Hamdan et al., supra.

The term "θε subunit complex" or "θε186 subunit complex" refers to the combination of the epsilon subunit or a mutant epsilon subunit of E. coli DNA polymerase III holoenzyme (for example epsilon 186) in combination with the θ subunit of E. coli DNA polymerase III holoenzyme.

As used herein, the term "eubacteria" refers to unicelled organisms which are prokaryotes (e.g., as described in Garrity, et al., 2001, Taxonomic outline of the procaryotic genera. Bergey's Manual® of Systematic Bacteriology, Second Edition. Release 1.0, April 2001, and in Werren, 1997, Annual Review of Entomology 42: 587-609). Eubacteria include the following genera: *Escherichia, Pseudomonas, Proteus, Micrococcus, Acinetobacter, Klebsiella, Legionella, Neisseria, Bordetella, Vibrio, Staphylococcus, Lactobaccilus, Streptococcus, Bacillus, Corynebacteria, Mycobacteria, Clostridium*, and others (see Kandler, O., Zbl. Bakt.Hyg., I.Abt.Orig. C3, 149-160 (1982)), as well as major sub-groups of eubacteria such as Aquifex (extremely thermophilic chemolithotrophs), *Thermotoga* (extremely thermophilic chemoorganotrophs), *Chloroflexus* (thermophilic photosynthetic bacteria), *Deinococcus* (radiation resistant bacteria), *Thermus* (thermophilic chemoheterotrophs), *Spirochaetes* (helical bacteria with periplasmic flagella), *Proteobacteria* (Gram-negative and purple photosynthetic bacteria), *Cyanobacteria* (blue-green photosynthetic bacteria), Gram-positives (Gram-positive bacteria), *Bacteroides/Flavobacterium* (strict anaerobes/strict aerobes with gliding motility), *Chlorobium* (photoautotrophic sulphur-oxidisers), *Planctomyces* (budding bacteria with no peptidoglycan), *Chlamydia* (intracellular parasites). Eubacteria include all thermostable bacteria.

As used herein, "synthesis" refers to any in vitro method for making a new strand of polynucleotide or elongating existing polynucleotide (i.e., DNA or RNA) in a template dependent manner. Synthesis, according to the invention, may include amplification, which increases the number of copies of a polynucleotide template sequence with the use of a polymerase. Polynucleotide synthesis results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules.

As used herein, an "amplified product" refers to the single- or double-strand polynucleotide population at the end of an amplification reaction. The amplified product contains the original polynucleotide template and polynucleotide synthesized by DNA polymerase using the polynucleotide template during the amplification reaction. An amplified product preferably is produced by a reverse transcriptase and/or a DNA polymerase.

As used herein, "polynucleotide template" or "target polynucleotide template" refers to a polynucleotide (RNA or DNA) which serves as a template for a DNA polymerase to synthesize DNA in a template-dependent manner. The "amplified region," as used herein, is a region of a polynucleotide that is to be either synthesized by reverse transcription or amplified by polymerase chain reaction (PCR). For example, an amplified region of a polynucleotide template may reside between two sequences to which two PCR primers are complementary to.

As used herein, the term "template dependent manner" refers to a process that involves the template dependent extension of a primer molecule (e.g., DNA synthesis by DNA polymerase). "Template dependent manner" refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene*, 4th Ed., W. A. Benjamin, Inc., Menlo Park, Calif. (1987)).

As used herein, the term "polymerase chain reaction" ("PCR") refers to the method of K. B. Mullis, e.g., as described in U.S. Pat. Nos. 4,683,195 4,683,202, and 4,965,188 (each hereby incorporated in its entirety by reference) and any other improved method known in the art. PCR is a method for increasing the concentration of a segment of a target sequence in a mixture of genomic DNA without cloning or purification. This process for amplifying the target sequence typically consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "RT-PCR" refers to the replication and amplification of RNA sequences. In this method, reverse transcription is coupled to PCR, e.g., as described in U.S. Pat. No. 5,322,770, herein incorporated by reference in its entirety. In RT-PCR, the RNA template is converted to cDNA due to the reverse transcriptase activity of an enzyme, and then amplified using the polymerizing activity of the same or a different enzyme. Stable, thermostable or thermolabile reverse transcriptase and polymerase can be used.

Amino acid residues identified herein are preferred in the natural L-configuration. In keeping with standard polypeptide nomenclature, J. Biol. Chem., 243:3557-3559, 1969, abbreviations for amino acid residues are as shown in the following Table 1.

TABLE 1

| 1-Letter | 3-Letter | AMINO ACID |
|---|---|---|
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

A "double tube RT-PCR" or "two step RT-PCR" refers to a reaction wherein the RT step is performed in a first tube, and then the cDNA is transferred to a second tube for amplification. Therefore, the cDNA synthesis and PCR occur in two separate tubes. A "single tube RT-PCR" or "one step RT-PCR" refers to a reaction wherein both cDNA synthesis and PCR are performed in the same tube.

As used herein, "end-point RT-PCR" refers to RT-PCR wherein a template is added at the beginning of a PCR reaction and the reaction is carried out in multiple cycles, usually 20 to 50 cycles. It is the end product of the amplification reaction which is detected and/or quantitated.

As used herein, "real time RT-PCR" or "quantitative" or "QRT-PCR" refers to an RT-PCR process wherein the progress of an RT-PCR amplification is measured or detected as it is occurring. In real-time RT-PCR techniques, signals (generally fluorescent) are monitored as they are generated and are tracked after they rise above background but before the reaction reaches a plateau.

As used herein, the term "real-time" refers to that which is performed contemporaneously with the monitored, measured or observed events and which yields as a result of the monitoring, measurement or observation to one who performs it simultaneously, or effectively so, with the occurrence of a monitored, measured or observed event. Thus, a "real time" assay or measurement contains not only the measured and quantitated result, such as generated signal, but expresses this in real time, that is, in hours, minutes, seconds, milliseconds, nanoseconds, picoseconds, etc.

As used herein, "microarray" refers to a plurality of nucleic acid members stably associated with a substrate. The term "array" is used interchangeably with the term "microarray," however, the term "microarray" is used to define an array which has the additional property of being viewable microscopically.

As used herein, "viewable microscopically" refers to an object which can be placed on the stage of a dissecting or compound microscope and comprises at least a portion which can be viewed using an ocular of the microscope.

As used herein, "stably associated" refers to an association with a position on a substrate that does not change under nucleic acid hybridization and washing conditions.

BRIEF DESCRIPTION OF THE DRAWINGS

FIG. 1 presents the results of an MMLV-RT thermostability screen.

FIG. 2 presents the thermostability of His-tagged purified MMLV-RT point mutants.

FIG. 3 presents the thermostability of C-terminally extended mutants. HSRRRLKRHIFN=SEQ ID NO:64; SKRTNPINIHTNK=SEQ ID NO:65; QEGKNRQGEGQT=SEQ ID NO:66; RDRNKNNDRRKAKENE=SEQ ID NO:1; RDRNKNNDRRKAKRDRNKNNDRRKAK=SEQ ID NO:67; RDRNKNNDRRKAKENEENEENEENEENE=SEQ ID NO:68.

FIG. 4 presents the results of an activity assay for an RT comprising multiple mutations. RFGK=SEQ ID NO:37; RKFGK=SEQ ID NO:36.

FIG. 5 presents cDNA ladder synthesis by His-tagged RTs. RKFGK=SEQ ID NO:36.

FIG. 6 presents the thermostability of RTs of the invention. RDRNKNNDRRKAKENE=SEQ ID NO: 1.

DETAILED DESCRIPTION

Figure 7:
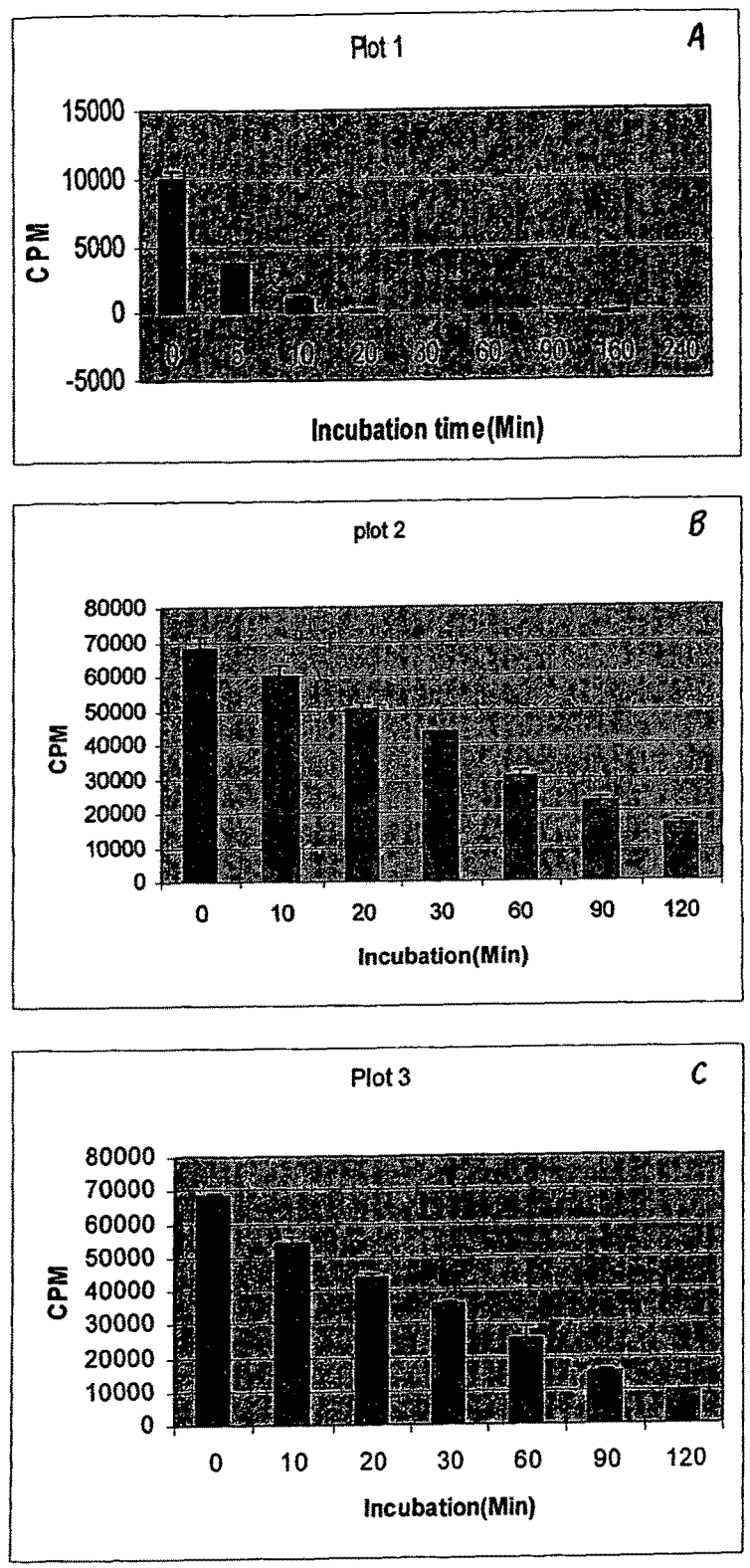

The invention relates to mutant reverse transcriptases (RTs). In one embodiment the mutant RTs exhibit increased stability, for example thermostability, as compared to a wild-type enzyme. The mutant RTs of the invention are useful for cDNA synthesis, cloning, production of cDNA libraries or microarrays and RT-PCR.

I. REVERSE TRANSCRIPTASES

One common approach to the study of gene expression is the production of complementary DNA (cDNA). Discovery of an RNA-dependent DNA polymerase, a so-called reverse transcriptase (RT), from a retrovirus has enabled a reverse transcription reaction in which a cDNA is synthesized using an RNA as a template. As a result of identifying RT, methods for analyzing mRNA molecules have made rapid progress. The methods for analyzing mRNA molecules using reverse transcriptase have now become indispensable experimental methods for studying gene expression and function. Subsequently, these methods, which have been applied to cloning and PCR techniques, have also become indispensable techniques in a wide variety of fields including biology, medicine and agriculture.

The invention relates to a reverse transcriptase (RT) selected from the group consisting of: Moloney Murine Leukemia Virus (M-MLV) RT, Human Immunodeficiency Virus (HIV) RT, Avian Sarcoma-Leukosis Virus (ASLV) RT, Rous Sarcoma Virus (RSV) RT, Avian Myeloblastosis Virus (AMV) RT, Avian Erythroblastosis Virus (AEV) Helper Virus MCAV RT, Avian Myelocytomatosis Virus MC29 Helper Virus MCAV RT, Avian Reticuloendotheliosis Virus (REV-T) Helper Virus REV-A RT, Avian Sarcoma Virus UR2 Helper Virus UR2AV RT, Avian Sarcoma Virus Y73 Helper Virus YAV RT, Rous Associated Virus (RAV) RT, and Myeloblastosis Associated Virus (MAV) RT.

Enzymes for use in the compositions, methods and kits of the present invention include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, E. coli DNA polymerase and klenow fragment, Tth DNA polymerase, Taq DNA polymerase (Saiki, R. K., et al., Science 239:487-491 (1988); U.S. Pat. Nos. 4,889,818 and 4,965,188), Tne DNA polymerase (WO 96/10640), Tma DNA polymerase (U.S. Pat. No. 5,374,553), C. Therm DNA polymerase from Carboxydothermus hydrogenoformans (EP0921196A1, Roche, Pleasanton, Calif., Cat. No. 2016338), ThermoScript (Invitrogen, Carsbad, Calif. Cat. No. 11731-015) and mutants, fragments, variants or derivatives thereof. As will be understood by one of ordinary skill in the art, modified reverse transcriptases may be obtained by recombinant or genetic engineering techniques that are routine and well-known in the art. Mutant reverse transcriptases can, for example, be obtained by mutating the gene or genes encoding the reverse transcriptase of interest by site-directed or random mutagenesis. Such mutations may include point mutations, deletion mutations and insertional mutations. Preferably, one or more point mutations (e.g., substitution of one or more amino acids with one or more different amino acids) are used to construct mutant reverse transcriptases of the invention. Fragments of reverse transcriptases may be obtained by deletion mutation by recombinant techniques that are routine and well-known in the art, or by enzymatic digestion of the reverse transcriptase(s) of interest using any of a number of well-known proteolytic enzymes. Mutant DNA polymerases containing reverse transcriptase activity, for example, as described in U.S. patent application Ser. No.

10/435,766, incorporated by reference in its entirety, are also useful according to the invention.

Polypeptides having reverse transcriptase activity that may be advantageously used in the present methods include, but are not limited to, Moloney Murine Leukemia Virus (M-MLV) reverse transcriptase, Rous Sarcoma Virus (RSV) reverse transcriptase, Avian Myeloblastosis Virus (AMV) reverse transcriptase, Rous-Associated Virus (RAV) reverse transcriptase, Myeloblastosis Associated Virus (MAV) reverse transcriptase, Human Immunodeficiency Virus (HIV) reverse transcriptase, Avian Sarcoma-Leukosis Virus (ASLV) reverse transcriptase, retroviral reverse transcriptase, retrotransposon reverse transcriptase, hepatitis B reverse transcriptase, cauliflower mosaic virus reverse transcriptase, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT®™) DNA polymerase, *Pyrococcus furiosus* (Pfu) DNA polymerase, DEEPVENT™. *Pyrococcus* species GB-D DNA polymerase, *Pyrococcus woesi* (Pwo) DNA polymerase, *Bacillus sterothermophilus* (Bst) DNA polymerase, *Bacillus caldophilus* (Bca) DNA polymerase, *Sulfoloblus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, and mutants, variants and derivatives thereof. The invention also encompasses bacterial DNA polymerases comprising residual reverse transcriptase activity, such as Taq DNA polymerase (for a description see, for example, Shadilya et al., 2004 Extremophiles, 8:243).

Particularly preferred for use in the invention are the variants of these enzymes that are reduced in RNase H activity (i.e., RNase H— enzymes). Preferably, the enzyme has less than 20%, more preferably less than 15%, 10% or 5%, and most preferably less than 2%, of the RNase H activity of a wildtype or "RNase H⁺" enzyme such as wildtype M-MLV reverse transcriptase. The RNase H activity of any enzyme may be determined by a variety of assays, such as those described, for example, in U.S. Pat. Nos. 5,244,797; 5,405,776; 5,668,005; and 6,063,608; in Kotewicz, M. L., et al., Nucl. Acids Res. 16:265 (1988) and in Gerard, G. F., et al., FOCUS 14(5):91 (1992), the disclosures of all of which are fully incorporated herein by reference.

Particularly preferred RNase H— reverse transcriptase enzymes for use in the invention include, but are not limited to, M-MLV H— reverse transcriptase, RSV H— reverse transcriptase, AMV H— reverse transcriptase, RAV H— reverse transcriptase, MAV H— reverse transcriptase and HIV H— reverse transcriptase for example as previously described (see U.S. Pat. Nos. 5,244,797; 5,405,776; 5,668,005 and 6,063,608; and WO 98/47912, the entirety of each is incorporated by reference). The RNase H activity of any enzyme may be determined by a variety of assays, such as those described, for example, in U.S. Pat. Nos. 5,244,797; 5,405,776; 5,668,005 and 6,063,608; in Kotewicz, M. L., et al., Nucl. Acids Res. 16:265 (1988); and in Gerard, G. F., et al., FOCUS 14(5):91 (1992), the disclosures of all of which are fully incorporated herein by reference. It will be understood by one of ordinary skill, however, that any enzyme capable of producing a DNA molecule from a ribonucleic acid molecule (i.e., having reverse transcriptase activity) that is substantially reduced in RNase H activity may be equivalently used in the compositions, methods and kits of the invention.

Polypeptides having reverse transcriptase activity for use in the invention may be obtained commercially, for example, from Invitrogen, Inc. (Carlsbad, Calif.), Pharmacia (Piscataway, N.J.), Sigma (Saint Louis, Mo.) or Roche Molecular System (Pleasanton, Calif.). Alternatively, polypeptides having reverse transcriptase activity may be isolated from their natural viral or bacterial sources according to standard procedures for isolating and purifying natural proteins that are well-known to one of ordinary skill in the art (see, e.g., Houts, G. E., et al., J. Virol. 29:517 (1979)). In addition, the polypeptides having reverse transcriptase activity may be prepared by recombinant DNA techniques that are familiar to one of ordinary skill in the art (see, e.g., Kotewicz, M. L., et al., Nucl. Acids Res. 16:265 (1988), Soltis, D. A., and Skalka, A. M., Proc. Natl. Acad. Sci. USA 85:3372-3376 (1988)). The entire teaching of the above references is hereby incorporated by reference.

Enzymes that are reduced in RNase H activity may be obtained by methods known in the art, e.g., by mutating the RNase H domain within the reverse transcriptase of interest, preferably by one or more point mutations, one or more deletion mutations, and/or one or more insertion mutations as described above, e.g., as described in U.S. Pat. No. 6,063,608 hereby incorporated in its entirety by reference.

Two or more enzymes with reverse transcriptase activity may be used in a single composition, e.g., the same reaction mixture. Enzymes used in this fashion may have distinct reverse transcription pause sites with respect to the template nucleic acid, as described in U.S. Patent Application 2003/0198944A1, hereby incorporated in its entirety by reference.

The enzyme containing reverse transcriptase activity of the present invention may also include a mutant or modified reverse transcriptase where one or more amino acid changes have been made which renders the enzyme more faithful (higher fidelity) in nucleic acid synthesis, e.g., as described in U.S. Patent Application 2003/0003452A1, hereby incorporated in its entirety by reference.

Epsilon Subunits

The invention provide for a reverse transcriptase of the invention in combination with a complex comprising the θ subunit of *E. coli* DNA polymerase III and the epsilon subunit of *E. coli* DNA polymerase III (e.g., see Hamdan et al., 2002, Biochemistry, 41:5266-5275). The θ subunit may also be used with any other mutant form of the epsilon subunit, for example the epsilon 186 truncated version of the epsilon subunit, to increase stability of the enzyme and/or to improve the accuracy, specificity and or processivity of the reverse transcriptases.

In one embodiment of the invention, a mutant reverse transcriptase is provided in combination with the θ epsilon subunit complex. Alternatively, a mutant reverse transcriptase is provided in combination with a complex comprising θ and a mutant form of the epsilon subunit, for example ε186

Denaturing Agents and Organic Solvents

The invention also provides for a reverse transcriptase in combination with a denaturing agent or organic solvent including but not limited to formamide and DMSO.

The invention also provides for a reverse transcriptase in combination with a PCR enhancing factor, for example, betaine.

II. GENETIC MODIFICATIONS—MUTAGENESIS

The preferred method of preparing a mutant reverse transcriptase is by genetic modification (e.g., by modifying the DNA sequence of a wild-type reverse transcriptase). A number of methods are known in the art that permit the random as well as targeted mutation of DNA sequences (see for example, Ausubel et. al. *Short Protocols in Molecular Biology* (1995) 3rd Ed. John Wiley & Sons, Inc.). In addition, there are a number of commercially available kits for site-directed mutagenesis, including both conventional and PCR-based methods. Examples include the GeneMorph Random mutagenesis kit (Stratagene Catalog No. 600550 or 200550), EXSITE™ PCR-Based Site-directed Mutagenesis Kit available from Stratagene (Catalog No. 200502) and the QUIKCHANGE™ Site-directed mutagenesis Kit from Stratagene (Catalog No. 200518), and the CHAMELEON® double-stranded Site-directed mutagenesis kit, also from Stratagene (Catalog No. 200509).

In addition mutant reverse transcriptases may be generated by insertional mutation or truncation (N-terminal, internal or C-terminal) according to methodology known to one skilled in the art.

Older methods of site-directed mutagenesis known in the art rely on sub-cloning of the sequence to be mutated into a vector, such as an M13 bacteriophage vector, that allows the isolation of single-stranded DNA template. In these methods, one anneals a mutagenic primer (i.e., a primer capable of annealing to the site to be mutated but bearing one or more mismatched nucleotides at the site to be mutated) to the single-stranded template and then polymerizes the complement of the template starting from the 3' end of the mutagenic primer. The resulting duplexes are then transformed into host bacteria and plaques are screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

Non-limiting examples for the isolation of mutant reverse transcriptases useful according to the invention are described in detail in Examples 1 and 2.

Methods of random mutagenesis, which will result in a panel of mutants bearing one or more randomly situated mutations, exist in the art. Such a panel of mutants may then be screened for those exhibiting the desired properties, for example, increased stability, relative to a wild-type reverse transcriptase. An example of a method for random mutagenesis is the so-called "error-prone PCR method". As the name implies, the method amplifies a given sequence under conditions in which the DNA polymerase does not support high fidelity incorporation. Although the conditions encouraging error-prone incorporation for different DNA polymerases vary, one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase.

Genes for desired mutant reverse transcriptases generated by mutagenesis may be sequenced to identify the sites and number of mutations. For those mutants comprising more than one mutation, the effect of a given mutation may be evaluated by introduction of the identified mutation to the wild-type gene by site-directed mutagenesis in isolation from the other mutations borne by the particular mutant. Screening assays of the single mutant thus produced will then allow the determination of the effect of that mutation alone.

The amino acid and DNA coding sequence of wild-type MMLV-reverse transcriptase are shown in FIG. 8. Non-limiting detailed procedures for preparing a mutant MMLV-reverse transcriptase useful according to the invention are provided in Examples 1 and 2.

A person of average skill in the art having the benefit of this disclosure will recognize that mutant reverse transcriptases polymerases derived from other reverse transcriptases, including but not limited to Moloney Murine Leukemia Virus (M-MLV); Human Immunodeficiency Virus (HIV) reverse transcriptase and avian Sarcoma-Leukosis Virus (ASLV) reverse transcriptase, which includes but is not limited to Rous Sarcoma Virus (RSV) reverse transcriptase, Avian Myeloblastosis Virus (AMV) reverse transcriptase, Avian Erythroblastosis Virus (AEV) Helper Virus MCAV reverse transcriptase, Avian Myelocytomatosis Virus MC29 Helper Virus MCAV reverse transcriptase, Avian Reticuloendotheliosis Virus (REV-T) Helper Virus REV-A reverse transcriptase, Avian Sarcoma Virus UR2 Helper Virus UR2AV reverse transcriptase, Avian Sarcoma Virus Y73 Helper Virus YAV reverse transcriptase, Rous Associated Virus (RAV) reverse transcriptase, and Myeloblastosis Associated Virus (MAV) reverse transcriptase may be suitably used in the subject compositions.

The enzyme of the subject composition may comprise reverse transcriptases that have not yet been isolated.

A method employing the addition of peptide tails with random sequences to the C-terminus of *Bacillus stearothermophilus* Catalase I, in an attempt to increase enzyme thermostability has been described (Matsuura et al., 1999 Nature Biotechnology 17:58). The invention contemplates mutant reverse transcriptases comprising a C-terminal extension As used herein, a "C-terminal extension" refers to a peptide tail of random sequence. A C-terminal extension is preferably from 1 to 500 amino acids, more preferably from 1 to 100 amino acids, and most preferably from 2 to 50 amino acids.

III. METHODS OF EVALUATING MUTANTS FOR INCREASED THERMOSTABILITY

Random or site-directed mutants generated as known in the art or as described herein and expressed in bacteria may be screened for RT activity and increased stability of RT activity by several different assays. Preferably, an RT enzyme is screened in an RT thermostability screen as described in Example 3, hereinbelow.

IV. EXPRESSION OF WILD-TYPE OR MUTANT ENZYMES ACCORDING TO THE INVENTION

Methods known in the art may be applied to express and isolate the mutated forms of reverse transcriptase according to the invention. The methods described here can be also applied for the expression of wild-type enzymes useful in the invention. Many bacterial expression vectors contain sequence elements or combinations of sequence elements allowing high level inducible expression of the protein encoded by a foreign sequence. For example, bacteria expressing an integrated inducible form of the T7 RNA polymerase gene may be transformed with an expression vector bearing a mutated DNA polymerase gene linked to the T7 promoter. Induction of the T7 RNA polymerase by addition of an appropriate inducer, for example, isopropyl-β-D-thiogalactopyranoside (IPTG) for a lac-inducible promoter, induces the high level expression of the mutated gene from the T7 promoter.

Appropriate host strains of bacteria may be selected from those available in the art by one of skill in the art. As a non-limiting example, *E. coli* strain BL-21 is commonly used for expression of exogenous proteins since it is protease deficient relative to other strains of *E. coli*. BL-21 strains bearing an inducible T7 RNA polymerase gene include WJ56 and ER2566 (Gardner & Jack, 1999, supra). For situations in which codon usage for the particular reverse transcriptase gene differs from that normally seen in *E. coli* genes, there are strains of BL-21 that are modified to carry tRNA genes encoding tRNAs with rarer anticodons (for example, argU, ileY, leuW, and proL tRNA genes), allowing high efficiency expression of cloned protein genes, for example, cloned archaeal enzyme genes (several BL21-CODON PLUS™ cell strains carrying rare-codon tRNAs are available from Stratagene, for example).

V. APPLICATIONS OF THE SUBJECT INVENTION cDNA Synthesis

In accordance with the invention, cDNA molecules (single-stranded or double-stranded) may be prepared from a variety of nucleic acid template molecules. Preferred nucleic acid molecules for use in the present invention include single-stranded or double-stranded DNA and RNA molecules, as well as double-stranded DNA:RNA hybrids. More preferred nucleic acid molecules include messenger RNA (mRNA), transfer RNA (tRNA) and ribosomal RNA (rRNA) molecules, although mRNA molecules are the preferred template according to the invention.

The invention provides compositions and methods for cDNA synthesis with increased specificity and accuracy. The present invention provides compositions and methods for high fidelity cDNA synthesis. The subject compositions and methods may also increase the efficiency of the reverse transcription as well as the length of the cDNA synthesized. As a result, the fidelity, efficiency, and yield of subsequent manipulations of the synthesized cDNA (e.g., amplification, sequencing, cloning, etc.) are also increased. The nucleic acid molecules that are used to prepare cDNA molecules according to the methods of the present invention may be prepared synthetically according to standard organic chemical synthesis methods that will be familiar to one of ordinary skill. More preferably, the nucleic acid molecules may be obtained from natural sources, such as a variety of cells, tissues, organs or organisms. Cells that may be used as sources of nucleic acid molecules may be prokaryotic (bacterial cells, including but not limited to those of species of the genera *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, Xanthomonas* and *Streptomyces*) or eukaryotic (including fungi (especially yeasts), plants, protozoans and other parasites, and animals including insects (particularly *Drosophila* spp. cells), nematodes (particularly *Caenorhabditis elegans* cells), and mammals (particularly human cells)).

Mammalian somatic cells that may be used as sources of nucleic acids include blood cells (reticulocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells). Mammalian germ cells (spermatocytes and oocytes) may also be used as sources of nucleic acids for use in the invention, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above prokaryotic or eukaryotic cells, tissues and organs may be normal, diseased, transformed, established, progenitors, precursors, fetal or embryonic. Diseased cells may, for example, include those involved in infectious diseases (caused by bacteria, fungi or yeast, viruses (including AIDS, HIV, HTLV, herpes, hepatitis and the like) or parasites), in genetic or biochemical pathologies (e.g., cystic fibrosis, hemophilia, Alzheimer's disease, muscular dystrophy or multiple sclerosis) or in cancerous processes. Transformed or established animal cell lines may include, for example, COS cells, CHO cells, VERO cells, BHK cells, HeLa cells, HepG2 cells, K562 cells, 293 cells, L929 cells, F9 cells, and the like. Other cells, cell lines, tissues, organs and organisms suitable as sources of nucleic acids for use in the present invention will be apparent to one of ordinary skill in the art.

Once the starting cells, tissues, organs or other samples are obtained, nucleic acid molecules (such as mRNA) may be isolated therefrom by methods that are well-known in the art (See, e.g., Maniatis, T., et al., Cell 15:687-701 (1978); Okayama, H., and Berg, P., Mol. Cell. Biol. 2:161-170 (1982); Gubler, U., and Hoffman, B. J., Gene 25:263-269 (1983)). The nucleic acid molecules thus isolated may then be used to prepare cDNA molecules and cDNA libraries in accordance with the present invention.

In the practice of the invention, cDNA molecules or cDNA libraries may be produced by mixing one or more nucleic acid molecules obtained as described above, which is preferably one or more mRNA molecules such as a population of mRNA molecules, with the composition of the invention, under conditions favoring the reverse transcription of the nucleic acid molecule by the action of the enzymes of the compositions to form a cDNA molecule (single-stranded or double-stranded). Thus, the method of the invention comprises (a) mixing one or more nucleic acid templates (preferably one or more RNA or mRNA templates, such as a population of mRNA molecules) with a mutant RT of the invention and (b) incubating the mixture under conditions sufficient to permit cDNA synthesis, e.g., to all or a portion of the one or more templates.

The compositions of the present invention may be used in conjunction with methods of cDNA synthesis such as those described in the Examples below, or others that are well-known in the art (see, e.g., Gubler, U., and Hoffman, B. J., Gene 25:263-269 (1983); Krug, M. S., and Berger, S. L., Meth. Enzymol. 152:316-325 (1987); Sambrook, J., et al., Molecular Cloning: A Laboratory Manual, 2nd ed., Cold Spring Harbor, N.Y.: Cold Spring Harbor Laboratory Press, pp. 8.60-8.63 (1989)), to produce cDNA molecules or libraries.

The invention is directed to such methods which further produce a first strand and a second strand cDNA, as known in the art. According to the invention, the first and second strand cDNAs produced by the methods may form a double stranded DNA molecule which may be a full length cDNA molecule.

Other methods of cDNA synthesis which may advantageously use the present invention will be readily apparent to one of ordinary skill in the art.

Subsequent Manipulation of Synthesized cDNA

Having obtained cDNA molecules or libraries according to the present methods, these cDNAs may be isolated or the reaction mixture containing the cDNAs may be directly used for further analysis or manipulation. Detailed methodologies for purification of cDNAs are taught in the GENETRAPPER™ manual (Invitrogen, Inc. Carlsbad, Calif.), which is incorporated herein by reference in its entirety, although alternative standard techniques of cDNA isolation such as those described in the Examples below or others that are known in the art (see, e.g., Sambrook, J., et al., Molecular Cloning: A Laboratory Manual, 2nd ed., Cold Spring Harbor, N.Y.: Cold Spring Harbor Laboratory Press, pp. 8.60-8.63 (1989)) may also be used.

In other aspects of the invention, the invention may be used in methods for amplifying nucleic acid molecules. Nucleic acid amplification methods according to this aspect of the invention may be one-step (e.g., one-step RT-PCR) or two-step (e.g., two-step RT-PCR) reactions. According to the invention, one-step RT-PCR type reactions may be accomplished in one tube thereby lowering the possibility of contamination. Such one-step reactions comprise (a) mixing a nucleic acid template (e.g., mRNA) with an enzyme of the present invention and (b) incubating the mixture under conditions sufficient to permit amplification. Two-step RT-PCR reactions may be accomplished in two separate steps. Such a method comprises (a) mixing a nucleic acid template (e.g., mRNA) with an enzyme of the present invention, (b) incubating the mixture under conditions sufficient to permit cDNA synthesis, (c) mixing the reaction mixture in (b) with one or more DNA polymerases and (d) incubating the mixture of step (c) under conditions sufficient to permit amplification. For amplification of long nucleic acid molecules (i.e., greater than about 3-5 Kb in length), a combination of DNA polymerases may be used, such as one DNA polymerase having 3'-5' exonuclease activity and another DNA polymerase being reduced in 3'-5' exonuclease activity.

Amplification methods which may be used in accordance with the present invention include PCR (e.g., U.S. Pat. Nos. 4,683,195 and 4,683,202), Strand Displacement Amplification (SDA; e.g., U.S. Pat. No. 5,455,166; EP 0 684 315), and Nucleic Acid Sequence-Based Amplification (NASBA; e.g., U.S. Pat. No. 5,409,818; EP 0 329 822). In a particularly preferred aspects, the invention may be used in methods of amplifying nucleic acid molecule comprising one or more polymerase chain reactions (PCRs), such as any of the PCR-based methods described above. All references are entirely incorporated by reference.

Various specific PCR amplification applications are available in the art (for reviews, see for example, Erlich, 1999, Rev Immunogenet., 1:127-34; Prediger 2001, Methods Mol. Biol. 160:49-63; Jurecic et al., 2000, Curr. Opin. Microbiol. 3:316-21; Triglia, 2000, Methods Mol. Biol. 130:79-83; MaClelland et al., 1994, PCR Methods Appl. 4:S66-81; Abramson and Myers, 1993, Current Opinion in Biotechnology 4:41-47; each of which is incorporated herein by references).

The subject invention can be used in PCR applications including, but not limited to, i) hot-start PCR which reduces non-specific amplification; ii) touch-down PCR which starts at high annealing temperature, then decreases annealing temperature in steps to reduce non-specific PCR product; iii) nested PCR which synthesizes more reliable product using an outer set of primers and an inner set of primers; iv) inverse PCR for amplification of regions flanking a known sequence. In this method, DNA is digested, the desired fragment is circularized by ligation, then PCR using primer complementary to the known sequence extending outwards; v) AP-PCR (arbitrary primed)/RAPD (random amplified polymorphic DNA). These methods create genomic fingerprints from species with little-known target sequences by amplifying using arbitrary oligonucleotides; vi) RT-PCR which uses RNA-directed DNA polymerase (e.g., reverse transcriptase) to synthesize cDNAs which is then used for PCR. This method is extremely sensitive for detecting the expression of a specific sequence in a tissue or cells. It may also be use to quantify mRNA transcripts; vii) RACE (rapid amplification of cDNA ends). This is used where information about DNA/protein sequence is limited. The method amplifies 3' or 5' ends of cDNAs generating fragments of cDNA with only one specific primer each (plus one adaptor primer). Overlapping RACE products can then be combined to produce full length cDNA; viii) DD-PCR (differential display PCR) which is used to identify differentially expressed genes in different tissues. The first step in DD-PCR involves RT-PCR, then amplification is performed using short, intentionally nonspecific primers; ix) Multiplex-PCR in which two or more unique targets of DNA sequences in the same specimen are amplified simultaneously. One DNA sequence can be used as control to verify the quality of PCR; x) Q/C-PCR (Quantitative comparative) which uses an internal control DNA sequence (but of different size) which competes with the target DNA (competitive PCR) for the same set of primers; xi) Recusive PCR which is used to synthesize genes. Oligonucleotides used in this method are complementary to stretches of a gene (>80 bases), alternately to the sense and to the antisense strands with ends overlapping (~20 bases); xii) Asymmetric PCR; xiii) In Situ PCR; xiv) Site-directed PCR Mutagenesis.

It should be understood that this invention is not limited to any particular amplification system. As other systems are developed, those systems may benefit by practice of this invention.

The primer used for synthesizing a cDNA from an RNA as a template in the present invention is not limited to a specific one as long as it is an oligonucleotide that has a nucleotide sequence complementary to that of the template RNA and that can anneal to the template RNA under reaction conditions used. The primer may be an oligonucleotide such as an oligo(dT) or an oligonucleotide having a random sequence (a random primer) or a gene-specific primer.

The nucleic acid molecules (e.g., synthesized cDNA or amplified product) or cDNA libraries prepared by the methods of the present invention may be further characterized, for example by cloning and sequencing (i.e., determining the nucleotide sequence of the nucleic acid molecule), by the sequencing methods of the invention or by others that are standard in the art (see, e.g., U.S. Pat. Nos. 4,962,022 and 5,498,523, which are directed to methods of DNA sequencing). Alternatively, these nucleic acid molecules may be used for the manufacture of various materials in industrial processes, such as hybridization probes by methods that are well-known in the art. Production of hybridization probes from cDNAs will, for example, provide the ability for those in the medical field to examine a patient's cells or tissues for the presence of a particular genetic marker such as a marker of cancer, of an infectious or genetic disease, or a marker of embryonic development. Furthermore, such hybridization probes can be used to isolate DNA fragments from genomic DNA or cDNA libraries prepared from a different cell, tissue or organism for further characterization.

It is understood that the amplified product produced using the subject enzyme can be cloned by any method known in the art. In one embodiment, the invention provides a composition which allows direct cloning of PCR amplified product.

The most common method for cloning PCR products involves incorporation of flanking restriction sites onto the ends of primer molecules. The PCR cycling is carried out and the amplified DNA is then purified, restricted with an appropriate endonuclease(s) and ligated to a compatible vector preparation.

A method for directly cloning PCR products eliminates the need for preparing primers having restriction recognition sequences and it would eliminate the need for a restriction step to prepare the PCR product for cloning. Additionally, such method would preferably allow cloning PCR products directly without an intervening purification step.

U.S. Pat. Nos. 5,827,657 and 5,487,993 (hereby incorporated by their entirety) disclose methods for direct cloning of PCR products using a DNA polymerase which takes advantage of the single 3'-deoxy-adenosine monophosphate (dAMP) residues attached to the 3' termini of PCR generated nucleic acids. Vectors are prepared with recognition sequences that afford single 3'-terminal deoxy-thymidine monophosphate (dTMP) residues upon reaction with a suitable restriction enzyme. Thus, PCR generated copies of genes can be directly cloned into the vectors without need for preparing primers having suitable restriction sites therein.

Taq DNA polymerase exhibits terminal transferase activity that adds a single dATP to the 3' ends of PCR products in the absence of template. This activity is the basis for the TA cloning method in which PCR products amplified with Taq are directly ligated into vectors containing single 3'dT overhangs. Pfu DNA polymerase, on the other hand, lacks terminal transferase activity, and thus produces blunt-ended PCR products that are efficiently cloned into blunt-ended vectors.

In one embodiment, the invention provides for a PCR product, generated in the presence of a mutant DNA polymerase with reduced uracil detection activity, that is subsequently incubated with Taq DNA polymerase in the presence of dATP at 72° C. for 15-30 minutes. Addition of 3'-dAMP to the ends of the amplified DNA product then permits cloning into TA cloning vectors according to methods that are well known to a person skilled in the art.

The nucleic acid molecules (e.g., synthesized cDNA or amplified product) of the present invention may also be used to prepare compositions for use in recombinant DNA methodologies. Accordingly, the present invention relates to recombinant vectors which comprise the cDNA or amplified nucleic acid molecules of the present invention, to host cells which are genetically engineered with the recombinant vectors, to methods for the production of a recombinant polypeptide using these vectors and host cells, and to recombinant polypeptides produced using these methods.

Recombinant vectors may be produced according to this aspect of the invention by inserting, using methods that are well-known in the art, one or more of the cDNA molecules or amplified nucleic acid molecules prepared according to the present methods into a vector. The vector used in this aspect of the invention may be, for example, a phage or a plasmid, and is preferably a plasmid. Preferred are vectors comprising cis-acting control regions to the nucleic acid encoding the polypeptide of interest. Appropriate trans-acting factors may be supplied by the host, supplied by a complementing vector or supplied by the vector itself upon introduction into the host.

In certain preferred embodiments in this regard, the vectors provide for specific expression (and are therefore termed "expression vectors"), which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids or bacteriophages, and vectors derived from combinations thereof, such as cosmids and phagemids, and will preferably include at least one selectable marker such as a tetracycline or ampicillin resistance gene for culturing in a bacterial host cell. Prior to insertion into such an expression vector, the cDNA or amplified nucleic acid molecules of the invention should be operatively linked to an appropriate promoter, such as the phage lambda $P_L$ promoter, the *E. coli* lac, trp and tac promoters. Other suitable promoters will be known to the skilled artisan.

Among vectors preferred for use in the present invention include pQE70, pQE60 and pQE-9, available from Qiagen; pBS vectors, Phagescript vectors, Bluescript vectors, pNH8A, pNH16a, pNH18A, pNH46A, available from Stratagene; pcDNA3 available from Invitrogen; pGEX, pTrxfus, pTrc99a, pET-S, pET-9, pKK223-3, pKK233-3, pDR540, pRIT5 available from Pharmacia; and pSPORT1, pSPORT2 and pSV.multidot.SPORT1, available from Life Technologies, Inc. Other suitable vectors will be readily apparent to the skilled artisan.

The invention also provides methods of producing a recombinant host cell comprising the cDNA molecules, amplified nucleic acid molecules or recombinant vectors of the invention, as well as host cells produced by such methods. Representative host cells (prokaryotic or eukaryotic) that may be produced according to the invention include, but are not limited to, bacterial cells, yeast cells, plant cells and animal cells. Preferred bacterial host cells include *Escherichia coli* cells (most particularly *E. coli* strains DH10B and Stbl2, which are available commercially (Life Technologies, Inc; Rockville, Md.)), *Bacillus subtilis* cells, *Bacillus megaterium* cells, *Streptomyces* spp. cells, *Erwinia* spp. cells, *Klebsiella* spp. cells and *Salmonella typhimurium* cells. Preferred animal host cells include insect cells (most particularly *Spodoptera frugiperda* SJ9 and Sf21 cells and Trichoplusa High-Five cells) and mammalian cells (most particularly CHO, COS, VERO, BHK and human cells). Such host cells may be prepared by well-known transformation, electroporation or transfection techniques that will be familiar to one of ordinary skill in the art.

In addition, the invention provides methods for producing a recombinant polypeptide, and polypeptides produced by these methods. According to this aspect of the invention, a recombinant polypeptide may be produced by culturing any of the above recombinant host cells under conditions favoring production of a polypeptide therefrom, and isolation of the polypeptide. Methods for culturing recombinant host cells, and for production and isolation of polypeptides therefrom, are well-known to one of ordinary skill in the art.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

VI. KITS

The present compositions may be assembled into kits for use in reverse transcription, cloning or amplification of a nucleic acid molecule. Kits according to this aspect of the invention comprise a carrier means, such as a box, carton, tube or the like, having in close confinement therein one or more container means, such as vials, tubes, ampules, bottles and the like. The kits of the invention may also comprise (in the same or separate containers) one or more reverse transcriptases, a suitable buffer, one or more nucleotides and/or one or more primers or any other reagents described for compositions of the present invention.

The kit of the present invention may include reagents facilitating the subsequent manipulation of cDNA synthesized as known in the art.

VII. EXAMPLES

Example 1. Generating RNase H Minus MMLV-RT Point Mutant Library for Thermostability Screen RNase H minus MMLV-RT (D524N) gene (2 kb) was mutagenized using the GeneMorph Random Mutagenesis Kit (Stratagene Catalog #200550 or 600550) and primers pSTRAT-F and pSTRAT-R (Table 2) according to the manufacturer's recommendations. Mutated PCR products "Mega primers" were used to replace the wild type RNase H minus MMLV-RT gene using the QuikChange Site-directed Mutagenesis Kit (Stratagene Catalog #200518) according to the manufacturer's recommendations. The resulting plasmids were cloned into XL-10 Gold competent cells (Stratagene Catalog #200317). The library size was $5 \times 10^4$ (containing 1-6 mutations/kb). DNA was extracted from the entire library using StrataPrep Plasmid Miniprep Kit (Stratagene Catalog #400761). A portion of the DNA was then transformed into BL21-DE3-RIL cells (Stratagene Catalog #230240) to generate a library with a size of $5 \times 10^4$.

Results:
The clones in this library contained 1-6 mutations/kb.

Example 2. Generating RNase H Minus MMLV-RT Random C-Terminal Extension Library for Thermostability Screen Primers RTSSC12AXhoI and RTSSEI-vecF (Table 2) were used to amplify RNase H minus MMLV-RT gene using Herculase DNA polymerase (Stratagene Catalog #600260). The PCR products were then digested with EcoRI and XhoI and cloned into pCal-n-FLAG (Stratagene Catalog #214311) that is missing the Calmodulin binding unit and the FLAG sequence. The resulting C-terminal extension library was cloned into XL-10 Gold competent cells (Stratagene Catalog #200317). DNA was extracted from the entire library using StrataPrep Plasmid Miniprep Kit (Stratagene Catalog #400761) and transformed into BL21-DE3-RIL cells (Stratagene Catalog #230240).

Results:
The library size was $10^4$. From 17 clones sequenced, 12 had 7-14 amino acid additions, 2 had 1-2 amino acid additions, 1 had 18 amino acid additions, 1 had 30 amino acid additions, and one had no additions.

Example 3. RT Thermostability Screen Assay

Mutant colonies from the BL21-DE3-RIL libraries (both point mutant and C-terminal extension libraries) were inoculated into 120 µl LB media containing 100 µg/ml Ampicillin and 35 µg/ml Chloramphenicol (Costar 96 well plate (29444-102)) and grown over night at 37° C. 10 µl of these cultures were inoculated into 110 µl LB media containing 100 µg/ml Ampicillin, 35 µg/ml Chloramphenicol, and 1 mM IPTG (Costar 96 well plate (29444-102)) and grown overnight. Cells were lysed using 30 µl lysis buffer (125 mM Tris pH 8, 4.5% glucose, 50 mM EDTA, 2.5% Triton, 5 mg/ml lysozyme, and 50 mM DTT). 10 µl of lysates were used in a 50 µl assay containing 50 mM Tris pH 8.3, 75 mM KCl, 8 mM $MgCl_2$, 2 µg poly(rC), 0.5 µg oligo(dG), 10 mM DTT, 50 mM dGTP, and 0.5 µCi $\alpha^{33}$pdGTP. Reactions were incubated at 42° C. or 55° C. for 60 minutes (FIG. 1). 4 µl of these reactions were spotted on DE-81 filters, and dried. The filters were then washed 5 times with 2×SSC and dried. The filters were then exposed to Kodak BioMax MR-1 films (VWR IB8941114)) over night.

Results:
3400 clones from the point mutation library were screened using the thermostability assay described above. The mutants that showed higher activity at 55° C. compared to the WT enzyme (FIG. 1) were selected and re-screened using the same RT activity assay three more times. The best mutants were selected, sequenced, and His-tag purified (as in example 6). Mutations E69K, L435M, N454K, and M651L were discovered and their RT activity at 52° C./42° C. (as in example 4) were compared to the WT enzyme (FIG. 2). All His-tagged purified mutants showed higher activity at 52° C./42° C. compared to the WT enzyme.

4000 clones from the C-terminal extension library were also screened using the thermostability assay described above. The mutants that showed higher activity at 55° C. compared to the WT enzyme were selected and re-screened using the same RT activity assay three more times. The best mutants were selected, sequenced, and His-tag purified (as in example 6). Multiple peptide tails increased the activity of RT at 52° C./42° C. (assayed as in example 4) compared to the WT enzyme (FIG. 3).

Example 4. RT Activity Assay

The RNA dependent DNA polymerization assays for His-tagged purified WT and mutants were performed as follows. ~5 units of each enzyme (equivalent amount of protein on a SDS-PAGE gel) were used in a 50 µl assay containing 50 mM Tris pH 8.3, 75 mM KCl, 8 mM $MgCl_2$, 2 µg poly(rC), 0.5 µg oligo(dG), 10 mM DTT, 50 mM dGTP, and 0.5 µCi $\alpha^{33}$pdGTP. Reactions were incubated at 42° C. or 52° C. for 30 minutes. 5 µl of these reactions were spotted on DE-81 filters, and dried. The filters were then washed 5 times with 2×SSC, followed by a brief wash with 100% ethanol. The filters were then dried. Incorporated radioactivity was measured by scintillation counting. Reactions that lacked enzyme were set up along with sample incubations to determine "total cpms" (omit filter wash steps) and "minimum cpms" (wash filters as above). Minimum cpms were subtracted from sample cpms to determine "corrected cpms".

Example 5. Saturation Mutagenesis at Putative "Thermostability" Residues to Identify Best Mutation at Each Site Independently Saturation mutagenesis was performed using QuikChange Site-directed Mutagenesis Kit (Stratagene Catalog #200518) and primers containing degenerate site (NNG/T) at E69, E302, F303, G305, W313, L435, N454, M651 (Table 2) according to the manufacturer's recommendations. 200 clones from every library were screened (as in example 3). The mutants with the highest activity at 55° C. were selected, and sequenced.
Results:
The following mutations show the highest activity at 55° C.: E69K, E302K, E302R, W313F, L435M, L435G, N454K, N454R, M651L Example 6. Combination of Thermostable Mutations The QuikChange Multi Site-directed Mutagenesis Kit (Stratagene Catalog #200514) with four primers (Table 2) was used to introduce the mutations E69K, W313F, L435G, and N454K into an RNase H minus MMLV-RT gene that already contained the E302R mutation. Ten clones were sequenced.
Results: The following combinations were obtained:

```
Clone 1:
E302R/E69K/W313F/L435G/N454K   RKFGK  (SEQ ID NO: 36)

Clone 2:
E302R/W313F/L435G/N454K        RFGK   (SEQ ID NO: 37)

Clone 3:
E302R/W313F/L435G              RFG

Clone 4:
E302R/E69K/N454K               RKK

Clone 5:
E302R/W313F                    RF
```

Activity assays (as in example 3—using DE-81 filters and poly(rC):oligo(dG)$_{18}$) (SEQ ID NO:62) were performed at 42° C. and 57° C. and the results (FIG. 4) indicate higher activity at 57° C. for clones containing single or multiple mutations as compared to the wild type enzyme.

Example 7. Activity Assay Using Poly(A) RNA Ladder

Full length cDNA profiling was performed for WT RT versus RKFGK (SEQ ID NO:36) mutant RT (His-tagged proteins) using a poly(A)-tailed RNA ladder (Ambion #7150). Reactions contained 2 µg RNA ladder, 0.5 µg oligo(dT)$_{18}$ (SEQ ID NO:63), 3.2 mM dNTPs and ~100 units of enzyme (equivalent protein amount on a SDS-PAGE gel) in 1× Stratascript buffer containing 3 or 6 mM Mg$^{2+}$. Reactions were incubated at 42° C., 50° C., and 52° C. for 60 minutes, run on a 1% alkaline agarose gel and stained with SYBR Gold.
Results:
RKFGK (SEQ ID NO: 36) mutant RT generates longer cDNA ladders at higher temperature (52° C.) compared to the WT enzyme (FIG. 5).

Example 8. Purification and Thermostability Comparison of Final Constructs

Three His tagged constructs including RNase H minus MMLV-RT (D524N), RNase H minus MMLV-RT (D524N, E302R, E69K,W313F,L435G,N454K), and RNase H minus MMLV-RT (D524N,E302R, E69K,W313F,L435G,N454K) plus the C-terminal extension (RDRNKNNDRRKAKENE) (SEQ ID NO: 1) were expressed and purified according to the QIAexpressionist (Qiagen). An RT activity assay using Poly(rC):poly(dG) was performed similar to as in Example 4.
Results:
The RNase H minus MMLV-RT (D524N,E302R, E69K, W313F,L435G,N454K) with the C-terminal extension (RDRNKNNDRRKAKENE) (SEQ ID NO: 1) shows the highest activity at 55° C. and 60° C. (FIG. 6).

Example 9. Half Life Determination

Half-lives of mutant reverse transcriptase enzymes of the invention were determined as follows.
Three non-His tagged constructs including RNase H minus MMLV-RT (D524N) (FIG. 7A, plot 1), RNase H minus MMLV-RT (D524N, E302R, E69K, W313F, L435G, N454K) (FIG. 7B, plot 2), and RNase H minus MMLV-RT (D524N, E302R, E69K, W313F, L435G, N454K) plus the C-terminal extension (RDRNKNNDRRKAKENE) (SEQ ID NO: 1) (FIG. 7C, plot 3) were assayed as follows. Mixtures containing 0.5 pmol of each enzyme in the presence of 2 µg poly(rC), 0.5 µg oligo(dG)$_{18}$ (SEQ ID NO:62) were incubated at 55° C. for various times as indicated in the plots. Incubation was stopped by placing the tubes on ice. An aliquot was assayed for residual activity in 50 mM Tris pH 8.3, 75 mM KCl, 3 mM MgCl$_2$, 10 mM DTT, 50 mM dGTP, and 0.5 µCi α$^{33}$ pdGTP. Reactions were incubated at 42° C. for 30 minutes. 5 µl of these reactions were spotted on DE-81 filters, and dried. The filters were then washed 5 times with 2×SSC, followed by a brief wash with 100% ethanol. The filters were then dried. Incorporated radioactivity was measured by scintillation counting. Reactions that lacked enzyme were set up along with sample incubations to determine "total cpms" (omit filter wash steps) and "minimum cpms" (wash filters as above). Minimum cpms were subtracted from sample cpms to determine "corrected cpms".
Results:
The half life of RNase H minus MMLV-RT (D524N) (FIG. 7A, plot 1) is <5 minutes where the half life of RNase H minus MMLV-RT (D524N, E302R, E69K,W313F, L435G,N454K) (FIG. 7B, plot 2) is >30 minutes, and the half life of RNase H minus MMLV-RT (D524N,E302R, E69K,W313F,L435G,N454K) plus the C-terminal extension (RDRNKNNDRRKAKENE) (SEQ ID NO: 1) (FIG. 7C, plot 3) if 30 minutes at 55° C.

TABLE 1

Primer sequences pSTRAT-F: (SEQ ID NO: 38)
5'-ACCCTAAATATAGAAGATGAGCATCG pSTRAT-R: (SEQ ID NO: 39)
5'-GAGGAGGGTAGAGGTGTCTGGAGTC RTSSC12AXhoI: (SEQ ID NO. 40)
5'-CTTGGCCAAGGATCCGCTCGAGCTACTTACTTANNNNNNNNNNNNN
NNNNNNNNNNNNNNNNNNNNNNNGAGGAGGGTAGAGGTGTCTGGAGTCT RTSSEI-vecF: (SEQ ID NO: 41)
5'-AGCGGATAACAATTCCCCTCTAGAATTCGA pE69X-F: (SEQ ID NO: 42)
5'-CCCATGTCACAANNKGCCAGACTGGG
K = G or T pE302X-F: (SEQ ID NO: 43)
5'-GACAACTAAGGNNKTTCCTAGGGACG pF303X-F: (SEQ ID NO: 44)
5'-CAACTAAGGGAGNNKCTAGGGACGGC pG305X-F: (SEQ ID NO: 45)
5'-GGAGTTCCTANNKACGGCAGGCTTC pW313X-F: (SEQ ID NO: 46)
5'-TCTGTCGCCTCNNKATCCCTGGGTTTG pL435X-F: (SEQ ID NO: 47)
5'-CCACTAGTCATTNNKGCCCCCCATGCAG pN454X-F: (SEQ ID NO: 48)
5'-GCTGGCTTTCCNNKGCCCGGATGACTC pM651X-F: (SEQ ID NO: 49)
5'-GAGGCAACCGGNNKGCTGACCAAGCG pE69X-R: (SEQ ID NO: 50)
5'-CCCAGTCTGGCMNNTTGTGACATGGG
M = A or C

TABLE 1-continued

Primer sequences pE302X-R: (SEQ ID NO: 51)
5'-CGTCCCTAGGAAMNNCCTTAGTTGTC pF303X-R: (SEQ ID NO: 52)
5'-GCCGTCCCTAGMNNCTCCCTTAGTTG pG305X-R: (SEQ ID NO: 53)
5'-GAAGCCTGCCGTMNNTAGGAACTCC pW313X-R: (SEQ ID NO: 54)
5'-CAAACCCAGGGATMNNGAGGCGACAGA pL435X-R: (SEQ ID NO: 55)
5'-CTGCATGGGGGGCMNNAATGACTAGTGG pN454X-R: (SEQ ID NO: 56)
5'-GAGTCATCCGGGCMNNGGAAAGCCAGC pM651X-R: (SEQ ID NO: 57)
5'-CGCTTGGTCAGCMNNCCGGTTGCCTC pE69K: (SEQ ID NO: 58)
5'-TACCCCATGTCACAAAAAGCCAGACTGGGGATCAAG pW313F: (SEQ ID NO: 59)
5'-GGCTTCTGTCGCCTCTTTATCCCTGGGTTTGC pL435G: (SEQ ID NO: 60)
5'-CAGCCACTAGTCATTGGGGCCCCCCATGCAGTAG pN454K: (SEQ ID NO: 61)
5'-GACCGCTGGCTTTCCAAGGCCCGGATGACTCAC All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated mutant Moloney Murine Leukemia Virus (MMLV) reverse transcriptase having increased reverse transcriptase activity comprising the sequence of SEQ ID NO: 19 with the exception of a mutation at at least one of the following amino acid positions: E69, E302, W313, L435, N454, and M651,
   wherein the mutant MMLV reverse transcriptase comprises at least one of the following mutations:
   a glutamic acid to lysine mutation at position E69,
   a glutamic acid to lysine mutation at position E302,
   a glutamic acid to arginine mutation at position E302,
   a tryptophan to phenylalanine mutation at position W313,
   a leucine to glycine mutation at position L435,
   a leucine to methionine mutation at position L435,
   an asparagine to lysine mutation at position N454,
   an asparagine to arginine mutation at position N454, and
   a methionine to leucine mutation at position M651.

2. The mutant MMLV reverse transcriptase of claim 1, comprising at least two of said mutations.

3. An isolated mutant MMLV reverse transcriptase having reverse transcriptase activity comprising the sequence of SEQ ID NO:19 with the exception that the sequence has a combination of mutations selected from the following groups of combinations of mutations: E302R or K/E69K/W313F/L435G or M/N454K or R; E302R or K/W313F/L435G or M/N454K or R; E302R or K/W313F/L435G or M; E302R or K/E69K/N454K or R; E302R or K/W313F; and E69K/E302R or K/W313F/L435G or M/N454K or R/D524N.

4. The mutant MMLV reverse transcriptase of claim 1, further comprising a C-terminal extension.

5. The mutant MMLV reverse transcriptase of claim 4, wherein said C-terminal extension is RDRNKNNDRRKAKENE (SEQ ID NO:1).

6. The mutant MMLV reverse transcriptase of claim 1, wherein said reverse transcriptase lacks RNase H activity.

7. The mutant MMLV reverse transcriptase of claim 1, wherein the reverse transcriptase has at least one of the following characteristics: increased stability, increased accuracy, increased processivity, and increased specificity.

8. An isolated polynucleotide comprising a nucleotide sequence encoding a mutant MMLV reverse transcriptase of claim 1.

9. The isolated polynucleotide of claim 8, wherein the mutant MMLV reverse transcriptase comprises at least two of said mutations.

10. An isolated polynucleotide comprising a nucleotide sequence encoding a mutant MMLV reverse transcriptase of claim 3.

11. The isolated polynucleotide of claim 8, further encoding a C-terminal extension.

12. The isolated polynucleotide of claim 11, wherein said C-terminal extension is RDRNKNNDRRKAKENE.

13. A composition comprising an isolated mutant MMLV reverse transcriptase having increased reverse transcriptase activity comprising the sequence of SEQ ID NO: 19, with the exception that at least one of the following amino acid positions comprises a mutation: E69, E302, W313, L435, N454, and M651,
   wherein the mutant MMLV reverse transcriptase comprises at least one of the following mutations:
   a glutamic acid to lysine mutation at position E69,
   a glutamic acid to lysine mutation at position E302,
   a glutamic acid to arginine mutation at position E302,
   a tryptophan to phenylalanine mutation at position W313,
   a leucine to glycine mutation at position L435,
   a leucine to methionine mutation at position L435,
   an asparagine to lysine mutation at position N454,
   an asparagine to arginine mutation at position N454, and
   a methionine to leucine mutation at position M651.

14. The composition of claim 13, wherein the mutant MMLV reverse transcriptase comprises at least two of said mutations.

15. A composition comprising an isolated mutant MMLV reverse transcriptase having reverse transcriptase activity and comprising the sequence of SEQ ID NO:19 with the exception that the sequence has a combination of mutations selected from the following groups of combinations of mutations: E302R or K/E69K/W313F/L435G or M/N454K or R; E302R or K/W313F/L435G or M/N454K or R; E302R or K/W313F/L435G or M; E302R or K/E69K/N454K or R; E302R or K/W313F; and E69K/E302R or K/W313F/L435G or M/N454K or R/D524N.

16. The composition of claim 13, wherein the reverse transcriptase further comprises a C-terminal extension.

17. The composition of claim 16, wherein said C-terminal extension is RDRNKNNDRRKAKENE (SEQ ID NO:1).

18. The composition of claim of claim 13, wherein the reverse transcriptase has at least one of the following characteristics: increased stability, increased accuracy, increased processivity, and increased specificity.

19. The composition of claim 13, wherein said reverse transcriptase lacks RNase H activity.

20. The composition of claim 13, further comprising an epsilon subunit from an eubacteria.

21. The composition of claim 20, wherein said epsilon subunit is from *Eschericia coli*.

22. The composition of claim 20, wherein said epsilon subunit is epsilon 186 from *Eschericia coli*.

23. The composition of claim 13, further comprising formamide, betaine, or dimethyl sulfoxide (DMSO).

24. A kit comprising
an isolated mutant MMLV reverse transcriptase having increased reverse transcriptase activity and comprising the sequence of SEQ ID NO: 19 with the exception of a mutation at at least one of the following amino acid positions: E69, E302, W313, L435, N454, and M651, wherein the mutant MMLV reverse transcriptase comprises at least one of the following mutations:
a glutamic acid to lysine mutation at position E69,
a glutamic acid to lysine mutation at position E302,
a glutamic acid to arginine mutation at position E302,
a tryptophan to phenylalanine mutation at position W313,
a leucine to glycine mutation at position L435,
a leucine to methionine mutation at position L435,
an asparagine to lysine mutation at position N454,
an asparagine to arginine mutation at position N454, and
a methionine to leucine mutation at position M651.

25. The kit of claim 24, wherein the mutant MMLV reverse transcriptase comprises at least two of said mutations.

26. A kit comprising
an isolated mutant MMLV reverse transcriptase having reverse transcriptase activity and comprising the sequence of SEQ ID NO:19 with the exception that the sequence has a combination of mutations selected from the following groups of combinations of mutations: E302R or K/E69K/W313F/L435G or M/N454K or R; E302R or K/W313F/L435G or M/N454K or R; E302R or K/W313F/L435G or M; E302R or K/E69K/N454K or R; E302R or K/W313F; and E69K/E302R or K/W313F/L435G or M/N454K or R/D524N, and packaging materials therefor.

27. The kit of claim 24, wherein said reverse transcriptase lacks RNase H activity.

28. The kit of claim 24, wherein said mutant MMLV reverse transcriptase further comprises a C-terminal extension.

29. The kit of claim 28, wherein said C-terminal extension is RDRNKNNDRRKAKENE (SEQ ID NO:1).

30. The kit of claim 24, wherein said reverse transcriptase has at least one of the following characteristics: increased stability, increased accuracy, increased processivity, and increased specificity.

31. The kit of claim 24, further comprising an epsilon subunit from an eubacteria.

32. The kit of claim 31, wherein said epsilon subunit is from *Eschericia coli*.

33. The kit of claim 31, wherein said epsilon subunit is epsilon 186 from *Eschericia coli*.

34. The kit of claim 24, further comprising formamide, betaine, or DMSO.

35. A method for complementary deoxyribonucleic acid (cDNA) synthesis comprising:
(a) providing a mutant reverse transcriptase of claim 1; and
(b) contacting said mutant reverse transcriptase with a nucleic acid template to permit cDNA synthesis.

36. A method for cloning comprising:
(a) providing a mutant reverse transcriptase of claim 1; and
(b) contacting said mutant reverse transcriptase with a nucleic acid template to generate a synthesized cDNA product and
(c) inserting said synthesized cDNA product into a cloning vector.

37. A method for reverse transcription-polymerase chain reaction (RT-PCR) comprising:
(a) providing a mutant reverse transcriptase of claim 1; and
(b) contacting said mutant reverse transcriptase with a nucleic acid template to replicate and amplify said nucleic acid template.

38. The method of claim 37, wherein said RT-PCR comprises end-point RT-PCR.

39. The method of claim 37, wherein said RT-PCR is performed in real-time.

40. A method for cDNA library construction comprising:
(a) providing a mutant reverse transcriptase of claim 1; and
(b) contacting said mutant reverse transcriptase with a nucleic acid template to generate a synthesized cDNA product and
(c) inserting said synthesized cDNA product into a vector.

41. A method for preparing a microarray comprising:
(a) providing a mutant reverse transcriptase of claim 1; and
(b) contacting said mutant reverse transcriptase with a nucleic acid template to generate a synthesized cDNA product and
(c) attaching said cDNA product to a substrate.

* * * * *

UNITED STATES PATENT AND TRADEMARK OFFICE
CERTIFICATE OF CORRECTION

PATENT NO.       : 9,783,791 B2
APPLICATION NO.  : 11/502819
DATED            : October 10, 2017
INVENTOR(S)      : Holly Hogrefe et al.

It is certified that error appears in the above-identified patent and that said Letters Patent is hereby corrected as shown below:

In the Specification

In Column 4, Line 63, delete "Eschericia" and insert -- Escherichia --, therefor.

In Column 4, Line 65, delete "Eschericia" and insert -- Escherichia --, therefor.

In Column 5, Line 37, delete "Eschericia" and insert -- Escherichia --, therefor.

In Column 5, Line 39, delete "Eschericia" and insert -- Escherichia --, therefor.

In Column 6, Line 36, delete "UR2Helper" and insert -- UR2 Helper --, therefor.

In Column 11, Line 26, delete "an" and insert -- and --, therefor.

In Column 16, Line 67, delete "procaryotic" and insert -- prokaryotic --, therefor.

In Column 17, Line 6-7, delete "Lactobaccilus," and insert -- Lactobacillus, --, therefor.

In Column 19, Line 63, above "DETAILED DESCRIPTION" insert -- FIG. 7 presents the half-life of mutant RTs according to the invention. --.

In Column 20, Line 48, delete "Carsbad," and insert -- Carlsbad, --, therefor.

In Column 21, Line 17, delete "neopolitana" and insert -- neapolitana --, therefor.

In Column 21, Line 19, delete "VENT®™)" and insert -- VENT®) --, therefor.

In Column 21, Line 21, delete "woesi" and insert -- woesei --, therefor.

In Column 21, Line 22, delete "sterothermophilus" and insert -- stearothermophilus --, therefor.

Signed and Sealed this
Twenty-first Day of November, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,783,791 B2

In Column 21, Line 23-24, delete "Sulfoloblus" and insert -- Sulfolobus --, therefor.

In Column 22, Line 14, delete "(1988)," and insert -- (1988); --, therefor.

In Column 22, Line 47, delete "and or" and insert -- and/or --, therefor.

In Column 28, Line 27, delete "use" and insert -- used --, therefor.

In Column 28, Line 44, delete "Recusive" and insert -- Recursive --, therefor.

In Column 30, Line 41, delete "pET-S," and insert -- pET-5, --, therefor.

In Column 30, Line 61, delete "Trichoplusa" and insert -- Trichoplusia --, therefor.

In Column 32, Line 25, delete "overnight." and insert -- over night. --, therefor.

In Column 33, Line 67, delete "Stratascript" and insert -- StrataScript --, therefor.

In Column 34, Lines 15-16, delete "(D524N,E302R, E69K,W313F,L435G,N454K)," and insert -- (D524N, E302R, E69K, W313F, L435G, N454K), --, therefor.

In Column 34, Line 17, delete "E69K,W313F,L435G,N454K)" and insert -- E69K, W313F, L435G, N454K) --, therefor.

In Column 34, Line 20, delete "QLA" and insert -- QIA --, therefor.

In Column 34, Lines 24-25, delete "(D524N,E302R, E69K,W313F,L435G,N454K)" and insert -- (D524N, E302R, E69K, W313F, L435G, N454K) --, therefor.

In Column 34, Lines 62-63, delete "E69K,W313F,L435G,N454K)" and insert -- E69K, W313F, L435G, N454K) --, therefor.

In Column 34, Lines 64-65, delete "(D524N,E302R, E69K,W313F,L435G,N454K)" and insert -- (D524N, E302R, E69K, W313F, L435G, N454K) --, therefor.

In the Claims

In Column 147, Line 19, in Claim 18, delete "of claim of claim" and insert -- of claim --, therefor.

In Column 147, Line 28, in Claim 21, delete "Eschericia" and insert -- Escherichia --, therefor.

In Column 147, Line 30, in Claim 22, delete "Eschericia" and insert -- Escherichia --, therefor.

In Column 148, Line 17, in Claim 32, delete "Eschericia" and insert -- Escherichia --, therefor.

In Column 148, Line 19, in Claim 33, delete "Eschericia" and insert -- Escherichia --, therefor.

SEQUENCE LISTING

<160> NUMBER OF SEQ ID NOS: 70

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Arg Asp Arg Asn Lys Asn Asn Asp Arg Arg Lys Ala Lys Glu Asn Glu
1               5                   10                  15

<210> SEQ ID NO 2
<211> LENGTH: 2013
<212> TYPE: DNA
<213> ORGANISM: Moloney murine leukemia virus

<400> SEQUENCE: 2

```
accctaaata tagaagatga gcatcggcta catgagacct caaaagagcc agatgtttct      60
ctagggtcca catggctgtc tgattttcct caggcctggg cggaaaccgg gggcatggga     120
ctggcagttc gccaagctcc tctgatcata cctctgaaag caacctctac ccccgtgtcc     180
ataaaacaat accccatgtc acaagaagcc agactgggga tcaagcccca catacagaga     240
ctgttggacc agggaatact ggtaccctgc cagtccccct ggaacacgcc cctgctaccc     300
gttaagaaac cagggactaa tgattatagg cctgtccagg atctgagaga agtcaacaag     360
cgggtggaag acatccaccc caccgtgccc aaccctacac acctcttgag cgggctccca     420
ccgtcccacc agtggtacac tgtgcttgat ttaaaggatg cctttttctg cctgagactc     480
caccccacca gtcagcctct cttcgccttt gagtggagag atccagagat gggaatctca     540
ggacaattga cctggaccag actcccacag ggtttcaaaa acagtcccac cctgtttgat     600
gaggcactgc acagagacct agcagacttc cggatccagc acccagactt gatcctgcta     660
cagtacgtgg atgacttact gctggccgcc acttctgagc tagactgcca acaaggtact     720
cgggccctgt tacaaaccct agggaacctc gggtatcggg cctcggccaa gaaagcccaa     780
atttgccaga acaggtcaa gtatctgggg tatcttctaa aagagggtca gagatggctg     840
actgaggcca gaaaagagac tgtgatgggg cagcctactc cgaagacccc tcgacaacta     900
agggagttcc tagggacggc aggcttctgt cgcctctgga tccctgggtt tgcagaaatg     960
gcagcccctc tgtaccctct caccaaaacg gggactctgt ttaattgggg cccagaccaa    1020
caaaaggcct atcaagaaat caagcaagct cttctaactg cccagcccct ggggttgcca    1080
gatttgacta gccctttga actctttgtc gacgagaagc agggctacgc caaaggtgtc    1140
ctaacgcaaa aactgggacc ttggcgtcgg ccggtggcct acctgtccaa aaagctagac    1200
ccagtagcag ctgggtggcc cccttgccta cggatggtag cagccattgc cgtactgaca    1260
aaggatgcag gcaagctaac catgggacag ccactagtca ttctggccccc ccatgcagta    1320
gaggcactag tcaaacaacc ccccgaccgc tggcttttcca acgcccggat gactcactat    1380
caggccttgc ttttggacac ggaccgggtc cagttcggac cggtggtagc cctgaacccg    1440
gctacgctgc tcccactgcc tgaggaaggg ctgcaacaca actgccttga tatcctggcc    1500
gaagcccacg gaacccgacc cgacctaacg gaccagccgc tcccagacgc cgaccacacc    1560
tggtacacgg atggaagcag tctcttacaa gagggacagc gtaaggcggg agctgcggtg    1620
accaccgaga ccgaggtaat ctgggctaaa gccctgccag ccgggacatc cgctcagcgg    1680
gctgaactga tagcactcac ccaggcccta aagatggcag aaggtaagaa gctaaatgtt    1740
tatactgata gccgttatgc ttttgctact gcccatatcc atggagaaat atacagaagg    1800
cgtgggttgc tcacatcaga aggcaaagag atcaaaaata agacgagat cttggcccta    1860
ctaaaagccc tctttctgcc caaaagactt agcataatcc attgtccagg acatcaaaag    1920
ggacacagcg ccgaggctag aggcaaccgg atggctgacc aagcggcccg aaaggcagcc    1980
atcacagaga ctccagacac ctctaccctc ctc                                 2013
```

<210> SEQ ID NO 3
<211> LENGTH: 2013
<212> TYPE: DNA

<213> ORGANISM: Moloney murine leukemia virus
<220> FEATURE:
<221> NAME/KEY: modified_base
<222> LOCATION: (205)..(207)
<223> OTHER INFORMATION: This region may encompass 'aaa' or 'aag'

<400> SEQUENCE: 3

| | | | | | |
|---|---|---|---|---|---|
| accctaaaata | tagaagatga | gcatcggcta | catgagacct | caaaagagcc | agatgtttct | 60 |
| ctagggtcca | catggctgtc | tgattttcct | caggcctggg | cggaaaccgg | gggcatggga | 120 |
| ctggcagttc | gccaagctcc | tctgatcata | cctctgaaag | caacctctac | ccccgtgtcc | 180 |
| ataaaacaat | accccatgtc | acaannngcc | agactgggga | tcaagcccca | catacagaga | 240 |
| ctgttggacc | agggaatact | ggtaccctgc | cagtccccct | ggaacacgcc | cctgctaccc | 300 |
| gttaagaaac | cagggactaa | tgattatagg | cctgtccagg | atctgagaga | agtcaacaag | 360 |
| cgggtggaag | acatccaccc | caccgtgccc | aaccettaca | acctcttgag | cgggctccca | 420 |
| ccgtcccacc | agtggtacac | tgtgcttgat | ttaaaggatg | ccttttttctg | cctgagactc | 480 |
| caccccacca | gtcagcctct | cttcgccttt | gagtggagag | atccagagat | gggaatctca | 540 |
| ggacaattga | cctggaccag | actcccacag | ggtttcaaaa | acagtcccac | cctgtttgat | 600 |
| gaggcactgc | acagagacct | agcagacttc | cggatccagc | acccagactt | gatcctgcta | 660 |
| cagtacgtgg | atgacttact | gctggccgcc | acttctgagc | tagactgcca | acaaggtact | 720 |
| cgggccctgt | tacaaaccct | agggaacctc | gggtatcggg | cctcggccaa | gaaagcccaa | 780 |
| atttgccaga | aacaggtcaa | gtatctgggg | tatcttctaa | agaggggtca | gagatggctg | 840 |
| actgaggcca | gaaaagagac | tgtgatgggg | cagcctactc | cgaagacccc | tcgacaacta | 900 |
| agggagttcc | tagggacggc | aggcttctgt | cgcctctgga | tccctgggtt | tgcagaaatg | 960 |
| gcagcccct | tgtaccctct | caccaaaacg | gggactctgt | ttaattgggg | cccagaccaa | 1020 |
| caaaaggcct | atcaagaaat | caagcaagct | cttctaactg | ccccagccct | ggggttgcca | 1080 |
| gatttgacta | gcccctttga | actctttgtc | gacgagaagc | agggctacgc | caaaggtgtc | 1140 |
| ctaacgcaaa | aactgggacc | ttggcgtcgg | ccggtggcct | acctgtccaa | aaagctagac | 1200 |
| ccagtagcag | ctgggtggcc | cccttgccta | cggatggtag | cagccattgc | cgtactgaca | 1260 |
| aaggatgcag | gcaagctaac | catgggacag | ccactagtca | ttctggcccc | ccatgcagta | 1320 |
| gaggcactag | tcaaacaacc | ccccgaccgc | tggctttcca | acgcccggat | gactcactat | 1380 |
| caggccttgc | ttttggacac | ggaccgggtc | cagttcggac | cggtggtagc | cctgaacccg | 1440 |
| gctacgctgc | tcccactgcc | tgaggaaggg | ctgcaacaca | actgccttga | tatcctggcc | 1500 |
| gaagcccacg | gaacccgacc | cgacctaacg | gaccagccgc | tcccagacgc | cgaccacacc | 1560 |
| tggtacacgg | atggaagcag | tctcttacaa | gagggacagc | gtaaggcggg | agctgcggtg | 1620 |
| accaccgaga | ccgaggtaat | ctgggctaaa | gccctgccag | ccgggacatc | cgctcagcgg | 1680 |
| gctgaactga | tagcactcac | ccaggcccta | aagatggcag | aaggtaagaa | gctaaatgtt | 1740 |
| tatactgata | gccgttatgc | ttttgctact | gcccatatcc | atggagaaat | atacagaagg | 1800 |
| cgtgggttgc | tcacatcaga | aggcaaagag | atcaaaaata | agacgagat | cttggcccta | 1860 |
| ctaaaagccc | tctttctgcc | caaaagactt | agcataatcc | attgtccagg | acatcaaaag | 1920 |
| ggacacagcg | ccgaggctag | aggcaaccgg | atggctgacc | aagcggcccg | aaaggcagcc | 1980 |
| atcacagaga | ctccagacac | ctctaccctc | ctc | | | 2013 |

<210> SEQ ID NO 4
<211> LENGTH: 2013

<212> TYPE: DNA
<213> ORGANISM: Moloney murine leukemia virus
<220> FEATURE:
<221> NAME/KEY: modified_base
<222> LOCATION: (904)..(906)
<223> OTHER INFORMATION: This region may encompass 'aaa' or 'aag'

<400> SEQUENCE: 4

```
accctaaata tagaagatga gcatcggcta catgagacct caaaagagcc agatgtttct    60
ctagggtcca catggctgtc tgattttcct caggcctggg cggaaaccgg gggcatggga   120
ctggcagttc gccaagctcc tctgatcata cctctgaaag caacctctac ccccgtgtcc   180
ataaaacaat accccatgtc acaagaagcc agactgggga tcaagcccca catacagaga   240
ctgttggacc agggaatact ggtaccctgc cagtccccct ggaacacgcc cctgctaccc   300
gttaagaaac cagggactaa tgattatagg cctgtccagg atctgagaga agtcaacaag   360
cgggtggaag acatccaccc caccgtgccc aacccttaca acctcttgag cgggctccca   420
ccgtcccacc agtggtacac tgtgcttgat ttaaaggatg ccttttttctg cctgagactc   480
caccccacca gtcagcctct cttcgccttt gagtggagag atccagagat gggaatctca   540
ggacaattga cctggaccag actcccacag ggtttcaaaa acagtcccac cctgtttgat   600
gaggcactgc acagagacct agcagacttc cggatccagc acccagactt gatcctgcta   660
cagtacgtgg atgacttact gctggccgcc acttctgagc tagactgcca acaaggtact   720
cgggccctgt tacaaaccct agggaacctc gggtatcggg cctcggccaa gaaagcccaa   780
atttgccaga aacaggtcaa gtatctgggg tatcttctaa aagagggtca gagatggctg   840
actgaggcca gaaaagagac tgtgatgggg cagcctactc cgaagacccc tcgacaacta   900
aggnnnttcc tagggacggc aggcttctgt cgcctctgga tccctgggtt tgcagaaatg   960
gcagccccct tgtaccctct caccaaaacg gggactctgt ttaattgggg cccagaccaa  1020
caaaaggcct atcaagaaat caagcaagct cttctaactg ccccagccct ggggttgcca  1080
gatttgacta agccctttga actctttgtc gacgagaagc agggctacgc caaaggtgtc  1140
ctaacgcaaa aactgggacc ttggcgtcgg ccggtggcct acctgtccaa aaagctagac  1200
ccagtagcag ctgggtggcc ccttgcctca cggatggtag cagccattgc cgtactgaca  1260
aaggatgcag gcaagctaac catgggacag ccactagtca ttctggcccc ccatgcagta  1320
gaggcactag tcaaacaacc ccccgaccgc tggctttcca acgcccggat gactcactat  1380
caggccttgc tttttggacac ggaccgggtc cagttcggac cggtggtagc cctgaacccg  1440
gctacgctgc tcccactgcc tgaggaaggg ctgcaacaca actgccttga tatcctggcc  1500
gaagcccacg gaacccgacc cgacctaacg gaccagccgc tcccagacgc cgaccacacc  1560
tggtacacga tggaagcag tctcttacaa gagggacagg gtaaggcggg agctgcggtg  1620
accaccgaga ccgaggtaat ctgggctaaa gccctgccag ccgggacatc cgctcagcgg  1680
gctgaactga tagcactcac ccaggcccta aagatggcag aagtaagaa gctaaatgtt  1740
tatactgata gccgttatgc ttttgctact gcccatatcc atggagaaat atacagaagg  1800
cgtgggttgc tcacatcaga aggcaaagag atcaaaaata agacgagat cttggcccta  1860
ctaaaagccc tctttctgcc caaaagactt agcataatcc attgtccagg acatcaaaag  1920
ggacacagcg ccgaggctag aggcaaccgg atggctgacc aagcggcccg aaaggcagcc  1980
atcacagaga ctccagacac ctctaccctc ctc                              2013
```

<210> SEQ ID NO 5

<211> LENGTH: 2013
<212> TYPE: DNA
<213> ORGANISM: Moloney murine leukemia virus
<220> FEATURE:
<221> NAME/KEY: modified_base
<222> LOCATION: (904)..(906)
<223> OTHER INFORMATION: This region may encompass 'cgt', 'cgc', 'cga', 'cgg', 'aga' or 'agg'

<400> SEQUENCE: 5

```
accctaaata tagaagatga gcatcggcta catgagacct caaaagagcc agatgtttct      60
ctagggtcca catggctgtc tgattttcct caggcctggg cggaaaccgg gggcatggga     120
ctggcagttc gccaagctcc tctgatcata cctctgaaag caacctctac ccccgtgtcc     180
ataaaacaat accccatgtc acaagaagcc agactgggga tcaagcccca catacagaga     240
ctgttggacc agggaatact ggtaccctgc cagtccccct ggaacacgcc cctgctaccc     300
gttaagaaac cagggactaa tgattatagg cctgtccagg atctgagaga agtcaacaag     360
cgggtggaag acatccaccc caccgtgccc aacccttaca acctcttgag cgggctccca     420
ccgtcccacc agtggtacac tgtgcttgat ttaaaggatg cctttttctg cctgagactc     480
caccccacca gtcagcctct cttcgccttt gagtggagag atccagagat gggaatctca     540
ggacaattga cctggaccag actcccacag ggtttcaaaa acagtcccac cctgtttgat     600
gaggcactgc acagagacct agcagacttc cggatccagc acccagactt gatcctgcta     660
cagtacgtgg atgacttact gctggccgcc acttctgagc tagactgcca acaaggtact     720
cgggccctgt tacaaaccct agggaacctc gggtatcggg cctcggccaa gaaagcccaa     780
atttgccaga aacaggtcaa gtatctgggg tatcttctaa agagggtcac gagatggctg     840
actgaggcca gaaagagac tgtgatgggg cagcctactc cgaagacccc tcgacaacta     900
aggnnnttcc tagggacggc aggcttctgt cgcctctgga tccctgggtt tgcagaaatg     960
gcagccccct tgtaccctct caccaaaacg gggactctgt ttaattgggg cccagaccaa    1020
caaaaggcct atcaagaaat caagcaagct cttctaactg ccccagccct ggggttgcca    1080
gatttgacta agcccttgga actctttgtc gacgagaagc agggctacgc caaaggtgtc    1140
ctaacgcaaa aactgggacc ttggcgtcgg ccggtgcct acctgtccaa aaagctagac    1200
ccagtagcag ctgggtggcc cccttgccta cggatggtag cagccattgc cgtactgaca    1260
aaggatgcag gcaagctaac catgggacag ccactagtca ttctggccc ccatgcagta    1320
gaggcactag tcaaacaacc ccccgaccgc tggctttcca acgcccggat gactcactat    1380
caggccttgc ttttggacac ggaccgggtc cagttcggac cggtggtagc cctgaacccg    1440
gctacgctgc tcccactgcc tgaggaaggg ctgcaacaca actgccttga tatcctggcc    1500
gaagcccacg gaacccgacc cgacctaacg gaccagccgc tcccagacgc cgaccacacc    1560
tggtacacgg atggaagcag tctcttacaa gagggacagc gtaaggcggg agctgcggtg    1620
accaccgaga ccgaggtaat ctgggctaaa gccctgccag ccgggacatc cgctcagcgg    1680
gctgaactga tagcactcac ccaggcccta aagatggcag aaggtaagaa gctaaatgtt    1740
tatactgata gccgttatgc ttttgctact gcccatatcc atggagaaat atacagaagg    1800
cgtgggttgc tcacatcaga aggcaaagag atcaaaaata agacgagat cttggcccta    1860
ctaaaagccc tctttctgcc caaaagactt agcataatcc attgtccagg acatcaaaag    1920
ggacacagcg ccgaggctag aggcaaccgg atggctgacc aagcggcccg aaaggcagcc    1980
atcacagaga ctccagacac ctctaccctc ctc                                 2013
```

<210> SEQ ID NO 6
<211> LENGTH: 2013
<212> TYPE: DNA
<213> ORGANISM: Moloney murine leukemia virus
<220> FEATURE:
<221> NAME/KEY: modified_base
<222> LOCATION: (937)..(939)
<223> OTHER INFORMATION: This region may encompass 'ttt' or 'ttc'

<400> SEQUENCE: 6

```
accctaaaata tagaagatga gcatcggcta catgagacct caaaagagcc agatgtttct      60
ctagggtcca catggctgtc tgattttcct caggcctggg cggaaaccgg ggcatggga       120
ctggcagttc gccaagctcc tctgatcata cctctgaaag caacctctac ccccgtgtcc     180
ataaaacaat accccatgtc acaagaagcc agactgggga tcaagcccca catacagaga     240
ctgttggacc agggaatact ggtaccctgc cagtccccct ggaacacgcc cctgctaccc     300
gttaagaaac cagggactaa tgattatagg cctgtccagg atctgagaga agtcaacaag     360
cgggtggaag acatccaccc caccgtgccc aaccctttaca acctcttgag cgggctccca     420
ccgtcccacc agtggtacac tgtgcttgat ttaaaggatg cctttttctg cctgagactc     480
caccccacca gtcagcctct cttcgccttt gagtggagag atccagagat gggaatctca     540
ggacaattga cctggaccag actcccacag ggtttcaaaa acagtcccac cctgtttgat     600
gaggcactgc acagagacct agcagacttc cggatccagc acccagactt gatcctgcta     660
cagtacgtgg atgacttact gctggccgcc acttctgagc tagactgcca acaaggtact     720
cgggccctgt tacaaaccct agggaacctc gggtatcggg cctcggccaa gaaagcccaa     780
atttgccaga aacaggtcaa gtatctgggg tatcttctaa aagagggtca gagatggctg     840
actgaggcca gaaaagagac tgtgatgggg cagcctactc cgaagacccc tcgacaacta     900
agggagttcc tagggacggc aggcttctgt cgcctcnnna tccctgggtt tgcagaaatg     960
gcagcccct tgtaccctct caccaaaacg gggactctgt ttaattgggg cccagaccaa    1020
caaaaggcct atcaagaaat caagcaagct cttctaactg ccccagccct ggggttgcca    1080
gatttgacta gcccctttga actctttgtc gacgagaagc agggctacgc caaaggtgtc    1140
ctaacgcaaa aactgggacc ttggcgtcgg ccggtggcct acctgtccaa aaagctagac    1200
ccagtagcag ctgggtggcc ccttgcccta cggatggtag cagccattgc cgtactgaca    1260
aaggatgcag gcaagctaac catgggacag ccactagtca ttctggcccc ccatgcagta    1320
gaggcactag tcaaacaacc ccccgaccgc tggctttcca acgcccggat gactcactat    1380
caggccttgc ttttggacac ggaccgggtc cagttcggac cggtggtagc cctgaacccg    1440
gctacgctgc tcccactgcc tgaggaaggg ctgcaacaca actgccttga tatcctggcc    1500
gaagcccacg gaacccgacc cgacctaacg gaccagccgc tcccagacgc cgaccacacc    1560
tggtacacgg atggaagcag tctcttacaa gagggacagc gtaaggcggg agctgcggtg    1620
accaccgaga ccgaggtaat ctgggctaaa gccctgccag ccgggacatc cgctcagcgg    1680
gctgaactga tagcactcac ccaggcccta aagatggcag aaggtaagaa gctaaatgtt    1740
tatactgata gccgttatgc ttttgctact gcccatatcc atggagaaat atacagaagg    1800
cgtgggttgc tcacatcaga aggcaaagag atcaaaaata aagacgagat cttggcccta    1860
ctaaaagccc tctttctgcc caaaagactt agcataatcc attgtccagg acatcaaaag    1920
ggacacagcg ccgaggctag aggcaaccgg atggctgacc aagcggcccg aaaggcagcc    1980
atcacagaga ctccagacac ctctaccctc ctc                                 2013
```

```
<210> SEQ ID NO 7
<211> LENGTH: 2013
<212> TYPE: DNA
<213> ORGANISM: Moloney murine leukemia virus
<220> FEATURE:
<221> NAME/KEY: modified_base
<222> LOCATION: (1303)..(1305)
<223> OTHER INFORMATION: This region may encompass 'ggt', 'ggc', 'gga'
      or 'ggg'

<400> SEQUENCE: 7
accctaaata tagaagatga gcatcggcta catgagacct caaaagagcc agatgtttct      60
ctagggtcca catggctgtc tgattttcct caggcctggg cggaaaccgg gggcatggga     120
ctggcagttc gccaagctcc tctgatcata cctctgaaag caacctctac ccccgtgtcc     180
ataaaacaat accccatgtc acaagaagcc agactgggga tcaagcccca catacagaga     240
ctgttggacc agggaatact ggtaccctgc cagtccccct ggaacacgcc cctgctaccc     300
gttaagaaac cagggactaa tgattatagg cctgtccagg atctgagaga agtcaacaag     360
cgggtggaag acatccaccc caccgtgccc aacccttaca acctcttgag cgggctccca     420
ccgtcccacc agtggtacac tgtgcttgat ttaaaggatg ccttttttctg cctgagactc     480
caccccacca gtcagcctct cttcgccttt gagtggagag atccagagat gggaatctca     540
ggacaattga cctggaccag actcccacag ggtttcaaaa acagtccac cctgtttgat     600
gaggcactgc acagagacct agcagacttc cggatccagc acccagactt gatcctgcta     660
cagtacgtgg atgacttact gctggccgcc acttctgagc tagactgcca acaaggtact     720
cgggccctgt acaaaccct agggaacctc gggtatcggg cctcggccaa gaaagcccaa     780
atttgccaga acaggtcaa gtatctgggg tatcttctaa agagggtca gagatggctg     840
actgaggcca gaaaagagac tgtgatgggg cagcctactc gaagaccccc tcgacaacta     900
agggagttcc tagggacggc aggcttctgt cgcctctgga tccctgggtt tgcagaaatg     960
gcagccccct tgtaccctct caccaaaacg gggactctgt ttaattgggg cccagaccaa    1020
caaaaggcct atcaagaaat caagcaagct cttctaactg ccccagccct ggggttgcca    1080
gatttgacta agcccttga actctttgtc gacgagaagc agggctacgc caaaggtgtc    1140
ctaacgcaaa aactgggacc ttggcgtcgg ccggtggcct acctgtccaa aaagctagac    1200
ccagtagcag ctgggtggcc cccttgccta cggatggtag cagccattgc cgtactgaca    1260
aaggatgcag gcaagctaac catgggacag ccactagtca ttnnngcccc ccatgcagta    1320
gaggcactag tcaaacaacc ccccgaccgc tggctttcca acgcccggat gactcactat    1380
caggccttgc ttttggacac ggaccgggtc cagttcggac cggtggtagc cctgaacccg    1440
gctacgctgc tcccactgcc tgaggaaggg ctgcaacaca actgccttga tatcctggcc    1500
gaagcccacg gaacccgacc cgacctaacg gaccagccgc tcccagacgc cgaccacacc    1560
tggtacacgg atggaagcag tctcttacaa gagggacagg taaggcggg agctgcggtg    1620
accaccgaga ccgaggtaat ctgggctaaa gccctgccag ccgggacatc cgctcagcgg    1680
gctgaactga tagcactcac ccaggcccta aagatgcag aaggtaagaa gctaaatgtt    1740
tatactgata gccgttatgc ttttgctact gcccatatcc atggagaaat atacagaagg    1800
cgtgggttgc tcacatcaga aggcaaagag atcaaaaata agacgagat cttggcccta    1860
ctaaaagccc tctttctgcc caaaagactt agcataatcc attgtccagg acatcaaaag    1920
ggacacagcg ccgaggctag aggcaaccgg atggctgacc aagcggcccg aaaggcagcc    1980
```

```
atcacagaga ctccagacac ctctaccctc ctc                          2013

<210> SEQ ID NO 8
<211> LENGTH: 2013
<212> TYPE: DNA
<213> ORGANISM: Moloney murine leukemia virus

<400> SEQUENCE: 8
accctaaata tagaagatga gcatcggcta catgagacct caaaagagcc agatgtttct    60
ctagggtcca catggctgtc tgattttcct caggcctggg cggaaaccgg gggcatggga   120
ctggcagttc gccaagctcc tctgatcata cctctgaaag caacctctac ccccgtgtcc   180
ataaaacaat accccatgtc acaagaagcc agactgggga tcaagcccca catacagaga   240
ctgttggacc agggaatact ggtaccctgc cagtcccect ggaacacgcc cctgctaccc   300
gttaagaaac cagggactaa tgattatagg cctgtccagg atctgagaga agtcaacaag   360
cgggtggaag acatccaccc caccgtgccc aaccct taca acctcttgag cgggctccca   420
ccgtcccacc agtggtacac tgtgcttgat ttaaaggatg cctttttctg cctgagactc   480
caccccacca gtcagcctct cttcgccttt gagtggagag atccagagat gggaatctca   540
ggacaattga cctggaccag actcccacag ggtttcaaaa acagtcccac cctgtttgat   600
gaggcactgc acagagacct agcagacttc cggatccagc acccagactt gatcctgcta   660
cagtacgtgg atgacttact gctggccgcc acttctgagc tagactgcca acaaggtact   720
cgggccctgt tacaaaccct agggaacctc gggtatcggg cctcggccaa gaaagcccaa   780
atttgccaga aacaggtcaa gtatctgggg tatcttctaa aagagggtca gagatggctg   840
actgaggcca gaaaagagac tgtgatgggg cagcctactc cgaagacccc tcgacaacta   900
agggagttcc tagggacggc aggcttctgt cgcctctgga tccctgggtt tgcagaaatg   960
gcagccccct tgtaccctct caccaaaacg gggactctgt ttaattgggg cccagaccaa  1020
caaaaggcct atcaagaaat caagcaagct cttctaactg ccccagccct ggggttgcca  1080
gatttgacta agcccttga actctttgtc gacgagaagc agggctacgc caaaggtgtc  1140
ctaacgcaaa aactgggacc ttggcgtcgg ccggtggcct acctgtccaa aaagctagac  1200
ccagtagcag ctgggtggcc cccttgccta cggatggtag cagccattgc cgtactgaca  1260
aaggatgcag gcaagctaac catgggacag ccactagtca ttatgccccc ccatgcagta  1320
gaggcactag tcaaacaacc ccccgaccgc tggctttcca acgcccggat gactcactat  1380
caggccttgc ttttggacac ggaccgggtc cagttcggac cggtggtagc cctgaacccg  1440
gctacgctgc tcccactgcc tgaggaaggg ctgcaacaca actgccttga tatcctggcc  1500
gaagcccacg gaaccccgacc cgacctaacg gaccagccgc tcccagacgc cgaccacacc  1560
tggtacacgg atggaagcag tctcttacaa gagggacagc gtaaggcggg agctgcggtg  1620
accaccgaga ccgaggtaat ctgggctaaa gccctgccag ccgggacatc cgctcagcgg  1680
gctgaactga tagcactcac ccaggccota aagatggcag aaggtaagaa gctaaatgtt  1740
tatactgata gccgttatgc ttttgctact gcccatatcc atggagaaat atacagaagg  1800
cgtgggttgc tcacatcaga aggcaaagag atcaaaaata agacgagat cttggcccta  1860
ctaaaagccc tcttctctgcc caaaagactt agcataatcc attgtccagg acatcaaaag  1920
ggacacagcg ccgaggctag aggcaaccgg atggctgacc aagcggcccg aaaggcagcc  1980
atcacagaga ctccagacac ctctaccctc ctc                              2013
```

<210> SEQ ID NO 9
<211> LENGTH: 2013
<212> TYPE: DNA
<213> ORGANISM: Moloney murine leukemia virus
<220> FEATURE:
<221> NAME/KEY: modified_base
<222> LOCATION: (1360)..(1362)
<223> OTHER INFORMATION: This region may encompass 'aaa' or 'aag'

<400> SEQUENCE: 9

```
accctaaaata tagaagatga gcatcggcta catgagacct caaaagagcc agatgtttct      60
ctagggtcca catggctgtc tgattttcct caggcctggg cggaaaccgg gggcatggga     120
ctggcagttc gccaagctcc tctgatcata cctctgaaag caacctctac ccccgtgtcc     180
ataaaacaat accccatgtc acaagaagcc agactgggga tcaagcccca catacagaga     240
ctgttggacc agggaatact ggtaccctgc cagtccccct ggaacacgcc cctgctaccc     300
gttaagaaac cagggactaa tgattatagg cctgtccagg atctgagaga agtcaacaag     360
cgggtggaag acatccaccc caccgtgccc aaccccttaca acctcttgag cgggctccca     420
ccgtcccacc agtggtacac tgtgcttgat ttaaaggatg ccttttttctg cctgagactc     480
caccccacca gtcagcctct cttcgccttt gagtggagag atccagagat gggaatctca     540
ggacaattga cctggaccag actcccacag ggtttcaaaa acagtcccac cctgtttgat     600
gaggcactgc acagagacct agcagacttc cggatccagc acccagactt gatcctgcta     660
cagtacgtgg atgacttact gctggccgcc acttctgagc tagactgcca acaaggtact     720
cgggccctgt tacaaaccct agggaacctc gggtatcggg cctcggccaa gaaagcccaa     780
atttgccaga acaggtcaa gtatctgggg tatcttctaa agagggtca gagatggctg     840
actgaggcca gaaagagac tgtgatgggg cagcctactc cgaagacccc tcgacaacta     900
agggagttcc tagggacggc aggcttctgt cgcctctgga tccctgggtt tgcagaaatg     960
gcagccccct tgtaccctct caccaaaacg gggactctgt ttaattgggg cccagaccaa    1020
caaaaggcct atcaagaaat caagcaagct cttctaactg ccccagccct ggggttgcca    1080
gatttgacta gcccctttga actctttgtc gacgagaagc agggctacgc caaaggtgtc    1140
ctaacgcaaa aactgggacc ttggcgtcgg ccggtggcct acctgtccaa aaagctagac    1200
ccagtagcag ctgggtggcc ccttgcccta ggatggtag cagccattgc cgtactgaca    1260
aaggatgcag gcaagctaac catgggacag ccactagtca ttctggcccc ccatgcagta    1320
gaggcactag tcaaacaacc ccccgaccgc tggctttccn nngcccggat gactcactat    1380
caggccttgc ttttggacac ggaccgggtc cagttcggac cggtggtagc cctgaacccg    1440
gctacgctgc tcccactgcc tgaggaaggg ctgcaacaca actgccttga tatcctggcc    1500
gaagcccacg gaacccgacc cgacctaacg gaccagccgc tcccagacgc cgaccacacc    1560
tggtacacgg atggaagcag tctcttacaa gagggacagc gtaaggcggg agctgcggtg    1620
accaccgaga ccgaggtaat ctgggctaaa gccctgccag ccgggacatc cgctcagcgg    1680
gctgaactga tagcactcac ccaggcccta aagatggcag aaggtaagaa gctaaatgtt    1740
tatactgata gccgttatgc ttttgctact gcccatatcc atggagaaat atacagaagg    1800
cgtgggttgc tcacatcaga aggcaaagag atcaaaaata agacgagat cttggcccta    1860
ctaaaagccc tctttctgcc caaaagactt agcataatcc attgtccagg acatcaaaag    1920
ggacacagcg ccgaggctag aggcaaccgg atggctgacc aagcggcccg aaaggcagcc    1980
atcacagaga ctccagacac ctctaccctc ctc                                 2013
```

<210> SEQ ID NO 10
<211> LENGTH: 2013
<212> TYPE: DNA
<213> ORGANISM: Moloney murine leukemia virus
<220> FEATURE:
<221> NAME/KEY: modified_base
<222> LOCATION: (1360)..(1362)
<223> OTHER INFORMATION: This region may encompass 'cgt', 'cgc', 'cga', 'cgg', 'aga' or 'agg'

<400> SEQUENCE: 10

```
accctaaata tagaagatga gcatcggcta catgagacct caaaagagcc agatgtttct      60
ctagggtcca catggctgtc tgattttcct caggcctggg cggaaaccgg gggcatggga     120
ctggcagttc gccaagctcc tctgatcata cctctgaaag caacctctac ccccgtgtcc     180
ataaaacaat accccatgtc acaagaagcc agactgggga tcaagcccca catacagaga     240
ctgttggacc agggaatact ggtaccctgc cagtccccct ggaacacgcc cctgctaccc     300
gttaagaaac cagggactaa tgattatagg cctgtccagg atctgagaga agtcaacaag     360
cgggtggaag acatccaccc caccgtgccc aaccctttaca acctcttgag cgggctccca     420
ccgtcccacc agtggtacac tgtgcttgat ttaaaggatg ccttttttctg cctgagactc     480
cacccccacca gtcagcctct cttcgccttt gagtggagag atccagagat gggaatctca     540
ggacaattga cctggaccag actcccacag ggtttcaaaa acagtcccac cctgtttgat     600
gaggcactgc acagagacct agcagacttc cggatccagc acccagactt gatcctgcta     660
cagtacgtgg atgacttact gctggccgcc acttctgagc tagactgcca acaaggtact     720
cgggccctgt acaaaccct agggaacctc gggtatcggg cctcggccaa gaaagcccaa     780
atttgccaga aacaggtcaa gtatctgggg tatcttctaa aagagggtca gagatggctg     840
actgaggcca gaaaagagac tgtgatgggg cagcctactc cgaagacccc tcgacaacta     900
agggagttcc tagggacggc aggcttctgt cgcctctgga tccctgggtt tgcagaaatg     960
gcagccccct tgtaccctct caccaaaacg gggactctgt ttaattgggg cccagaccaa    1020
caaaaggcct atcaagaaat caagcaagct cttctaactg ccccagcccct ggggttgcca    1080
gatttgacta agcccttgga actctttgtc gacgagaagc agggctacgc caaaggtgtc    1140
ctaacgcaaa aactgggacc ttggcgtcgg ccggtggcct acctgtccaa aaagctagac    1200
ccagtagcag ctgggtggcc cccttgccta cggatggtag cagccattgc cgtactgaca    1260
aaggatgcag gcaagctaac catgggacag ccactagtca ttctggcccc ccatgcagta    1320
gaggcactag tcaaacaacc ccccgaccgc tggctttccn nngcccggat gactcactat    1380
caggccttgc ttttggacac ggaccgggtc cagttcggac cggtggtagc cctgaacccg    1440
gctacgctgc tcccactgcc tgaggaaggg ctgcaacaca actgccttga tatcctggcc    1500
gaagcccacg gaacccgacc cgacctaacg gaccagccgc tcccagacgc cgaccacacc    1560
tggtacacgg atggaagcag tctccttacaa gagggacagg gtaaggcggg agctgcggtg    1620
accaccgaga ccgaggtaat ctgggctaaa gccctgccag ccgggacatc cgctcagcgg    1680
gctgaactga tagcactcac ccaggcccta aagatgcag aaggtaagaa gctaaatgtt    1740
tatactgata gccgttatgc ttttgctact gcccatatcc atggagaaat atacagaagg    1800
cgtgggttgc tcacatcaga aggcaaagag atcaaaaata agacgagat cttggcccta    1860
ctaaaagccc tctttctgcc caaaagactt agcataatcc attgtccagg acatcaaaag    1920
ggacacagcg ccgaggctag aggcaaccgg atggctgacc aagcggcccg aaaggcagcc    1980
```
atcacagaga ctccagacac ctctaccctc ctc                              2013

<210> SEQ ID NO 11
<211> LENGTH: 2013
<212> TYPE: DNA
<213> ORGANISM: Moloney murine leukemia virus
<220> FEATURE:
<221> NAME/KEY: modified_base
<222> LOCATION: (1570)..(1572)
<223> OTHER INFORMATION: This region may encompass 'aat' or 'aac'

<400> SEQUENCE: 11

```
accctaaata tagaagatga gcatcggcta catgagacct caaaagagcc agatgtttct     60
ctagggtcca catggctgtc tgattttcct caggcctggg cggaaaccgg gggcatggga    120
ctggcagttc gccaagctcc tctgatcata cctctgaaag caacctctac ccccgtgtcc    180
ataaaacaat accccatgtc acaagaagcc agactgggga tcaagcccca catacagaga    240
ctgttggacc agggaatact ggtaccctgc cagtccccct ggaacacgcc cctgctaccc    300
gttaagaaac cagggactaa tgattatagg cctgtccagg atctgagaga agtcaacaag    360
cgggtggaag acatccaccc caccgtgccc aacccttaca acctcttgag cgggctccca    420
ccgtcccacc agtggtacac tgtgcttgat ttaaaggatg cctttttctg cctgagactc    480
cacccccacca gtcagcctct cttcgccttt gagtggagag atccagagat gggaatctca    540
ggacaattga cctggaccag actcccacag ggtttcaaaa acagtcccac cctgtttgat    600
gaggcactgc acagagacct agcagacttc cggatccagc cccagacttt gatcctgcta    660
cagtacgtgg atgacttact gctggccgcc acttctgagc tagactgcca acaaggtact    720
cgggccctgt tacaaaccct agggaacctc gggtatcggg cctcggccaa gaaagcccaa    780
atttgccaga aacaggtcaa gtatctgggg tatcttctaa agagggtcag gagatggctg    840
actgaggcca gaaaagagac tgtgatgggg cagcctactc gaagacccc tcgacaacta    900
agggagttcc tagggacggc aggcttctgt cgcctctgga tccctggtt tgcagaaatg    960
gcagccccct tgtaccctct caccaaaacg gggactctgt ttaattgggg cccagaccaa   1020
caaaaggcct atcaagaaat caagcaagct cttctaactg ccccagccct ggggttgcca   1080
gatttgacta gcccctttga actctttgtc gacgagaagc agggctacgc caaaggtgtc   1140
ctaacgcaaa aactgggacc ttggcgtcgg ccggtggcct acctgtccaa aaagctagac   1200
ccagtagcag ctgggtggcc cccttgccta cggatggtag cagccattgc cgtactgaca   1260
aaggatgcag gcaagctaac catgggacag ccactagtcc ttctggcccc ccatgcagta   1320
gaggcactag tcaaacaacc ccccgaccgc tggcttttcca acgcccggat gactcactat   1380
caggccttgc ttttggacac ggaccgggtc cagttcggac cggtggtagc cctgaacccg   1440
gctacgctgc tcccactgcc tgaggaaggg ctgcaacaca actgccttga tatcctggcc   1500
gaagcccacg gaacccgacc cgacctaacg gaccagccgc tcccagacgc cgaccacacc   1560
tggtacacgn nnggaagcag tctcttacaa gagggacagc gtaaggcggg agctgcggtg   1620
accaccgaga ccgaggtaat ctgggctaaa gccctgccag ccgggacatc cgctcagcgg   1680
gctgaactga tagcactcac ccaggcccta aagatggcag aagtaagaa gctaaatgtt   1740
tatactgata gccgttatgc ttttgctact gcccatatcc atggagaaat atacagaagg   1800
cgtgggttgc tcacatcaga aggcaaagag atcaaaaata aagacgagat cttggcccta   1860
ctaaaagccc tctttctgcc caaaagactt agcataatcc attgtccagg acatcaaaag   1920
```

| | |
|---|---|
| ggacacagcg ccgaggctag aggcaaccgg atggctgacc aagcggcccg aaaggcagcc | 1980 |
| atcacagaga ctccagacac ctctaccctc ctc | 2013 |

<210> SEQ ID NO 12
<211> LENGTH: 2013
<212> TYPE: DNA
<213> ORGANISM: Moloney murine leukemia virus
<220> FEATURE:
<221> NAME/KEY: modified_base
<222> LOCATION: (1951)..(1953)
<223> OTHER INFORMATION: This region may encompass 'ctt', 'ctc', 'cta', 'ctg', 'tta' or 'ttg'

<400> SEQUENCE: 12

| | |
|---|---|
| accctaaata tagaagatga gcatcggcta catgagacct caaaagagcc agatgtttct | 60 |
| ctagggtcca catggctgtc tgattttcct caggcctggg cggaaaccgg gggcatggga | 120 |
| ctggcagttc gccaagctcc tctgatcata cctctgaaag caacctctac ccccgtgtcc | 180 |
| ataaaacaat accccatgtc acaagaagcc agactgggga tcaagcccca catacagaga | 240 |
| ctgttggacc agggaatact ggtaccctgc cagtccccct ggaacacgcc cctgctaccc | 300 |
| gttaagaaac cagggactaa tgattatagg cctgtccagg atctgagaga agtcaacaag | 360 |
| cgggtggaag acatccaccc caccgtgccc aaccttaca acctcttgag cgggctccca | 420 |
| ccgtcccacc agtggtacac tgtgcttgat ttaaaggatg ccttttttctg cctgagactc | 480 |
| caccccacca gtcagcctct cttcgccttt gagtggagag atccagagat gggaatctca | 540 |
| ggacaattga cctggaccag actcccacag ggtttcaaaa acagtcccac cctgtttgat | 600 |
| gaggcactgc acagagacct agcagacttc cggatccagc acccagactt gatcctgcta | 660 |
| cagtacgtgg atgacttact gctggccgcc acttctgagc tagactgcca acaaggtact | 720 |
| cgggccctgt tacaaacccct agggaacctc gggtatcggg cctcggccaa gaaagcccaa | 780 |
| atttgccaga aacaggtcaa gtatctgggg tatcttctaa aagagggtca gagatggctg | 840 |
| actgaggcca gaaaagagac tgtgatgggg cagcctactc cgaagacccc tcgacaacta | 900 |
| agggagttcc tagggacggc aggcttctgt cgcctctgga tccctgggtt tgcagaaatg | 960 |
| gcagccccct tgtaccctct caccaaaacg gggactctgt ttaattgggg cccagaccaa | 1020 |
| caaaaggcct atcaagaaat caagcaagct cttctaactg ccccagccct ggggttgcca | 1080 |
| gatttgacta gccctttga actctttgtc gacgagaagc agggctacgc caaaggtgtc | 1140 |
| ctaacgcaaa aactgggacc ttggcgtcgg ccggtggcct acctgtccaa aaagctagac | 1200 |
| ccagtagcag ctgggtggcc cccttgccta cggatggtag cagccattgc cgtactgaca | 1260 |
| aaggatgcag gcaagctaac catgggacag ccactagtca ttctggcccc ccatgcagta | 1320 |
| gaggcactag tcaaacaacc ccccgaccgc tggctttcca acgcccggat gactcactat | 1380 |
| caggccttgc ttttggacac ggaccgggtc cagttcggac cggtggtagc cctgaacccg | 1440 |
| gctacgctgc tcccactgcc tgaggaaggg ctgcaacaca actgccttga tatcctggcc | 1500 |
| gaagcccacg gaacccgacc cgacctaacg gaccagccgc tcccagacgc cgaccacacc | 1560 |
| tggtacacgg atggaagcag tctcttacaa gagggacagc gtaaggcggg agctgcggtg | 1620 |
| accaccgaga ccgaggtaat ctgggctaaa gccctgccag ccgggacatc cgctcagcgg | 1680 |
| gctgaactga tagcactcac ccaggccctg aagatggcag aaggtaagaa gctaaatgtt | 1740 |
| tatactgata gccgttatgc ttttgctact gcccatatcc atggagaaat atacagaagg | 1800 |
| cgtgggttgc tcacatcaga aggcaaagag atcaaaaata aagacgagat cttggcccta | 1860 |

```
ctaaaagccc tctttctgcc caaaagactt agcataatcc attgtccagg acatcaaaag    1920
ggacacagcg ccgaggctag aggcaaccgg nnngctgacc aagcggcccg aaaggcagcc    1980
atcacagaga ctccagacac ctctaccctc ctc                                 2013
```

<210> SEQ ID NO 13
<211> LENGTH: 2013
<212> TYPE: DNA
<213> ORGANISM: Moloney murine leukemia virus
<220> FEATURE:
<221> NAME/KEY: modified_base
<222> LOCATION: (205)..(207)
<223> OTHER INFORMATION: This region may encompass 'aaa' or 'aag'
<220> FEATURE:
<221> NAME/KEY: modified_base
<222> LOCATION: (904)..(906)
<223> OTHER INFORMATION: This region may encompass 'aaa' or 'aag'
<220> FEATURE:
<221> NAME/KEY: modified_base
<222> LOCATION: (937)..(939)
<223> OTHER INFORMATION: This region may encompass 'ttt' or 'ttc'
<220> FEATURE:
<221> NAME/KEY: modified_base
<222> LOCATION: (1303)..(1305)
<223> OTHER INFORMATION: This region may encompass 'ggt', 'ggc', 'gga'
    or 'ggg'
<220> FEATURE:
<221> NAME/KEY: modified_base
<222> LOCATION: (1360)..(1362)
<223> OTHER INFORMATION: This region may encompass 'aaa' or 'aag'

<400> SEQUENCE: 13

```
accctaaata tagaagatga gcatcggcta catgagacct caaaagagcc agatgtttct     60
ctagggtcca catggctgtc tgattttcct caggcctggg cggaaaccgg gggcatggga    120
ctggcagttc gccaagctcc tctgatcata cctctgaaag caacctctac ccccgtgtcc    180
ataaaacaat accccatgtc acaannngcc agactgggga tcaagcccca catacagaga    240
ctgttggacc agggaatact ggtaccctgc cagtccccct ggaacacgcc cctgctaccc    300
gttaagaaac cagggactaa tgattatagg cctgtccagg atctgagaga agtcaacaag    360
cgggtggaag acatccaccc caccgtgccc aacccttaca acctcttgag cgggctccca    420
ccgtcccacc agtggtacac tgtgcttgat ttaaaggatg ccttttttctg cctgagactc    480 caccccacca gtcagcctct cttcgccttt gagtggagag atccagagat gggaatctca    540
ggacaattga cctggaccag actcccacag ggtttcaaaa acagtccac cctgtttgat    600 gaggcactgc acagagacct agcagacttc cggatccagc acccagactt gatcctgcta    660
cagtacgtgg atgacttact gctggccgcc acttctgagc tagactgcca acaaggtact    720
cgggccctgt tacaaaccct agggaacctc gggtatcggg cctcggccaa gaaagcccaa    780
atttgccaga acaggtcaa gtatctgggg tatcttctaa agagggtca gagatggctg    840 actgaggcca gaaagagac tgtgatgggg cagcctactc gaagaccccc tcgacaacta    900
aggnnnttcc tagggacggc aggcttctgt cgcctcnnna tccctgggtt tgcagaaatg    960
gcagccccct tgtaccctct caccaaaacg gggactctgt ttaattgggg cccagaccaa   1020
caaaaggcct atcaagaaat caagcaagct cttctaactg ccccagcct ggggttgcca   1080 gatttgacta gcccttttga actctttgtc gacgagaagc agggctacgc caaggtgtc   1140 ctaacgcaaa aactgggacc ttggcgtcgg ccggtggcct acctgtccaa aaagctagac   1200
ccagtagcag ctgggtggcc cccttgccta cggatggtag cagccattgc cgtactgaca   1260
aaggatgcag gcaagctaac catgggacag ccactagtca ttnnngcccc ccatgcagta   1320
```

| | |
|---|---|
| gaggcactag tcaaacaacc ccccgaccgc tggctttccn nngcccggat gactcactat | 1380 |
| caggccttgc ttttggacac ggaccgggtc cagttcggac cggtggtagc cctgaacccg | 1440 |
| gctacgctgc tcccactgcc tgaggaaggg ctgcaacaca actgccttga tatcctggcc | 1500 |
| gaagcccacg gaacccgacc cgacctaacg gaccagccgc tcccagacgc cgaccacacc | 1560 |
| tggtacacgg atggaagcag tctcttacaa gagggacagc gtaaggcggg agctgcggtg | 1620 |
| accaccgaga ccgaggtaat ctgggctaaa gccctgccag ccgggacatc cgctcagcgg | 1680 |
| gctgaactga tagcactcac ccaggcccta agatggcag aaggtaagaa gctaaatgtt | 1740 |
| tatactgata gccgttatgc ttttgctact gcccatatcc atggagaaat atacagaagg | 1800 |
| cgtgggttgc tcacatcaga aggcaaagag atcaaaaata aagacgagat cttggcccta | 1860 |
| ctaaaagccc tctttctgcc caaaagactt agcataatcc attgtccagg acatcaaaag | 1920 |
| ggacacagcg ccgaggctag aggcaaccgg atggctgacc aagcggcccg aaaggcagcc | 1980 |
| atcacagaga ctccagacac ctctaccctc ctc | 2013 |

<210> SEQ ID NO 14
<211> LENGTH: 2013
<212> TYPE: DNA
<213> ORGANISM: Moloney murine leukemia virus
<220> FEATURE:
<221> NAME/KEY: modified_base
<222> LOCATION: (904)..(906)
<223> OTHER INFORMATION: This region may encompass 'aaa' or 'aag'
<220> FEATURE:
<221> NAME/KEY: modified_base
<222> LOCATION: (937)..(939)
<223> OTHER INFORMATION: This region may encompass 'ttt' or 'ttc'
<220> FEATURE:
<221> NAME/KEY: modified_base
<222> LOCATION: (1303)..(1305)
<223> OTHER INFORMATION: This region may encompass 'ggt', 'ggc', 'gga' or 'ggg'
<220> FEATURE:
<221> NAME/KEY: modified_base
<222> LOCATION: (1360)..(1362)
<223> OTHER INFORMATION: This region may encompass 'aaa' or 'aag'

<400> SEQUENCE: 14

| | |
|---|---|
| accctaaata tagaagatga gcatcggcta catgagacct caaaagagcc agatgtttct | 60 |
| ctagggtcca catggctgtc tgattttcct caggcctggg cggaaaccgg gggcatggga | 120 |
| ctggcagttc gccaagctcc tctgatcata cctctgaaag caacctctac ccccgtgtcc | 180 |
| ataaaacaat accccatgtc acaagaagcc agactgggga tcaagcccca catacagaga | 240 |
| ctgttggacc agggaatact ggtaccctgc cagtccccct ggaacacgcc cctgctaccc | 300 |
| gttaagaaac cagggactaa tgattatagg cctgtccagg atctgagaga agtcaacaag | 360 |
| cgggtggaag acatccaccc caccgtgccc aacccttaca acctcttgag cgggctccca | 420 |
| ccgtcccacc agtggtacac tgtgcttgat ttaaaggatg cctttttctg cctgagactc | 480 |
| caccccacca gtcagcctct cttcgccttt gagtggagag atccagagat gggaatctca | 540 |
| ggacaattga cctggaccag actcccacag ggtttcaaaa acagtcccac cctgtttgat | 600 |
| gaggcactgc acagagacct agcagacttc cggatccagc acccagactt gatcctgcta | 660 |
| cagtacgtgg atgacttact gctggccgcc acttctgagc tagactgcca acaaggtact | 720 |
| cgggccctgt tacaaaccct agggaacctc gggtatcggg cctcggccaa gaaagcccaa | 780 |
| atttgccaga aacaggtcaa gtatctgggg tatcttctaa aagagggtca gagatggctg | 840 |
| actgaggcca gaaaagagac tgtgatgggg cagcctactc cgaagacccc tcgacaacta | 900 |

| | | |
|---|---|---|
| aggnnnttcc tagggacggc aggcttctgt cgcctcnnna tccctgggtt tgcagaaatg | 960 | |
| gcagccccct tgtaccctct caccaaaacg gggactctgt ttaattgggg cccagaccaa | 1020 | |
| caaaaggcct atcaagaaat caagcaagct cttctaactg ccccagccct ggggttgcca | 1080 | |
| gatttgacta agcccttga actctttgtc gacgagaagc agggctacgc caaaggtgtc | 1140 | |
| ctaacgcaaa aactgggacc ttggcgtcgg ccggtggcct acctgtccaa aaagctagac | 1200 | |
| ccagtagcag ctgggtggcc cccttgccta cggatggtag cagccattgc cgtactgaca | 1260 | |
| aaggatgcag gcaagctaac catgggacag ccactagtca ttnnngcccc ccatgcagta | 1320 | |
| gaggcactag tcaaacaacc ccccgaccgc tggctttccn nngcccggat gactcactat | 1380 | |
| caggccttgc ttttggacac ggaccgggtc cagttcggac cggtggtagc cctgaacccg | 1440 | |
| gctacgctgc tcccactgcc tgaggaaggg ctgcaacaca actgccttga tatcctggcc | 1500 | |
| gaagcccacg gaacccgacc cgacctaacg gaccagccgc tcccagacgc cgaccacacc | 1560 | |
| tggtacacgg atggaagcag tctcttacaa gagggacagc gtaaggcggg agctgcggtg | 1620 | |
| accaccgaga ccgaggtaat ctgggctaaa gccctgccag ccgggacatc cgctcagcgg | 1680 | |
| gctgaactga tagcactcac ccaggcccta aagatggcag aaggtaagaa gctaaatgtt | 1740 | |
| tatactgata gccgttatgc ttttgctact gcccatatcc atggagaaat atacagaagg | 1800 | |
| cgtgggttgc tcacatcaga aggcaaagag atcaaaaata agacgagat cttggcccta | 1860 | |
| ctaaaagccc tctttctgcc caaaagactt agcataatcc attgtccagg acatcaaaag | 1920 | |
| ggacacagcg ccgaggctag aggcaaccgg atggctgacc aagcggcccg aaaggcagcc | 1980 | |
| atcacagaga ctccagacac ctctaccctc ctc | 2013 | |

```
<210> SEQ ID NO 15
<211> LENGTH: 2013
<212> TYPE: DNA
<213> ORGANISM: Moloney murine leukemia virus
<220> FEATURE:
<221> NAME/KEY: modified_base
<222> LOCATION: (904)..(906)
<223> OTHER INFORMATION: This region may encompass 'aaa' or 'aag'
<220> FEATURE:
<221> NAME/KEY: modified_base
<222> LOCATION: (937)..(939)
<223> OTHER INFORMATION: This region may encompass 'ttt' or 'ttc'
<220> FEATURE:
<221> NAME/KEY: modified_base
<222> LOCATION: (1303)..(1305)
<223> OTHER INFORMATION: This region may encompass 'ggt', 'ggc', 'gga'
      or 'ggg'

<400> SEQUENCE: 15
```

| | | |
|---|---|---|
| accctaaata tagaagatga gcatcggcta catgagacct caaaagagcc agatgtttct | 60 | |
| ctagggtcca catggctgtc tgattttcct caggcctggg cggaaaccgg gggcatggga | 120 | |
| ctggcagttc gccaagctcc tctgatcata cctctgaaag caacctctac ccccgtgtcc | 180 | |
| ataaaacaat accccatgtc acaagaagcc agactgggga tcaagcccca catacagaga | 240 | |
| ctgttggacc agggaatact ggtaccctgc cagtccccct ggaacacgcc cctgctaccc | 300 | |
| gttaagaaac cagggactaa tgattatagg cctgtccagg atctgagaga agtcaacaag | 360 | |
| cgggtggaag catccaccc caccgtgccc aaccccttaca acctcttgag cgggctccca | 420 | |
| ccgtcccacc agtggtacac tgtgcttgat ttaaaggatg ccttttttctg cctgagactc | 480 | |
| caccccacca gtcagcctct cttcgccttt gagtggagag atccagagat gggaatctca | 540 | |
| ggacaattga cctggaccag actcccacag ggtttcaaaa acagtccac cctgtttgat | 600 | |

| | |
|---|---|
| gaggcactgc acagagacct agcagacttc cggatccagc acccagactt gatcctgcta | 660 |
| cagtacgtgg atgacttact gctggccgcc acttctgagc tagactgcca acaaggtact | 720 |
| cgggccctgt tacaaaccct agggaacctc gggtatcggg cctcggccaa gaaagcccaa | 780 |
| atttgccaga acaggtcaa gtatctgggg tatcttctaa aagagggtca gagatggctg | 840 |
| actgaggcca gaaaagagac tgtgatgggg cagcctactc cgaagacccc tcgacaacta | 900 |
| aggnnnttcc tagggacggc aggcttctgt cgcctcnnna tccctgggtt tgcagaaatg | 960 |
| gcagccccct tgtaccctct caccaaaacg gggactctgt ttaattgggg cccagaccaa | 1020 |
| caaaaggcct atcaagaaat caagcaagct cttctaactg ccccagccct ggggttgcca | 1080 |
| gatttgacta agccctttga actctttgtc gacgagaagc agggctacgc caaaggtgtc | 1140 |
| ctaacgcaaa aactgggacc ttggcgtcgg ccggtggcct acctgtccaa aaagctagac | 1200 |
| ccagtagcag ctgggtggcc cccttgccta cggatggtag cagccattgc cgtactgaca | 1260 |
| aaggatgcag gcaagctaac catgggacag ccactagtca ttnnngcccc ccatgcagta | 1320 |
| gaggcactag tcaaacaacc ccccgaccgc tggctttcca acgcccggat gactcactat | 1380 |
| caggccttgc ttttggacac ggaccgggtc cagttcggac cggtggtagc cctgaacccg | 1440 |
| gctacgctgc tcccactgcc tgaggaaggg ctgcaacaca actgccttga tatcctggcc | 1500 |
| gaagcccacg gaacccgacc cgacctaacg gaccagccgc tcccagacgc cgaccacacc | 1560 |
| tggtacacga atggaagcag tctcttacaa gagggacagt gtaaggcggg agctgcggtg | 1620 |
| accaccgaga ccgaggtaat ctgggctaaa gccctgccag ccgggacatc cgctcagcgg | 1680 |
| gctgaactga tagcactcac ccaggcccta aagatgcag aagtaagaa gctaaatgtt | 1740 |
| tatactgata gccgttatgc ttttgctact gcccatatcc atggagaaat atacagaagg | 1800 |
| cgtgggttgc tcacatcaga aggcaaagag atcaaaaata aagacgagat cttggcccta | 1860 |
| ctaaaagccc tctttctgcc caaaagactt agcataatcc attgtccagg acatcaaaag | 1920 |
| ggacacagcg ccgaggctag aggcaaccgg atggctgacc aagcggcccg aaaggcagcc | 1980 |
| atcacagaga ctccagacac ctctaccctc ctc | 2013 |

<210> SEQ ID NO 16
<211> LENGTH: 2013
<212> TYPE: DNA
<213> ORGANISM: Moloney murine leukemia virus
<220> FEATURE:
<221> NAME/KEY: modified_base
<222> LOCATION: (205)..(207)
<223> OTHER INFORMATION: This region may encompass 'aaa' or 'aag'
<220> FEATURE:
<221> NAME/KEY: modified_base
<222> LOCATION: (904)..(906)
<223> OTHER INFORMATION: This region may encompass 'aaa' or 'aag'
<220> FEATURE:
<221> NAME/KEY: modified_base
<222> LOCATION: (1360)..(1362)
<223> OTHER INFORMATION: This region may encompass 'aaa' or 'aag'

<400> SEQUENCE: 16

| | |
|---|---|
| accctaaata tagaagatga gcatcggcta catgagacct caaaagagcc agatgtttct | 60 |
| ctagggtcca catggctgtc tgattttcct caggcctggg cggaaaccgg ggcatggga | 120 |
| ctggcagttc gccaagctcc tctgatcata cctctgaaag caacctctac ccccgtgtcc | 180 |
| ataaaacaat accccatgtc acaannngcc agactgggga tcaagcccca catacagaga | 240 |
| ctgttggacc agggaatact ggtacccctgc cagtcccct ggaacacgcc cctgctaccc | 300 |
| gttaagaaac cagggactaa tgattatagg cctgtccagg atctgagaga agtcaacaag | 360 |

```
cgggtggaag acatccaccc caccgtgccc aacccttaca aacctcttgag cgggctccca    420 ccgtcccacc agtggtacac tgtgcttgat ttaaaggatg cctttttctg cctgagactc    480
caccccacca gtcagcctct cttcgccttt gagtggagag atccagagat gggaatctca    540
ggacaattga cctggaccag actcccacag ggtttcaaaa acagtcccac cctgtttgat    600
gaggcactgc acagagacct agcagacttc cggatccagc acccagactt gatcctgcta    660
cagtacgtgg atgacttact gctggccgcc acttctgagc tagactgcca acaaggtact    720
cgggccctgt acaaaccct agggaacctc gggtatcggg cctcggccaa gaaagcccaa    780
atttgccaga aacaggtcaa gtatctgggg tatcttctaa aagagggtca gagatggctg    840
actgaggcca gaaaagagac tgtgatgggg cagcctactc cgaagacccc tcgacaacta    900
aggnnnttcc tagggacggc aggcttctgt cgcctctgga tccctgggtt tgcagaaatg    960
gcagccccct tgtaccctct caccaaaacg gggactctgt ttaattgggg cccagaccaa    1020
caaaaggcct atcaagaaat caagcaagct cttctaactg ccccagccct ggggttgcca    1080
gatttgacta agcccttga actctttgtc gacgagaagc agggctacgc caaaggtgtc    1140
ctaacgcaaa aactgggacc ttggcgtcgg ccggtggcct acctgtccaa aaagctagac    1200
ccagtagcag ctgggtggcc cccttgccta cggatggtag cagccattgc cgtactgaca    1260
aaggatgcag gcaagctaac catgggacag ccactagtca ttctggcccc ccatgcagta    1320
gaggcactag tcaaacaacc ccccgaccgc tggctttccn nngcccggat gactcactat    1380
caggccttgc ttttggacac ggaccgggtc cagttcggac cggtggtagc cctgaacccg    1440
gctacgctgc tcccactgcc tgaggaaggg ctgcaacaca actgccttga tatcctggcc    1500
gaagcccacg gaacccgacc cgacctaacg gaccagccgc tcccagacgc cgaccacacc    1560
tggtacacgg atggaagcag tctcttacaa gagggacagc gtaaggcggg agctgcggtg    1620
accaccgaga ccgaggtaat ctgggctaaa gccctgccag ccgggacatc cgctcagcgg    1680
gctgaactga tagcactcac ccaggcccta aagatggcag aaggtaagaa gctaaatgtt    1740
tatactgata gccgttatgc ttttgctact gcccatatcc atggagaaat atacagaagg    1800
cgtgggttgc tcacatcaga aggcaaagag atcaaaaata aagacgagat cttggcccta    1860
ctaaaagccc tctttctgcc caaaagactt agcataatcc attgtccagg acatcaaaag    1920
ggacacagcg ccgaggctag aggcaaccgg atggctgacc aagcggcccg aaaggcagcc    1980
atcacagaga ctccagacac ctctaccctc ctc                                 2013
```

<210> SEQ ID NO 17
<211> LENGTH: 2013
<212> TYPE: DNA
<213> ORGANISM: Moloney murine leukemia virus
<220> FEATURE:
<221> NAME/KEY: modified_base
<222> LOCATION: (904)..(906)
<223> OTHER INFORMATION: This region may encompass 'aaa' or 'aag'
<220> FEATURE:
<221> NAME/KEY: modified_base
<222> LOCATION: (937)..(939)
<223> OTHER INFORMATION: This region may encompass 'ttt' or 'ttc'

<400> SEQUENCE: 17

```
accctaaata tagaagatga gcatcggcta catgagacct caaaagagcc agatgtttct    60
ctagggtcca catggctgtc tgattttcct caggcctggg cggaaaccgg gggcatggga   120
ctggcagttc gccaagctcc tctgatcata cctctgaaag caacctctac ccccgtgtcc   180
```

```
ataaaacaat accccatgtc acaagaagcc agactgggga tcaagcccca catacagaga    240
ctgttggacc agggaatact ggtaccctgc cagtcccect ggaacacgcc cctgctaccc    300
gttaagaaac cagggactaa tgattatagg cctgtccagg atctgagaga agtcaacaag    360
cgggtggaag acatccaccc caccgtgccc aaccettaca acctcttgag cgggctccca    420
ccgtcccacc agtggtacac tgtgcttgat ttaaaggatg ccttttcctg cctgagactc    480
caccccacca gtcagcctct cttcgccttt gagtggagag atccagagat gggaatctca    540
ggacaattga cctggaccag actcccacag ggtttcaaaa acagtcccac cctgtttgat    600
gaggcactgc acagagacct agcagacttc cggatccagc cccagacttt gatcctgcta    660
cagtacgtgg atgacttact gctggccgcc acttctgagc tagactgcca acaaggtact    720
cgggccctgt tacaaaccct agggaacctc gggtatcggg cctcggccaa gaaagcccaa    780
atttgccaga aacaggtcaa gtatctgggg tatcttctaa aagagggtca gagatggctg    840
actgaggcca gaaagagac tgtgatgggg cagcctactc cgaagacccc tcgacaacta    900
aggnnnttcc tagggacggc aggcttctgt cgcctcnnna tccctgggtt tgcagaaatg    960
gcagcccct tgtaccctct caccaaaacg gggactctgt ttaattgggg cccagaccaa   1020
caaaaggcct atcaagaaat caagcaagct cttctaactg ccccagccct ggggttgcca   1080
gatttgacta agcccttga actctttgtc gacgagaagc agggctacgc caaaggtgtc   1140
ctaacgcaaa aactgggacc ttggcgtcgg ccggtggcct acctgtccaa aaagctagac   1200
ccagtagcag ctgggtggcc cccttgccta cggatggtag cagccattgc cgtactgaca   1260
aaggatgcag gcaagctaac catgggacag ccactagtca ttctggcccc ccatgcagta   1320
gaggcactag tcaaacaacc ccccgaccgc tggctttcca acgcccggat gactcactat   1380
caggccttgc ttttggacac ggaccgggtc cagttcggac cggtggtagc cctgaacccg   1440
gctacgctgc tcccactgcc tgaggaaggg ctgcaacaca actgccttga tatcctggcc   1500
gaagcccacg gaacccgacc cgacctaacg gaccagccgc tcccagacgc cgaccacacc   1560
tggtacacgg atggaagcag tctcttacaa gagggacagc gtaaggcggg agctgcggtg   1620
accaccgaga ccgaggtaat ctgggctaaa gccctgccag ccgggacatc cgctcagcgg   1680
gctgaactga tagcactcac ccaggcccta aagatggcag aaggtaagaa gctaaatgtt   1740
tatactgata gccgttatgc ttttgctact gcccatatcc atggagaaat atacagaagg   1800
cgtgggttgc tcacatcaga aggcaaagag atcaaaaata aagacgagat cttggcccta   1860
ctaaaagccc tctttctgcc caaaagactt agcataatcc attgtccagg acatcaaaag   1920
ggacacagcg ccgaggctag aggcaaccgg atggctgacc aagcggcccg aaaggcagcc   1980
atcacagaga ctccagacac ctctaccctc ctc                                2013
```

<210> SEQ ID NO 18
<211> LENGTH: 2013
<212> TYPE: DNA
<213> ORGANISM: Moloney murine leukemia virus
<220> FEATURE:
<221> NAME/KEY: modified_base
<222> LOCATION: (205)..(207)
<223> OTHER INFORMATION: This region may encompass 'aaa' or 'aag'
<220> FEATURE:
<221> NAME/KEY: modified_base
<222> LOCATION: (904)..(906)
<223> OTHER INFORMATION: This region may encompass 'aaa' or 'aag'
<220> FEATURE:
<221> NAME/KEY: modified_base
<222> LOCATION: (937)..(939)
<223> OTHER INFORMATION: This region may encompass 'ttt' or 'ttc'

```
<220> FEATURE:
<221> NAME/KEY: modified_base
<222> LOCATION: (1303)..(1305)
<223> OTHER INFORMATION: This region may encompass 'ggt', 'ggc', 'gga'
      or 'ggg'
<220> FEATURE:
<221> NAME/KEY: modified_base
<222> LOCATION: (1360)..(1362)
<223> OTHER INFORMATION: This region may encompass 'aaa' or 'aag'
<220> FEATURE:
<221> NAME/KEY: modified_base
<222> LOCATION: (1570)..(1572)
<223> OTHER INFORMATION: This region may encompass 'aat' or 'aac'

<400> SEQUENCE: 18
accctaaata tagaagatga gcatcggcta catgagacct caaaagagcc agatgtttct     60
ctagggtcca catggctgtc tgattttcct caggcctggg cggaaaccgg gggcatggga    120
ctggcagttc gccaagctcc tctgatcata cctctgaaag caacctctac ccccgtgtcc    180
ataaaacaat accccatgtc acaanngcc agactgggga tcaagcccca catacagaga    240
ctgttggacc agggaatact ggtaccctgc cagtccccct ggaacacgcc cctgctaccc    300
gttaagaaac cagggactaa tgattatagg cctgtccagg atctgagaga agtcaacaag    360
cgggtggaag acatccaccc caccgtgccc aaccccttaca acctcttgag cgggctccca    420
ccgtcccacc agtggtacac tgtgcttgat ttaaaggatg ccttttttctg cctgagactc    480
caccccacca gtcagcctct cttcgccttt gagtggagag atccagagat gggaatctca    540
ggacaattga cctggaccag actcccacag ggtttcaaaa acagtcccac cctgtttgat    600
gaggcactgc acagagacct agcagacttc cggatccagc acccagactt gatcctgcta    660
cagtacgtgg atgacttact gctggccgcc acttctgagc tagactgcca acaaggtact    720
cgggccctgt tacaaaccct agggaacctc gggtatcggg cctcggccaa gaaagcccaa    780
atttgccaga aacaggtcaa gtatctgggg tatcttctaa aagagggtca gagatggctg    840
actgaggcca gaaaagagac tgtgatgggg cagcctactc cgaagacccc tcgacaacta    900
aggnnnttcc tagggacggc aggcttctgt cgcctcnnna tccctgggtt tgcagaaatg    960
gcagccccct tgtaccctct caccaaaacg gggactctgt ttaattgggg cccagaccaa    1020
caaaaggcct atcaagaaat caagcaagct cttctaactg ccccagccct ggggttgcca    1080
gatttgacta agccctttga actctttgtc gacgagaagc agggctacgc caaaggtgtc    1140
ctaacgcaaa aactgggacc ttggcgtcgg ccggtggcct acctgtccaa aaagctagac    1200
ccagtagcag ctgggtggcc cccttgccta cggatggtag cagccattgc cgtactgaca    1260
aaggatgcag gcaagctaac catgggacag ccactagtca ttnnngcccc ccatgcagta    1320
gaggcactag tcaaacaacc ccccgaccgc tggctttccn nngcccggat gactcactat    1380
caggccttgc ttttggacac ggaccgggtc cagttcggac cggtggtagc cctgaacccg    1440
gctacgctgc tcccactgcc tgaggaaggg ctgcaacaca actgccttga tatcctggcc    1500
gaagcccacg gaacccgacc cgacctaacg gaccagccgc tcccagacgc cgaccacacc    1560
tggtacacgn nnggaagcag tctcttacaa gagggacagc gtaaggcggg agctgcggtg    1620
accaccgaga ccgaggtaat ctgggctaaa gccctgccag ccgggacatc cgctcagcgg    1680
gctgaactga tagcactcac ccaggcccta aagatggcag aaggtaagaa gctaaatgtt    1740
tatactgata gccgttatgc ttttgctact gcccatatcc atggagaaat atacagaagg    1800
cgtgggttgc tcacatcaga aggcaaagag atcaaaaata aagacgagat cttggcccta    1860
ctaaaagccc tctttctgcc caaaagactt agcataatcc attgtccagg acatcaaaag    1920
```

```
ggacacagcg ccgaggctag aggcaaccgg atggctgacc aagcggcccg aaaggcagcc    1980
atcacagaga ctccagacac ctctaccctc ctc                                 2013
```

<210> SEQ ID NO 19
<211> LENGTH: 671
<212> TYPE: PRT
<213> ORGANISM: Moloney murine leukemia virus

<400> SEQUENCE: 19

```
Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350
```

-continued

```
Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
                420                 425                 430

Val Ile Leu Ala Pro His Ala Val Glu Ala Leu Val Lys Gln Pro Pro
            435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
                500                 505                 510

Pro Leu Pro Asp Ala Asp His Thr Trp Tyr Thr Asp Gly Ser Ser Leu
            515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
                580                 585                 590

Ile His Gly Glu Ile Tyr Arg Arg Arg Gly Leu Leu Thr Ser Glu Gly
            595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu
                660                 665                 670

<210> SEQ ID NO 20
<211> LENGTH: 671
<212> TYPE: PRT
<213> ORGANISM: Moloney murine leukemia virus

<400> SEQUENCE: 20

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
            35                  40                  45

Ile Ile Pro Leu Lys Ala Thr Ser Thr Pro Val Ser Ile Lys Gln Tyr
    50                  55                  60
```

```
Pro Met Ser Gln Lys Ala Arg Leu Gly Ile Lys Pro His Ile Gln Arg
 65                  70                  75                  80

Leu Leu Asp Gln Gly Ile Leu Val Pro Cys Gln Ser Pro Trp Asn Thr
                 85                  90                  95

Pro Leu Leu Pro Val Lys Lys Pro Gly Thr Asn Asp Tyr Arg Pro Val
                100                 105                 110

Gln Asp Leu Arg Glu Val Asn Lys Arg Val Glu Asp Ile His Pro Thr
            115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
        450                 455                 460

Leu Asp Thr Asp Arg Val Gln Phe Gly Pro Val Val Ala Leu Asn Pro
465                 470                 475                 480
```

Ala Thr Leu Leu Pro Leu Pro Glu Glu Gly Leu Gln His Asn Cys Leu
            485                 490                 495

Asp Ile Leu Ala Glu Ala His Gly Thr Arg Pro Asp Leu Thr Asp Gln
        500                 505                 510

Pro Leu Pro Asp Ala Asp His Thr Trp Tyr Thr Asp Gly Ser Ser Leu
            515                 520                 525

Leu Gln Glu Gly Gln Arg Lys Ala Gly Ala Ala Val Thr Thr Glu Thr
        530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
            565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Leu Leu Thr Ser Glu Gly
            595                 600                 605

Lys Glu Ile Lys Asn Lys Asp Glu Ile Leu Ala Leu Leu Lys Ala Leu
        610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
            645                 650                 655

Arg Lys Ala Ala Ile Thr Glu Thr Pro Asp Thr Ser Thr Leu Leu
            660                 665                 670

<210> SEQ ID NO 21
<211> LENGTH: 671
<212> TYPE: PRT
<213> ORGANISM: Moloney murine leukemia virus

<400> SEQUENCE: 21

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
            85                  90                  95

Pro Leu Leu Pro Val Lys Lys Pro Gly Thr Asn Asp Tyr Arg Pro Val
        100                 105                 110

Gln Asp Leu Arg Glu Val Asn Lys Arg Val Glu Asp Ile His Pro Thr
    115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
            165                 170                 175

Met Gly Ile Ser Gly Gln Leu Thr Trp Thr Arg Leu Pro Gln Gly Phe
        180                 185                 190

-continued

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
                260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Lys Phe Leu
        290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
                340                 345                 350

Thr Ala Pro Ala Leu Gly Leu Pro Asp Leu Thr Lys Pro Phe Glu Leu
                355                 360                 365

Phe Val Asp Glu Lys Gln Gly Tyr Ala Lys Gly Val Leu Thr Gln Lys
        370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
                420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
        450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
                500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
        530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
                580                 585                 590

Ile His Gly Glu Ile Tyr Arg Arg Arg Gly Leu Leu Thr Ser Glu Gly
        595                 600                 605

```
Lys Glu Ile Lys Asn Lys Asp Glu Ile Leu Ala Leu Leu Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu
            660                 665                 670

<210> SEQ ID NO 22
<211> LENGTH: 671
<212> TYPE: PRT
<213> ORGANISM: Moloney murine leukemia virus

<400> SEQUENCE: 22

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Arg Phe Leu
    290                 295                 300

Gly Thr Ala Gly Phe Cys Arg Leu Trp Ile Pro Gly Phe Ala Glu Met
305                 310                 315                 320
```

```
Ala Ala Pro Leu Tyr Pro Leu Thr Lys Thr Gly Thr Leu Phe Asn Trp
            325                 330                 335

Gly Pro Asp Gln Gln Lys Ala Tyr Gln Glu Ile Lys Gln Ala Leu Leu
        340                 345                 350

Thr Ala Pro Ala Leu Gly Leu Pro Asp Leu Thr Lys Pro Phe Glu Leu
            355                 360                 365

Phe Val Asp Glu Lys Gln Gly Tyr Ala Lys Gly Val Leu Thr Gln Lys
370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
            435                 440                 445

Asp Arg Trp Leu Ser Asn Ala Arg Met Thr His Tyr Gln Ala Leu Leu
        450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu
            660                 665                 670

<210> SEQ ID NO 23
<211> LENGTH: 671
<212> TYPE: PRT
<213> ORGANISM: Moloney murine leukemia virus

<400> SEQUENCE: 23

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
```

-continued

```
                 20                  25                  30
Trp Ala Glu Thr Gly Gly Met Gly Leu Ala Val Arg Gln Ala Pro Leu
             35                  40                  45
Ile Ile Pro Leu Lys Ala Thr Ser Thr Pro Val Ser Ile Lys Gln Tyr
         50                  55                  60
Pro Met Ser Gln Glu Ala Arg Leu Gly Ile Lys Pro His Ile Gln Arg
 65                  70                  75                  80
Leu Leu Asp Gln Gly Ile Leu Val Pro Cys Gln Ser Pro Trp Asn Thr
                 85                  90                  95
Pro Leu Leu Pro Val Lys Lys Pro Gly Thr Asn Asp Tyr Arg Pro Val
             100                 105                 110
Gln Asp Leu Arg Glu Val Asn Lys Arg Val Glu Asp Ile His Pro Thr
         115                 120                 125
Val Pro Asn Pro Tyr Asn Leu Leu Ser Gly Leu Pro Pro Ser His Gln
 130                 135                 140
Trp Tyr Thr Val Leu Asp Leu Lys Asp Ala Phe Phe Cys Leu Arg Leu
145                 150                 155                 160
His Pro Thr Ser Gln Pro Leu Phe Ala Phe Glu Trp Arg Asp Pro Glu
                 165                 170                 175
Met Gly Ile Ser Gly Gln Leu Thr Trp Thr Arg Leu Pro Gln Gly Phe
             180                 185                 190
Lys Asn Ser Pro Thr Leu Phe Asp Glu Ala Leu His Arg Asp Leu Ala
         195                 200                 205
Asp Phe Arg Ile Gln His Pro Asp Leu Ile Leu Leu Gln Tyr Val Asp
 210                 215                 220
Asp Leu Leu Leu Ala Ala Thr Ser Glu Leu Asp Cys Gln Gln Gly Thr
225                 230                 235                 240
Arg Ala Leu Leu Gln Thr Leu Gly Asn Leu Gly Tyr Arg Ala Ser Ala
                 245                 250                 255
Lys Lys Ala Gln Ile Cys Gln Lys Gln Val Lys Tyr Leu Gly Tyr Leu
             260                 265                 270
Leu Lys Glu Gly Gln Arg Trp Leu Thr Glu Ala Arg Lys Glu Thr Val
         275                 280                 285
Met Gly Gln Pro Thr Pro Lys Thr Pro Arg Gln Leu Arg Glu Phe Leu
 290                 295                 300
Gly Thr Ala Gly Phe Cys Arg Leu Phe Ile Pro Gly Phe Ala Glu Met
305                 310                 315                 320
Ala Ala Pro Leu Tyr Pro Leu Thr Lys Thr Gly Thr Leu Phe Asn Trp
                 325                 330                 335
Gly Pro Asp Gln Gln Lys Ala Tyr Gln Glu Ile Lys Gln Ala Leu Leu
             340                 345                 350
Thr Ala Pro Ala Leu Gly Leu Pro Asp Leu Thr Lys Pro Phe Glu Leu
         355                 360                 365
Phe Val Asp Glu Lys Gln Gly Tyr Ala Lys Gly Val Leu Thr Gln Lys
 370                 375                 380
Leu Gly Pro Trp Arg Arg Pro Val Ala Tyr Leu Ser Lys Lys Leu Asp
385                 390                 395                 400
Pro Val Ala Ala Gly Trp Pro Pro Cys Leu Arg Met Val Ala Ala Ile
                 405                 410                 415
Ala Val Leu Thr Lys Asp Ala Gly Lys Leu Thr Met Gly Gln Pro Leu
             420                 425                 430
Val Ile Leu Ala Pro His Ala Val Glu Ala Leu Val Lys Gln Pro Pro
         435                 440                 445
```

```
Asp Arg Trp Leu Ser Asn Ala Arg Met Thr His Tyr Gln Ala Leu Leu
        450                 455                 460

Leu Asp Thr Asp Arg Val Gln Phe Gly Pro Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
                500                 505                 510

Pro Leu Pro Asp Ala Asp His Thr Trp Tyr Thr Asp Gly Ser Ser Leu
            515                 520                 525

Leu Gln Glu Gly Gln Arg Lys Ala Gly Ala Ala Val Thr Thr Glu Thr
        530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
                580                 585                 590

Ile His Gly Glu Ile Tyr Arg Arg Arg Gly Leu Leu Thr Ser Glu Gly
            595                 600                 605

Lys Glu Ile Lys Asn Lys Asp Glu Ile Leu Ala Leu Leu Lys Ala Leu
        610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu
            660                 665                 670

<210> SEQ ID NO 24
<211> LENGTH: 671
<212> TYPE: PRT
<213> ORGANISM: Moloney murine leukemia virus

<400> SEQUENCE: 24

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
            35                  40                  45

Ile Ile Pro Leu Lys Ala Thr Ser Thr Pro Val Ser Ile Lys Gln Tyr
        50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
                100                 105                 110

Gln Asp Leu Arg Glu Val Asn Lys Arg Val Glu Asp Ile His Pro Thr
            115                 120                 125

Val Pro Asn Pro Tyr Asn Leu Leu Ser Gly Leu Pro Pro Ser His Gln
        130                 135                 140

Trp Tyr Thr Val Leu Asp Leu Lys Asp Ala Phe Phe Cys Leu Arg Leu
```

```
            145                 150                 155                 160
His Pro Thr Ser Gln Pro Leu Phe Ala Phe Glu Trp Arg Asp Pro Glu
                    165                 170                 175
Met Gly Ile Ser Gly Gln Leu Thr Trp Thr Arg Leu Pro Gln Gly Phe
                    180                 185                 190
Lys Asn Ser Pro Thr Leu Phe Asp Glu Ala Leu His Arg Asp Leu Ala
                    195                 200                 205
Asp Phe Arg Ile Gln His Pro Asp Leu Ile Leu Leu Gln Tyr Val Asp
            210                 215                 220
Asp Leu Leu Leu Ala Ala Thr Ser Glu Leu Asp Cys Gln Gln Gly Thr
225                 230                 235                 240
Arg Ala Leu Leu Gln Thr Leu Gly Asn Leu Gly Tyr Arg Ala Ser Ala
                    245                 250                 255
Lys Lys Ala Gln Ile Cys Gln Lys Gln Val Lys Tyr Leu Gly Tyr Leu
                    260                 265                 270
Leu Lys Glu Gly Gln Arg Trp Leu Thr Glu Ala Arg Lys Glu Thr Val
                    275                 280                 285
Met Gly Gln Pro Thr Pro Lys Thr Pro Arg Gln Leu Arg Glu Phe Leu
            290                 295                 300
Gly Thr Ala Gly Phe Cys Arg Leu Trp Ile Pro Gly Phe Ala Glu Met
305                 310                 315                 320
Ala Ala Pro Leu Tyr Pro Leu Thr Lys Thr Gly Thr Leu Phe Asn Trp
                    325                 330                 335
Gly Pro Asp Gln Gln Lys Ala Tyr Gln Glu Ile Lys Gln Ala Leu Leu
                    340                 345                 350
Thr Ala Pro Ala Leu Gly Leu Pro Asp Leu Thr Lys Pro Phe Glu Leu
            355                 360                 365
Phe Val Asp Glu Lys Gln Gly Tyr Ala Lys Gly Val Leu Thr Gln Lys
            370                 375                 380
Leu Gly Pro Trp Arg Arg Pro Val Ala Tyr Leu Ser Lys Lys Leu Asp
385                 390                 395                 400
Pro Val Ala Ala Gly Trp Pro Pro Cys Leu Arg Met Val Ala Ala Ile
                    405                 410                 415
Ala Val Leu Thr Lys Asp Ala Gly Lys Leu Thr Met Gly Gln Pro Leu
                    420                 425                 430
Val Ile Gly Ala Pro His Ala Val Glu Ala Leu Val Lys Gln Pro Pro
            435                 440                 445
Asp Arg Trp Leu Ser Asn Ala Arg Met Thr His Tyr Gln Ala Leu Leu
            450                 455                 460
Leu Asp Thr Asp Arg Val Gln Phe Gly Pro Val Val Ala Leu Asn Pro
465                 470                 475                 480
Ala Thr Leu Leu Pro Leu Pro Glu Glu Gly Leu Gln His Asn Cys Leu
                    485                 490                 495
Asp Ile Leu Ala Glu Ala His Gly Thr Arg Pro Asp Leu Thr Asp Gln
                    500                 505                 510
Pro Leu Pro Asp Ala Asp His Thr Trp Tyr Thr Asp Gly Ser Ser Leu
            515                 520                 525
Leu Gln Glu Gly Gln Arg Lys Ala Gly Ala Ala Val Thr Thr Glu Thr
            530                 535                 540
Glu Val Ile Trp Ala Lys Ala Leu Pro Ala Gly Thr Ser Ala Gln Arg
545                 550                 555                 560
Ala Glu Leu Ile Ala Leu Thr Gln Ala Leu Lys Met Ala Glu Gly Lys
                    565                 570                 575
```

```
Lys Leu Asn Val Tyr Thr Asp Ser Arg Tyr Ala Phe Ala Thr Ala His
            580                 585                 590

Ile His Gly Glu Ile Tyr Arg Arg Gly Leu Leu Thr Ser Glu Gly
        595                 600                 605

Lys Glu Ile Lys Asn Lys Asp Glu Ile Leu Ala Leu Leu Lys Ala Leu
610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
            645                 650                 655

Arg Lys Ala Ala Ile Thr Glu Thr Pro Asp Thr Ser Thr Leu Leu
            660                 665                 670

<210> SEQ ID NO 25
<211> LENGTH: 671
<212> TYPE: PRT
<213> ORGANISM: Moloney murine leukemia virus

<400> SEQUENCE: 25

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
```

```
                275                 280                 285
Met Gly Gln Pro Thr Pro Lys Thr Pro Arg Gln Leu Arg Glu Phe Leu
290                 295                 300
Gly Thr Ala Gly Phe Cys Arg Leu Trp Ile Pro Gly Phe Ala Glu Met
305                 310                 315                 320
Ala Ala Pro Leu Tyr Pro Leu Thr Lys Thr Gly Thr Leu Phe Asn Trp
                325                 330                 335
Gly Pro Asp Gln Gln Lys Ala Tyr Gln Glu Ile Lys Gln Ala Leu Leu
            340                 345                 350
Thr Ala Pro Ala Leu Gly Leu Pro Asp Leu Thr Lys Pro Phe Glu Leu
        355                 360                 365
Phe Val Asp Glu Lys Gln Gly Tyr Ala Lys Gly Val Leu Thr Gln Lys
370                 375                 380
Leu Gly Pro Trp Arg Arg Pro Val Ala Tyr Leu Ser Lys Lys Leu Asp
385                 390                 395                 400
Pro Val Ala Ala Gly Trp Pro Pro Cys Leu Arg Met Val Ala Ala Ile
                405                 410                 415
Ala Val Leu Thr Lys Asp Ala Gly Lys Leu Thr Met Gly Gln Pro Leu
            420                 425                 430
Val Ile Met Ala Pro His Ala Val Glu Ala Leu Val Lys Gln Pro Pro
        435                 440                 445
Asp Arg Trp Leu Ser Asn Ala Arg Met Thr His Tyr Gln Ala Leu Leu
450                 455                 460
Leu Asp Thr Asp Arg Val Gln Phe Gly Pro Val Val Ala Leu Asn Pro
465                 470                 475                 480
Ala Thr Leu Leu Pro Leu Pro Glu Glu Gly Leu Gln His Asn Cys Leu
                485                 490                 495
Asp Ile Leu Ala Glu Ala His Gly Thr Arg Pro Asp Leu Thr Asp Gln
            500                 505                 510
Pro Leu Pro Asp Ala Asp His Thr Trp Tyr Thr Asp Gly Ser Ser Leu
        515                 520                 525
Leu Gln Glu Gly Gln Arg Lys Ala Gly Ala Ala Val Thr Thr Glu Thr
530                 535                 540
Glu Val Ile Trp Ala Lys Ala Leu Pro Ala Gly Thr Ser Ala Gln Arg
545                 550                 555                 560
Ala Glu Leu Ile Ala Leu Thr Gln Ala Leu Lys Met Ala Glu Gly Lys
                565                 570                 575
Lys Leu Asn Val Tyr Thr Asp Ser Arg Tyr Ala Phe Ala Thr Ala His
            580                 585                 590
Ile His Gly Glu Ile Tyr Arg Arg Arg Gly Leu Leu Thr Ser Glu Gly
        595                 600                 605
Lys Glu Ile Lys Asn Lys Asp Glu Ile Leu Ala Leu Leu Lys Ala Leu
    610                 615                 620
Phe Leu Pro Lys Arg Leu Ser Ile Ile His Cys Pro Gly His Gln Lys
625                 630                 635                 640
Gly His Ser Ala Glu Ala Arg Gly Asn Arg Met Ala Asp Gln Ala Ala
                645                 650                 655
Arg Lys Ala Ala Ile Thr Glu Thr Pro Asp Thr Ser Thr Leu Leu
            660                 665                 670

<210> SEQ ID NO 26
<211> LENGTH: 671
<212> TYPE: PRT
<213> ORGANISM: Moloney murine leukemia virus
```

<400> SEQUENCE: 26

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile

```
                    405                 410                 415
Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
            435                 440                 445

Asp Arg Trp Leu Ser Lys Ala Arg Met Thr His Tyr Gln Ala Leu Leu
450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
            485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
            515                 520                 525

Leu Gln Glu Gly Gln Arg Lys Ala Gly Ala Ala Val Thr Thr Glu Thr
530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
            565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Leu Leu Thr Ser Glu Gly
            595                 600                 605

Lys Glu Ile Lys Asn Lys Asp Glu Ile Leu Ala Leu Leu Lys Ala Leu
610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
            645                 650                 655

Arg Lys Ala Ala Ile Thr Glu Thr Pro Asp Thr Ser Thr Leu Leu
            660                 665                 670

<210> SEQ ID NO 27
<211> LENGTH: 671
<212> TYPE: PRT
<213> ORGANISM: Moloney murine leukemia virus

<400> SEQUENCE: 27

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110
```

```
Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
                180                 185                 190

Lys Asn Ser Pro Thr Leu Phe Asp Glu Ala Leu His Arg Asp Leu Ala
            195                 200                 205

Asp Phe Arg Ile Gln His Pro Asp Leu Ile Leu Leu Gln Tyr Val Asp
        210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
        290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Arg Ala Arg Met Thr His Tyr Gln Ala Leu Leu
        450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
```

-continued

```
            530                 535                 540
Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
                580                 585                 590

Ile His Gly Glu Ile Tyr Arg Arg Gly Leu Leu Thr Ser Glu Gly
                595                 600                 605

Lys Glu Ile Lys Asn Lys Asp Glu Ile Leu Ala Leu Leu Lys Ala Leu
                610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu
                660                 665                 670

<210> SEQ ID NO 28
<211> LENGTH: 671
<212> TYPE: PRT
<213> ORGANISM: Moloney murine leukemia virus

<400> SEQUENCE: 28

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
            35                  40                  45

Ile Ile Pro Leu Lys Ala Thr Ser Thr Pro Val Ser Ile Lys Gln Tyr
50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
210                 215                 220

Asp Leu Leu Leu Ala Ala Thr Ser Glu Leu Asp Cys Gln Gln Gly Thr
225                 230                 235                 240
```

-continued

```
Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asn Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Gly Leu Leu Thr Ser Glu Gly
        595                 600                 605

Lys Glu Ile Lys Asn Lys Asp Glu Ile Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu
```

-continued

```
                660                 665                 670
```

<210> SEQ ID NO 29
<211> LENGTH: 671
<212> TYPE: PRT
<213> ORGANISM: Moloney murine leukemia virus

<400> SEQUENCE: 29

```
Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365
```

```
Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Leu Ala Asp Gln Ala Ala
                645                 650                 655

Arg Lys Ala Ala Ile Thr Glu Thr Pro Asp Thr Ser Thr Leu Leu
            660                 665                 670
```

<210> SEQ ID NO 30
<211> LENGTH: 671
<212> TYPE: PRT
<213> ORGANISM: Moloney murine leukemia virus

<400> SEQUENCE: 30

```
Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
            35                  40                  45

Ile Ile Pro Leu Lys Ala Thr Ser Thr Pro Val Ser Ile Lys Gln Tyr
        50                  55                  60

Pro Met Ser Gln Lys Ala Arg Leu Gly Ile Lys Pro His Ile Gln Arg
65                  70                  75                  80
```

```
Leu Leu Asp Gln Gly Ile Leu Val Pro Cys Gln Ser Pro Trp Asn Thr
            85                  90                  95
Pro Leu Leu Pro Val Lys Lys Pro Gly Thr Asn Asp Tyr Arg Pro Val
            100                 105                 110
Gln Asp Leu Arg Glu Val Asn Lys Arg Val Glu Asp Ile His Pro Thr
            115                 120                 125
Val Pro Asn Pro Tyr Asn Leu Leu Ser Gly Leu Pro Pro Ser His Gln
    130                 135                 140
Trp Tyr Thr Val Leu Asp Leu Lys Asp Ala Phe Phe Cys Leu Arg Leu
145                 150                 155                 160
His Pro Thr Ser Gln Pro Leu Phe Ala Phe Glu Trp Arg Asp Pro Glu
                165                 170                 175
Met Gly Ile Ser Gly Gln Leu Thr Trp Thr Arg Leu Pro Gln Gly Phe
            180                 185                 190
Lys Asn Ser Pro Thr Leu Phe Asp Glu Ala Leu His Arg Asp Leu Ala
            195                 200                 205
Asp Phe Arg Ile Gln His Pro Asp Leu Ile Leu Leu Gln Tyr Val Asp
    210                 215                 220
Asp Leu Leu Leu Ala Ala Thr Ser Glu Leu Asp Cys Gln Gln Gly Thr
225                 230                 235                 240
Arg Ala Leu Leu Gln Thr Leu Gly Asn Leu Gly Tyr Arg Ala Ser Ala
                245                 250                 255
Lys Lys Ala Gln Ile Cys Gln Lys Gln Val Lys Tyr Leu Gly Tyr Leu
            260                 265                 270
Leu Lys Glu Gly Gln Arg Trp Leu Thr Glu Ala Arg Lys Glu Thr Val
            275                 280                 285
Met Gly Gln Pro Thr Pro Lys Thr Pro Arg Gln Leu Arg Arg Phe Leu
            290                 295                 300
Gly Thr Ala Gly Phe Cys Arg Leu Phe Ile Pro Gly Phe Ala Glu Met
305                 310                 315                 320
Ala Ala Pro Leu Tyr Pro Leu Thr Lys Thr Gly Thr Leu Phe Asn Trp
                325                 330                 335
Gly Pro Asp Gln Gln Lys Ala Tyr Gln Glu Ile Lys Gln Ala Leu Leu
            340                 345                 350
Thr Ala Pro Ala Leu Gly Leu Pro Asp Leu Thr Lys Pro Phe Glu Leu
            355                 360                 365
Phe Val Asp Glu Lys Gln Gly Tyr Ala Lys Gly Val Leu Thr Gln Lys
    370                 375                 380
Leu Gly Pro Trp Arg Arg Pro Val Ala Tyr Leu Ser Lys Lys Leu Asp
385                 390                 395                 400
Pro Val Ala Ala Gly Trp Pro Pro Cys Leu Arg Met Val Ala Ala Ile
                405                 410                 415
Ala Val Leu Thr Lys Asp Ala Gly Lys Leu Thr Met Gly Gln Pro Leu
            420                 425                 430
Val Ile Gly Ala Pro His Ala Val Glu Ala Leu Val Lys Gln Pro Pro
            435                 440                 445
Asp Arg Trp Leu Ser Lys Ala Arg Met Thr His Tyr Gln Ala Leu Leu
    450                 455                 460
Leu Asp Thr Asp Arg Val Gln Phe Gly Pro Val Val Ala Leu Asn Pro
465                 470                 475                 480
Ala Thr Leu Leu Pro Leu Pro Glu Glu Gly Leu Gln His Asn Cys Leu
                485                 490                 495
```

-continued

```
Asp Ile Leu Ala Glu Ala His Gly Thr Arg Pro Asp Leu Thr Asp Gln
                500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu
            660                 665                 670
```

<210> SEQ ID NO 31
<211> LENGTH: 671
<212> TYPE: PRT
<213> ORGANISM: Moloney murine leukemia virus

<400> SEQUENCE: 31

```
Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
            35                  40                  45

Ile Ile Pro Leu Lys Ala Thr Ser Thr Pro Val Ser Ile Lys Gln Tyr
        50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205
```

-continued

```
Asp Phe Arg Ile Gln His Pro Asp Leu Ile Leu Leu Gln Tyr Val Asp
    210                 215                 220
Asp Leu Leu Ala Ala Thr Ser Glu Leu Asp Cys Gln Gln Gly Thr
225                 230                 235                 240
Arg Ala Leu Leu Gln Thr Leu Gly Asn Leu Gly Tyr Arg Ala Ser Ala
                245                 250                 255
Lys Lys Ala Gln Ile Cys Gln Lys Gln Val Lys Tyr Leu Gly Tyr Leu
                260                 265                 270
Leu Lys Glu Gly Gln Arg Trp Leu Thr Glu Ala Arg Lys Glu Thr Val
            275                 280                 285
Met Gly Gln Pro Thr Pro Lys Thr Pro Arg Gln Leu Arg Arg Phe Leu
    290                 295                 300
Gly Thr Ala Gly Phe Cys Arg Leu Phe Ile Pro Gly Phe Ala Glu Met
305                 310                 315                 320
Ala Ala Pro Leu Tyr Pro Leu Thr Lys Thr Gly Thr Leu Phe Asn Trp
                325                 330                 335
Gly Pro Asp Gln Gln Lys Ala Tyr Gln Glu Ile Lys Gln Ala Leu Leu
            340                 345                 350
Thr Ala Pro Ala Leu Gly Leu Pro Asp Leu Thr Lys Pro Phe Glu Leu
            355                 360                 365
Phe Val Asp Glu Lys Gln Gly Tyr Ala Lys Gly Val Leu Thr Gln Lys
    370                 375                 380
Leu Gly Pro Trp Arg Arg Pro Val Ala Tyr Leu Ser Lys Lys Leu Asp
385                 390                 395                 400
Pro Val Ala Ala Gly Trp Pro Pro Cys Leu Arg Met Val Ala Ala Ile
                405                 410                 415
Ala Val Leu Thr Lys Asp Ala Gly Lys Leu Thr Met Gly Gln Pro Leu
            420                 425                 430
Val Ile Gly Ala Pro His Ala Val Glu Ala Leu Val Lys Gln Pro Pro
    435                 440                 445
Asp Arg Trp Leu Ser Lys Ala Arg Met Thr His Tyr Gln Ala Leu Leu
    450                 455                 460
Leu Asp Thr Asp Arg Val Gln Phe Gly Pro Val Val Ala Leu Asn Pro
465                 470                 475                 480
Ala Thr Leu Leu Pro Leu Pro Glu Glu Gly Leu Gln His Asn Cys Leu
                485                 490                 495
Asp Ile Leu Ala Glu Ala His Gly Thr Arg Pro Asp Leu Thr Asp Gln
            500                 505                 510
Pro Leu Pro Asp Ala Asp His Thr Trp Tyr Thr Asp Gly Ser Ser Leu
    515                 520                 525
Leu Gln Glu Gly Gln Arg Lys Ala Gly Ala Ala Val Thr Thr Glu Thr
    530                 535                 540
Glu Val Ile Trp Ala Lys Ala Leu Pro Ala Gly Thr Ser Ala Gln Arg
545                 550                 555                 560
Ala Glu Leu Ile Ala Leu Thr Gln Ala Leu Lys Met Ala Glu Gly Lys
                565                 570                 575
Lys Leu Asn Val Tyr Thr Asp Ser Arg Tyr Ala Phe Ala Thr Ala His
                580                 585                 590
Ile His Gly Glu Ile Tyr Arg Arg Arg Gly Leu Leu Thr Ser Glu Gly
            595                 600                 605
Lys Glu Ile Lys Asn Lys Asp Glu Ile Leu Ala Leu Leu Lys Ala Leu
    610                 615                 620
```

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
            645                 650                 655

Arg Lys Ala Ala Ile Thr Glu Thr Pro Asp Thr Ser Thr Leu Leu
        660                 665                 670

<210> SEQ ID NO 32
<211> LENGTH: 671
<212> TYPE: PRT
<213> ORGANISM: Moloney murine leukemia virus

<400> SEQUENCE: 32

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
290                 295                 300

Gly Thr Ala Gly Phe Cys Arg Leu Phe Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
            355                 360                 365

Phe Val Asp Glu Lys Gln Gly Tyr Ala Lys Gly Val Leu Thr Gln Lys
            370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Gly Ala Pro His Ala Val Glu Ala Leu Val Lys Gln Pro Pro
            435                 440                 445

Asp Arg Trp Leu Ser Asn Ala Arg Met Thr His Tyr Gln Ala Leu Leu
            450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
            485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
            515                 520                 525

Leu Gln Glu Gly Gln Arg Lys Ala Gly Ala Ala Val Thr Thr Glu Thr
            530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
            565                 570                 575

Lys Leu Asn Val Tyr Thr Asp Ser Arg Tyr Ala Phe Ala Thr Ala His
            580                 585                 590

Ile His Gly Glu Ile Tyr Arg Arg Gly Leu Leu Thr Ser Glu Gly
            595                 600                 605

Lys Glu Ile Lys Asn Lys Asp Glu Ile Leu Ala Leu Leu Lys Ala Leu
            610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
            645                 650                 655

Arg Lys Ala Ala Ile Thr Glu Thr Pro Asp Thr Ser Thr Leu Leu
            660                 665                 670

<210> SEQ ID NO 33
<211> LENGTH: 671
<212> TYPE: PRT
<213> ORGANISM: Moloney murine leukemia virus

<400> SEQUENCE: 33

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu

```
            35                  40                  45
Ile Ile Pro Leu Lys Ala Thr Ser Thr Pro Val Ser Ile Lys Gln Tyr
 50                  55                  60

Pro Met Ser Gln Lys Ala Arg Leu Gly Ile Lys Pro His Ile Gln Arg
 65                  70                  75                  80

Leu Leu Asp Gln Gly Ile Leu Val Pro Cys Gln Ser Pro Trp Asn Thr
                 85                  90                  95

Pro Leu Leu Pro Val Lys Lys Pro Gly Thr Asn Asp Tyr Arg Pro Val
                100                 105                 110

Gln Asp Leu Arg Glu Val Asn Lys Arg Val Glu Asp Ile His Pro Thr
            115                 120                 125

Val Pro Asn Pro Tyr Asn Leu Leu Ser Gly Leu Pro Pro Ser His Gln
            130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
                180                 185                 190

Lys Asn Ser Pro Thr Leu Phe Asp Glu Ala Leu His Arg Asp Leu Ala
            195                 200                 205

Asp Phe Arg Ile Gln His Pro Asp Leu Ile Leu Leu Gln Tyr Val Asp
            210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
                260                 265                 270

Leu Lys Glu Gly Gln Arg Trp Leu Thr Glu Ala Arg Lys Glu Thr Val
            275                 280                 285

Met Gly Gln Pro Thr Pro Lys Thr Pro Arg Gln Leu Arg Arg Phe Leu
290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
                340                 345                 350

Thr Ala Pro Ala Leu Gly Leu Pro Asp Leu Thr Lys Pro Phe Glu Leu
            355                 360                 365

Phe Val Asp Glu Lys Gln Gly Tyr Ala Lys Gly Val Leu Thr Gln Lys
            370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
            435                 440                 445

Asp Arg Trp Leu Ser Lys Ala Arg Met Thr His Tyr Gln Ala Leu Leu
            450                 455                 460
```

-continued

```
Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
            515                 520                 525

Leu Gln Glu Gly Gln Arg Lys Ala Gly Ala Ala Val Thr Thr Glu Thr
530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Leu Leu Thr Ser Glu Gly
            595                 600                 605

Lys Glu Ile Lys Asn Lys Asp Glu Ile Leu Ala Leu Leu Lys Ala Leu
610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu
                660                 665                 670

<210> SEQ ID NO 34
<211> LENGTH: 671
<212> TYPE: PRT
<213> ORGANISM: Moloney murine leukemia virus

<400> SEQUENCE: 34

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
                20                  25                  30

Trp Ala Glu Thr Gly Gly Met Gly Leu Ala Val Arg Gln Ala Pro Leu
            35                  40                  45

Ile Ile Pro Leu Lys Ala Thr Ser Thr Pro Val Ser Ile Lys Gln Tyr
50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
            115                 120                 125

Val Pro Asn Pro Tyr Asn Leu Leu Ser Gly Leu Pro Pro Ser His Gln
            130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
```

-continued

```
            165                 170                 175
Met Gly Ile Ser Gly Gln Leu Thr Trp Thr Arg Leu Pro Gln Gly Phe
                180                 185                 190
Lys Asn Ser Pro Thr Leu Phe Asp Glu Ala Leu His Arg Asp Leu Ala
            195                 200                 205
Asp Phe Arg Ile Gln His Pro Asp Leu Ile Leu Leu Gln Tyr Val Asp
        210                 215                 220
Asp Leu Leu Leu Ala Ala Thr Ser Glu Leu Asp Cys Gln Gln Gly Thr
225                 230                 235                 240
Arg Ala Leu Leu Gln Thr Leu Gly Asn Leu Gly Tyr Arg Ala Ser Ala
                245                 250                 255
Lys Lys Ala Gln Ile Cys Gln Lys Gln Val Lys Tyr Leu Gly Tyr Leu
            260                 265                 270
Leu Lys Glu Gly Gln Arg Trp Leu Thr Glu Ala Arg Lys Glu Thr Val
        275                 280                 285
Met Gly Gln Pro Thr Pro Lys Thr Pro Arg Gln Leu Arg Arg Phe Leu
        290                 295                 300
Gly Thr Ala Gly Phe Cys Arg Leu Phe Ile Pro Gly Phe Ala Glu Met
305                 310                 315                 320
Ala Ala Pro Leu Tyr Pro Leu Thr Lys Thr Gly Thr Leu Phe Asn Trp
                325                 330                 335
Gly Pro Asp Gln Gln Lys Ala Tyr Gln Glu Ile Lys Gln Ala Leu Leu
                340                 345                 350
Thr Ala Pro Ala Leu Gly Leu Pro Asp Leu Thr Lys Pro Phe Glu Leu
                355                 360                 365
Phe Val Asp Glu Lys Gln Gly Tyr Ala Lys Gly Val Leu Thr Gln Lys
        370                 375                 380
Leu Gly Pro Trp Arg Arg Pro Val Ala Tyr Leu Ser Lys Lys Leu Asp
385                 390                 395                 400
Pro Val Ala Ala Gly Trp Pro Pro Cys Leu Arg Met Val Ala Ala Ile
                405                 410                 415
Ala Val Leu Thr Lys Asp Ala Gly Lys Leu Thr Met Gly Gln Pro Leu
                420                 425                 430
Val Ile Leu Ala Pro His Ala Val Glu Ala Leu Val Lys Gln Pro Pro
            435                 440                 445
Asp Arg Trp Leu Ser Asn Ala Arg Met Thr His Tyr Gln Ala Leu Leu
        450                 455                 460
Leu Asp Thr Asp Arg Val Gln Phe Gly Pro Val Val Ala Leu Asn Pro
465                 470                 475                 480
Ala Thr Leu Leu Pro Leu Pro Glu Glu Gly Leu Gln His Asn Cys Leu
                485                 490                 495
Asp Ile Leu Ala Glu Ala His Gly Thr Arg Pro Asp Leu Thr Asp Gln
            500                 505                 510
Pro Leu Pro Asp Ala Asp His Thr Trp Tyr Thr Asp Gly Ser Ser Leu
            515                 520                 525
Leu Gln Glu Gly Gln Arg Lys Ala Gly Ala Ala Val Thr Thr Glu Thr
        530                 535                 540
Glu Val Ile Trp Ala Lys Ala Leu Pro Ala Gly Thr Ser Ala Gln Arg
545                 550                 555                 560
Ala Glu Leu Ile Ala Leu Thr Gln Ala Leu Lys Met Ala Glu Gly Lys
                565                 570                 575
Lys Leu Asn Val Tyr Thr Asp Ser Arg Tyr Ala Phe Ala Thr Ala His
            580                 585                 590
```

Ile His Gly Glu Ile Tyr Arg Arg Arg Gly Leu Leu Thr Ser Glu Gly
            595                 600                 605

Lys Glu Ile Lys Asn Lys Asp Glu Ile Leu Ala Leu Leu Lys Ala Leu
            610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
            645                 650                 655

Arg Lys Ala Ala Ile Thr Glu Thr Pro Asp Thr Ser Thr Leu Leu
            660                 665                 670

<210> SEQ ID NO 35
<211> LENGTH: 671
<212> TYPE: PRT
<213> ORGANISM: Moloney murine leukemia virus

<400> SEQUENCE: 35

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Lys Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Arg Phe Leu

```
            290                 295                 300
Gly Thr Ala Gly Phe Cys Arg Leu Phe Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
                340                 345                 350

Thr Ala Pro Ala Leu Gly Leu Pro Asp Leu Thr Lys Pro Phe Glu Leu
                355                 360                 365

Phe Val Asp Glu Lys Gln Gly Tyr Ala Lys Gly Val Leu Thr Gln Lys
                370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
                420                 425                 430

Val Ile Gly Ala Pro His Ala Val Glu Ala Leu Val Lys Gln Pro Pro
                435                 440                 445

Asp Arg Trp Leu Ser Lys Ala Arg Met Thr His Tyr Gln Ala Leu Leu
                450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
                500                 505                 510

Pro Leu Pro Asp Ala Asp His Thr Trp Tyr Thr Asn Gly Ser Ser Leu
                515                 520                 525

Leu Gln Glu Gly Gln Arg Lys Ala Gly Ala Ala Val Thr Thr Glu Thr
                530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
                580                 585                 590

Ile His Gly Glu Ile Tyr Arg Arg Arg Gly Leu Leu Thr Ser Glu Gly
                595                 600                 605

Lys Glu Ile Lys Asn Lys Asp Glu Ile Leu Ala Leu Leu Lys Ala Leu
                610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu
                660                 665                 670

<210> SEQ ID NO 36
<211> LENGTH: 5
<212> TYPE: PRT
<213> ORGANISM: Moloney murine leukemia virus

<400> SEQUENCE: 36
```

Arg Lys Phe Gly Lys
1               5

<210> SEQ ID NO 37
<211> LENGTH: 4
<212> TYPE: PRT
<213> ORGANISM: Moloney murine leukemia virus

<400> SEQUENCE: 37

Arg Phe Gly Lys
1

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
accctaaata tagaagatga gcatcg                                        26

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gaggagggta gaggtgtctg gagtc                                         25

<210> SEQ ID NO 40
<211> LENGTH: 95
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(69)
<223> OTHER INFORMATION: a, c, t or g

<400> SEQUENCE: 40
cttggccaag gatccgctcg agctacttac ttannnnnnn nnnnnnnnnn nnnnnnnnn    60 nnnnnnnnng aggagggtag aggtgtctgg agtct                              95

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
agcggataac aattcccctc tagaattcga                                    30

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic

```
      primer
<220> FEATURE:
<221> NAME/KEY: modified_base
<222> LOCATION: (13)..(14)
<223> OTHER INFORMATION: a, c, g or t

<400> SEQUENCE: 42
cccatgtcac aannkgccag actggg                                              26

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(13)
<223> OTHER INFORMATION: a, c, t or g

<400> SEQUENCE: 43
gacaactaag gnnkttccta gggacg                                              26

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g or t

<400> SEQUENCE: 44
caactaaggg agnnkctagg gacggc                                              26

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (11)..(12)
<223> OTHER INFORMATION: a, c, g or t

<400> SEQUENCE: 45
ggagttccta nnkacggcag gcttc                                               25

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(13)
<223> OTHER INFORMATION: a, c, g or t

<400> SEQUENCE: 46
tctgtcgcct cnnkatccct gggtttg                                             27
```

```
<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g or t

<400> SEQUENCE: 47
ccactagtca ttnnkgcccc ccatgcag                                          28

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(13)
<223> OTHER INFORMATION: a, c, g or t

<400> SEQUENCE: 48
gctggctttc cnnkgcccgg atgactc                                           27

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (12)..(13)
<223> OTHER INFORMATION: a, c, g or t

<400> SEQUENCE: 49
gaggcaaccg gnnkgctgac caagcg                                            26

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g or t

<400> SEQUENCE: 50
cccagtctgg cmnnttgtga catggg                                            26

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g or t
```

<400> SEQUENCE: 51
cgtccctagg aamnncctta gttgtc                                    26

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (13)..(14)
<223> OTHER INFORMATION: a, c, g or t

<400> SEQUENCE: 52
gccgtcccta gmnnctccct tagttg                                    26

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g or t

<400> SEQUENCE: 53
gaagcctgcc gtmnntagga actcc                                     25

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: a, c, g or t

<400> SEQUENCE: 54
caaacccagg gatmnngagg cgacaga                                   27

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: a, c, g or t

<400> SEQUENCE: 55
ctgcatgggg ggcmnnaatg actagtgg                                  28

<210> SEQ ID NO 56
<211> LENGTH: 27
<212> TYPE: DNA
<213> ORGANISM: Artificial Sequence
<220> FEATURE:

```
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: a, c, g or t

<400> SEQUENCE: 56
gagtcatccg ggcmnnggaa agccagc                                          27

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(15)
<223> OTHER INFORMATION: a, c, g or t

<400> SEQUENCE: 57
cgcttggtca gcmnnccggt tgcctc                                           26

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58 tacccatgt cacaaaaagc cagactgggg atcaag                                 36

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggcttctgtc gcctctttat ccctgggttt gc                                    32

<210> SEQ ID NO 60
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cagccactag tcattggggc cccccatgca gtag                                  34

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gaccgctggc tttccaaggc ccggatgact cac                                   33
```

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gggggggggg gggggggg                                                 18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
tttttttttt tttttttt                                                 18

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

His Ser Arg Arg Arg Leu Lys Arg His Ile Phe Asn
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Lys Arg Thr Asn Pro Ile Asn Ile His Thr Asn Lys
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Glu Gly Lys Asn Arg Gln Gly Glu Gly Gln Thr
1               5                   10

<210> SEQ ID NO 67
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

-continued

Arg Asp Arg Asn Lys Asn Asn Asp Arg Arg Lys Ala Lys Arg Asp Arg
1               5                   10                  15

Asn Lys Asn Asn Asp Arg Arg Lys Ala Lys
            20                  25

<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Asp Arg Asn Lys Asn Asn Asp Arg Arg Lys Ala Lys Glu Asn Glu
1               5                   10                  15

Glu Asn Glu Glu Asn Glu Glu Asn Glu Glu Asn Glu
            20                  25

<210> SEQ ID NO 69
<211> LENGTH: 243
<212> TYPE: PRT
<213> ORGANISM: Escherichia coli

<400> SEQUENCE: 69

Met Ser Thr Ala Ile Thr Arg Gln Ile Val Leu Asp Thr Glu Thr Thr
1               5                   10                  15

Gly Met Asn Gln Ile Gly Ala His Tyr Glu Gly His Lys Ile Ile Glu
            20                  25                  30

Ile Gly Ala Val Glu Val Val Asn Arg Arg Leu Thr Gly Asn Asn Phe
        35                  40                  45

His Val Tyr Leu Lys Pro Asp Arg Leu Val Asp Pro Glu Ala Phe Gly
    50                  55                  60

Val His Gly Ile Ala Asp Glu Phe Leu Leu Asp Lys Pro Thr Phe Ala
65                  70                  75                  80

Glu Val Ala Asp Glu Phe Met Asp Tyr Ile Arg Gly Ala Glu Leu Val
                85                  90                  95

Ile His Asn Ala Ala Phe Asp Ile Gly Phe Met Asp Tyr Glu Phe Ser
            100                 105                 110

Leu Leu Lys Arg Asp Ile Pro Lys Thr Asn Thr Phe Cys Lys Val Thr
        115                 120                 125

Asp Ser Leu Ala Val Ala Arg Lys Met Phe Pro Gly Lys Arg Asn Ser
    130                 135                 140

Leu Asp Ala Leu Cys Ala Arg Tyr Glu Ile Asp Asn Ser Lys Arg Thr
145                 150                 155                 160

Leu His Gly Ala Leu Leu Asp Ala Gln Ile Leu Ala Glu Val Tyr Leu
                165                 170                 175

Ala Met Thr Gly Gly Gln Thr Ser Met Ala Phe Ala Met Glu Gly Glu
            180                 185                 190

Thr Gln Gln Gln Gln Gly Glu Ala Thr Ile Gln Arg Ile Val Arg Gln
        195                 200                 205

Ala Ser Lys Leu Arg Val Val Phe Ala Thr Asp Glu Glu Ile Ala Ala
    210                 215                 220

His Glu Ala Arg Leu Asp Leu Val Gln Lys Lys Gly Gly Ser Cys Leu
225                 230                 235                 240

Trp Arg Ala

```
<210> SEQ ID NO 70
<211> LENGTH: 750
<212> TYPE: DNA
<213> ORGANISM: Escherichia coli

<400> SEQUENCE: 70
cacaggtatt tatgctcgcc agaggcaact tccgcctttc ttctgcacca gatcgagacg      60
ggcttcatga gctgcaatct cttcatctgt cgcaaaaaca acgcgtaact tacttgcctg    120
acgtacaatg cgctgaattg ttgcttcacc ttgttgctgt tgtgtctctc cttccatcgc    180
aaaagccatc gacgtttgac caccggtcat cgccagataa acttccgcaa ggatctgggc    240
atcgagtaat gccccgtgca gcgttcgttt actgttatct atttcgtagc gagcacataa    300
cgcatcgagg ctgttgcgct taccgggaaa cattttcctc gccaccgcaa ggctatcggt    360
gaccttacag aaagtattgg tcttcggaat atcgcgctta agcaacgaaa actcgtagtc    420
cataaagccg atatcgaacg ctgcgttatg gatcaccaac tccgcgccgc gaatatagtc    480
catgaactca tcggctactt cggcaaacgt gggcttatcg agcaaaaatt catcggcaat    540
accatgtacg ccaaaggctt ccggatccac cagccgatcg ggtttgagat aaacatggaa    600
gttattgccc gtcaggcgac ggttcaccac ttcaacggca ccaatctcaa tgatcttgtg    660
gccttcatag tgcgcaccaa tctggttcat accggtggtt tcggtatcga gaacgatctg    720
gcgtgtaatt gcagtgctca tagcggtcat                                     750
```